US008375768B2

(12) United States Patent
Zeng et al.

(10) Patent No.: US 8,375,768 B2
(45) Date of Patent: Feb. 19, 2013

(54) IONIC LIQUID THIN LAYER SENSOR FOR ELECTROCHEMICAL AND/OR PIEZOELECTRIC MEASUREMENTS

(75) Inventors: Xiangqun Zeng, Rochester Hills, MI (US); Lei Yu, Auburn Hills, MI (US); Yue Huang, East Lansing, MI (US); Andrew J. Mason, Portland, MI (US)

(73) Assignees: Oakland University, Rochester, MI (US); Board of Trustees of Michigan State University, East Lansing, MI (US)

( * ) Notice: Subject to any disclaimer, the term of this patent is extended or adjusted under 35 U.S.C. 154(b) by 709 days.

(21) Appl. No.: 12/387,600

(22) Filed: May 5, 2009

(65) Prior Publication Data

US 2009/0293590 A1 Dec. 3, 2009

Related U.S. Application Data

(63) Continuation-in-part of application No. 11/725,637, filed on Mar. 20, 2007, now Pat. No. 7,886,577.

(60) Provisional application No. 60/787,594, filed on Mar. 30, 2006.

(51) Int. Cl.
*G01N 29/02* (2006.01)
(52) U.S. Cl. .................................... 73/24.06; 73/24.01
(58) Field of Classification Search ........................ None
See application file for complete search history.

(56) References Cited

U.S. PATENT DOCUMENTS

| 3,327,519 A | 6/1967 | Crawford |
| 4,236,893 A | 12/1980 | Rice |
| 4,242,096 A | 12/1980 | Oliveira et al. |
| 4,246,344 A | 1/1981 | Silver, III |
| 4,314,821 A | 2/1982 | Rice |
| 4,735,906 A | 4/1988 | Bastiaans |
| 4,788,466 A | 11/1988 | Paul et al. |
| 4,999,284 A | 3/1991 | Ward et al. |
| 5,117,192 A | 5/1992 | Hurd |
| 5,201,215 A | 4/1993 | Granstaff et al. |

(Continued)

FOREIGN PATENT DOCUMENTS

| WO | WO 02079212 | 10/2002 |
| WO | WO 02094883 | 11/2002 |

(Continued)

OTHER PUBLICATIONS

X. Jin, Y. Huang, A. Mason, X. Zeng, "Multichannel monolithic quartz crystal microbalance gas sensor array," Anal. Chem. Published on web Dec. 17, 2008. Accessed online Sep. 26, 2011 at <http://pubs.acs.org/doi/abs/10.1021/ac8018697>.*

(Continued)

*Primary Examiner* — Lisa Caputo
*Assistant Examiner* — Punam Roy
(74) *Attorney, Agent, or Firm* — Butzel Long

(57) ABSTRACT

An electrochemical piezoelectric sensor is disclosed. The sensor includes a piezoelectric substrate, three (or more) electrodes over a first surface of the substrate, and another electrode over a second (opposing) surface of the substrate. An ionic liquid in the form of a film is adhered, bound, immobilized, or otherwise positioned over the substrate and electrodes of the first surface. The ionic liquid film permits the absorption and detection of analytes from a gaseous sample, for environmental gases, example explosive vapors and/or explosive vapor species in the gaseous sample. Detection (optionally including analyte quantitation and qualitative identification) can be performed by both electrochemical and piezoelectric techniques using a single sensor. Systems incorporating and methods of using the electrochemical piezoelectric sensor also are disclosed.

48 Claims, 54 Drawing Sheets

U.S. PATENT DOCUMENTS

| | | | |
|---|---|---|---|
| 5,233,261 | A | 8/1993 | Wajid |
| 5,282,925 | A | 2/1994 | Jeng et al. |
| 5,314,830 | A | 5/1994 | Anderson et al. |
| 5,484,626 | A | 1/1996 | Storjohann et al. |
| 5,616,827 | A | 4/1997 | Simmermon et al. |
| 5,622,826 | A | 4/1997 | Varma |
| 5,706,840 | A | 1/1998 | Schneider |
| 5,795,993 | A | 8/1998 | Pfeifer et al. |
| 5,885,402 | A | 3/1999 | Esquibel |
| 5,932,953 | A | 8/1999 | Drees et al. |
| 6,087,187 | A | 7/2000 | Wiegand |
| 6,106,149 | A | 8/2000 | Smith |
| 6,190,035 | B1 | 2/2001 | Smith |
| 6,319,674 | B1 | 11/2001 | Fulcrand et al. |
| 6,368,877 | B1 | 4/2002 | Zhang et al. |
| 6,439,765 | B2 | 8/2002 | Smith |
| 6,475,808 | B1 | 11/2002 | Wagner et al. |
| 6,475,809 | B1 | 11/2002 | Wagner et al. |
| 6,492,601 | B1 | 12/2002 | Cain et al. |
| 6,579,343 | B2 | 6/2003 | Brennecke et al. |
| 6,647,764 | B1 | 11/2003 | Paul et al. |
| 6,706,977 | B2 | 3/2004 | Cain et al. |
| 6,848,299 | B2 | 2/2005 | Paul et al. |
| 6,852,229 | B2 | 2/2005 | Mehnert et al. |
| 6,890,486 | B2 | 5/2005 | Penelle |
| 7,464,580 | B2 | 12/2008 | Zeng et al. |
| 2002/0094531 | A1 | 7/2002 | Zenhausern |
| 2002/0142477 | A1 | 10/2002 | Lewis et al. |
| 2003/0049204 | A1 | 3/2003 | Leyland-Jones |
| 2003/0053950 | A1 | 3/2003 | Leyland-Jones |
| 2003/0068273 | A1 | 4/2003 | Leyland-Jones |
| 2003/0072710 | A1 | 4/2003 | Leyland-Jones |
| 2003/0073133 | A1 | 4/2003 | Leyland-Jones |
| 2003/0077222 | A1 | 4/2003 | Leyland-Jones |
| 2003/0204041 | A1 | 10/2003 | Laas et al. |
| 2004/0054231 | A1 | 3/2004 | Abbott et al. |
| 2004/0262578 | A1 | 12/2004 | Wasserscheid et al. |
| 2005/0005840 | A1 | 1/2005 | Bonrath et al. |
| 2005/0252273 | A1 | 11/2005 | Imoto |
| 2006/0188399 | A1 | 8/2006 | Smid |

FOREIGN PATENT DOCUMENTS

| | | |
|---|---|---|
| WO | WO 03051894 | 6/2003 |

OTHER PUBLICATIONS

T. Tatsuma, Y. Watanabe, N. Oyama, "Multichannel quartz crystal microbalance," Anal. Chem. 1999, 71, 3632-3636.*
Y. Shen, Y. Zhang, X. Qui, H. Guo, L. Niu, and A. Ivaska, "Polyelectrolyte-functionalized ionic liquid for electrochemistry in supporting electrolyte-free aqueous solutions and application in amperometric flow injection analysis" Green Chem., 2007, 9, pp. 746-753.*
Decastro, C., et al., J. Catalysis, 196, 86-94 (2000).
Chum, H.L., et al., J. Am. Chem. Soc., 97, 3264 (1975).
Zhao, D.B., et al., Catalysis Today, 74, 157-189 (2002).
Olivier-Bourbigou, H., et al., J. Molecular Catalysis A: Chemical, 182-183, 419-437 (2002).
Bradaric, C.J., et al., in Industrial Preparation of Phosphonium Ionic Liquids, ACS Symposium Series 856; Roger, R.D., et al., Edt. American Chemical Society (2003).
Samaha, H. et al., Biocatalysis of Chlorophyllase in Ternary Micellar Systems Using Pheophytins as Substrates, J. Chem. Tech. Biotech, 68, 315-323 (1997).
Welton, T, in Room-Temperature Ionic Liquids: Solvents for synthesis and Catalysis, Chem. Rev., 99, 2071-2083 (1999).
Visser, A.E., et al., in Task-specific ionic liquids for the extraction of metal ions from aqueous solutions, Chem. Comm. 135 (2001).
Bates, E.D., et al., J. Am. Chem. Soc. 124, 926 (2002).
Baker, G.A., et al., in An Analytical view of ionic liquids, The Analyst, 130, 800-808 (2005).
Handy, S.T., Chem. Eur. J., 9, 2938-2944 (2003).
Ding, J., et al., Chem. Mater., 15, 2392-2398 (2003).
Jensen, M.P., et al., J. Am. Chem. Soc. 125, 15466-15473 (2003).
Yang, C., et al., J. phys. Chem. B, 107, 12981-12988 (2003).
Barisci, J.N., et al., Electrochem. Commun. 6, 22-27 (2004).
Wang, P., et al., J. Phys. Chem. B, 107, 13280-13285 (2003).
Liu, W.M., et al., Tribology Letters, 13, 81-85 (2002).
Wang, H.Z., et al., Wear, 256, 44-48 (2004).
Ye, C.F., et al., Wear, 253, 579-584 (2002).
Tsang et al., J. Phys. Chem. B, 2001, 105, 5737-5742.
Kaltenpoth et al., Anal. Chem., 2003, 75, 4756-4765.
Dutta et al., J. Phys. Chem. B, 1999, 103, 4412-4422.
Zhu et al., Anal. Chem., 2002, 74, 120-124.
Simon et al. J. Comb. Chem., 2002, 4, 511-515.
Hu et al., J. Phys. Chem. B, 2004, 108, 11214-11218.
Wang et al., J. Am. Chem. Soc., 2003, 125, 16176-16177.
Dutta et al., Chem. Mater., 2004, 16, 5198-5204.
Grate et al., Anal. Chem., 1993, 65, 987A.
Jarrett and Finklea, Anal. Chem., 1999, 71, 353.
Shinar et al., Anal. Chem., 2000, 72, 5981.
Zellers et al., Anal. Chem., 1995, 67, 1092.
Patrash and Zellers, Anal. Chem., 1993, 65, 2055.
Yang et al., Nature Materials 1: 253-257 (2002).
Bonhote, P., et al., Inorg. Chem., 35, 1168 (1996).
Hsieh, M., et al., Anal. Chem., 76, 1885-1895 (2004).
L. Yu., et al., "Ionic liquid high temperature gas sensors" Chem. Commun., 2005, 2277-2279.
Zhang, Z., et al., in EPD Congress (2002).
Liang, C., et al., Anal. Chem. 74, 2172-2176 (2002).
Nuzzo, R.G., et al., in Adsorption of bifunctional organic disulfides on gold surfaces, J. Am. Chem. Soc., 105, 4481-4483 (1983).
Nuzzo, R.G., et al., J. Am. Chem. Soc., 109, 2358-2368 (1987).
Aslanoglu, M., et al., Analyst, 123, 753-757 (1998).
Grate, J.W., et al., Faraday Discuss. 107, 259-283 (1997).
Grate, J.W., et al., Anal. Chem. 70, 199-203 (1998).
McQuade, D.T., et al., Chem. Rev., 100, 2537-2574 (2000).
Tatumi, R., et al., Chem. Commun., 83-85 (2005).
Yoshizawa, M., et al., Chem. Commun., 1828-1829 (2004).
Ohno, H., et al., Electrochimica Acta, 48, 2079-2083 (2003).
Y. Shen, et al., "Immobilization of ionic liquid with polyelectrolyte as carrier" Chem. Commun. 4193-4195 (2005).
I. Goubaidouline, et al., "Organic vapor sensing with ionic liquids entrapped in alumina nanopores on quartz crystal resonators" Anal. Chem. vol. 77, No. 2, 615-619 (2005).
M.H. Valkenberg et al., "Immobilisation of Ionic Liquids on Solid Supports," Green Chemistry, vol. 4, p. 88-93 (2002).
C.P. Mehnert et al., "Supported Ionic Liquid Catalysis Investigated for Hydrogenation Reactions," Chem. Comm., p. 3010-3011 (2002).
D.S. Silvester, A.J. Wain, L. Aldous, C. Hardacre, R.G. Compton, Electrochemical reduction of nitrobenzene and 4-nitrophenol in the room temperature ionic liquid [C(4)dmim][N(Tf)(2)], J. Electroanal. Chem. 596 (2006) 131-140.
D.S. Silvester, R.G. Compton, Electrochemistry in room temperature ionic liquids: A review and some possible applications, Zeitschrift Fur Physikalische Chem.-Inter. J. Res. Phys. Chem. Chem. Phys. 220 (2006) 1247-1274.
M.C. Kroon, W. Buijs, C.J. Peters, G.J. Witkamp, Decomposition of ionic liquids in electrochemical processing, Green Chem. 8 (2006) 241-245.
T. Ueki, M. Watanabe, Macromolecules in Ionic Liquids: Progress, Challenges, and Opportunities, Macromolecules 41 (2008) 3739-3749.
D.S. Moore, Recent Advances in Trace Explosives Detection Instrumentation, Sens. Imaging 8 (2007) 9-38.
M. Nambayah, T.I. Quickenden, A quantitative assessment of chemical techniques for detecting traces of explosives at counter-terrorist portals, Talanta 63 (2004) 461-467.
D.S. Moore, Instrumentation for trace detection of high explosives, Review of Scientific Instrumnets 75 (2004) 2499-2512.
S.J. Toal, W.C. Trogler, Polymer sensors for nitroaromatic explosives detection, J. Mater. Chem. 16 (2006) 2871-2883.
A. Cyr, E. Laviron, J. Lessard, Electrochemical-Behavior of Nitrobenzene and Phenylhydroxylamine on Copper Rotating-Disk Electrodes, J. Electroanal. Chem. 263 (1989) 69-78.
L.J. Nunez-Vergara, M. Bonta, P.A. Navarrete-Encina, J.A. Squella, Electrochemical characterization of ortho and meta-nitrotoluene derivatives in different electrolytic media. Free radical formation, Electrochim. Acta 46 (2001) 4289-4300.

L. Agui, D. Vega-Montenegro, P. Yanez-Sedeno, J.M. Pingarron, Rapid voltammetric determination of nitroaromatic explosives at electrochemically activated carbon-fibre electrodes, Anal. Bioanal. Chem. 382 (2005) 381-387.

J.C. Chen, J.L. Shih, C.H. Liu, M.Y. Kuo, J.M. Zen, Disposable electrochemical sensor for determination of nitroaromatic compounds by a single-run approach, Anal. Chem. 78 (2006) 3752-3757.

S. Hrapovic, E. Majid, Y. Liu, K. Male, J.H.T. Luong, Metallic nanoparticle-carbon nanotube composites for electrochemical determination of explosive nitroaromatic compounds, Anal. Chem. 78 (2006) 5504-5512.

D.L. Lu, A. Cagan, R.A.A. Munoz, T. Tangkuaram, J. Wang, Highly sensitive electrochemical detection of trace liquid peroxide explosives at a Prussian-blue 'artificial-peroxidase' modified electrode, Analyst 131 (2006) 1279-1281.

S.Y. Ly, D.H. Kim, M.H. Kim, Square-wave cathodic stripping voltammetric analysis of RDX using mercury-film plated glassy carbon electrode, Talanta 58 (2002) 919-926.

N. P. Saravanan, S. Venugopalan, N. Senthilkumar, P. Santhosh, B. Kavita, H.G. Prabu, Voltammetric determination of nitroaromatic and nitramine explosives contamination in soil, Talanta 69 (2006) 656-662.

J. Wang, Microchip devices for detecting terrorist weapons, Anal. Chim. Acta 507 (2004) 3-10.

J. Wang, R.K. Bhada, J.M. Lu, D. MacDonald, Remote electrochemical sensor for monitoring TNT in natural waters, Anal. Chim. Acta 361 (1998) 85-91.

J. Wang, S.B. Hocevar, B. Ogoreve, Carbon nanotube-modified glassy carbon electrode for adsorptive stripping voltammetric detection of ultratrace levels of 2,4,6-trinitrotoluene, Electrochem. Commun. 6 (2004) 176-179.

J. Wang, F. Lu, D. MacDonald, J.M. Lu, M.E.S. Ozsoz, K.R. Rogers, Screen-printed voltammetric sensor for TNT, Talanta 46 (1998) 1405-1412.

J. Wang, M. Pumera, Dual conductivity/amperometric detection system for microchip capillary electrophoresis, Anal. Chem. 74 (2002) 5919-5923.

J. Wang, S. Thongngamdee, D.L. Lu, Sensitive voltammetric sensing of the 2,3-dimethyl-2,3-dinitrobutane (Dmnb) explosive taggant, Electroanalysis 18 (2006) 971-975.

H.X. Zhang, A.M. Cao, J.S. Hu, L.J. Wan, S.T. Lee, Electrochemical sensor for detecting ultratrace nitroaromatic compounds using mesoporous SiO2-modified electrode, Anal. Chem. 78 (2006) 1967-1971.

H.X. Zhang, J.S. Hu, C.J. Yan, L. Jiang, L.J. Wan, Functionalized carbon nanotubes as sensitive materials for electrochemical detection of ultra-trace 2,4,6-trinitrotoluene, Phys. Chem. Chem. Phys. 8 (2006) 3567-3572.

X.S. Zhu, C.H. Ahn, On-chip electrochemical analysis system using nanoelectrodes and bioelectronic CMOS chip, Ieee Sensors J. 6 (2006) 1280-1286.

X.X. Jin, L. Yu, D. Garcia, R.X. Ren, X.Q. Zeng, Ionic liquid high-temperature gas sensor array, Anal. Chem. 78 (2006) 6980-6989.

\* cited by examiner

| Structure of Cations | Structure of Anions | Name or Abbreviation of Name |
|---|---|---|
| R₄N⁺ (with C₁₂H₂₅) | -SO₃-Ph-C₁₂H₂₅, (CF₃SO₂)₂N⁻ | $N_{7,7,7}SO_3$-Ph-$C_{12}H_{25}$, $N_{4,4,4}SO_3$-Ph-$C_{12}H_{25}$, $N_{1,4,4,4}(CF_3SO_2)_2N$, $N_{1,8,8,8}(CF_3SO_2)_2N$, $N_{2,6,6,6}(CF_3SO_2)_2N$, $N_{1,1,3,i-3}(CF_3SO_2)_2N$, $N_{1,1,i-3,5}(CF_3SO_2)_2N$, $N_{1,1,i-3,10}(CF_3SO_2)_2N$ |
| R₄P⁺ (with C₁₂H₂₅) | -SO₃-Ph-C₁₂H₂₅, camphorsulfonate, CH₃SO₃⁻, C₃H₇SO₃⁻, C₄H₉SO₃⁻, C₄F₉SO₃⁻ | $P_{6,6,6,14}SO_3$-Ph-$C_{12}H_{25}$, $P_{8,8,8,8}SO_3$-Ph-$C_{12}H_{25}$, $P_{4,4,4,14}SO_3$-Ph-$C_{12}H_{25}$, $P_{6,6,6,14}CH_3SO_3$, $P_{6,6,6,6}(+)$camphorsulfonate, $P_{4,4,4,4}CH_3SO_3$, $P_{6,6,6,14}C_3H_7SO_3$, $P_{6,6,6,14}C_4H_9SO_3$, $P_{6,6,6,14}C_4F_9SO_3$ |
| bmi (C₄H₉, CH₃ imidazolium) | (CF₃SO₂)₂N⁻, (CF₃CF₂SO₂)₂N⁻, CH₃SO₃⁻, BF₄⁻, PF₆⁻, HSO₄⁻ | bmi(CF₃SO₂)₂N, bmi(CF₃CF₂SO₂)₂N, bmi(+)camphorsulfonate, bmiBF₄, bmiPF₆, bmiHSO₄, bmiCH₃SO₃ |
| bbi (C₄H₉, C₄H₉ imidazolium) | (CF₃SO₂)₂N⁻, PF₆⁻ | bbi(CF₃SO₂)₂N, bbiPF₆ |
| bei (C₄H₉, C₂H₅ imidazolium) | camphorsulfonate | beiCH₃SO₃, bei(+)camphorsulfonate |
| pmi (C₃H₇, CH₃ imidazolium) | CH₃SO₃⁻ | pmiCH₃SO₃ |
| N-methylpyrrolidinium (C mpy) | (CF₃SO₂)₂N⁻ | [C3mpy](CF₃SO₂)₂N, [C4mpy](CF₃SO₂)₂N, [C5mpy](CF₃SO₂)₂N, [C6mpy](CF₃SO₂)₂N, [C10mpy](CF₃SO₂)₂N |
| hp (C₆H₁₁ pyridinium) | PF₆⁻ | hpPF₆ |
| bp (C₄H₉ pyridinium) | CH₃SO₃⁻ | bpCH₃SO₃ |

Figure 1

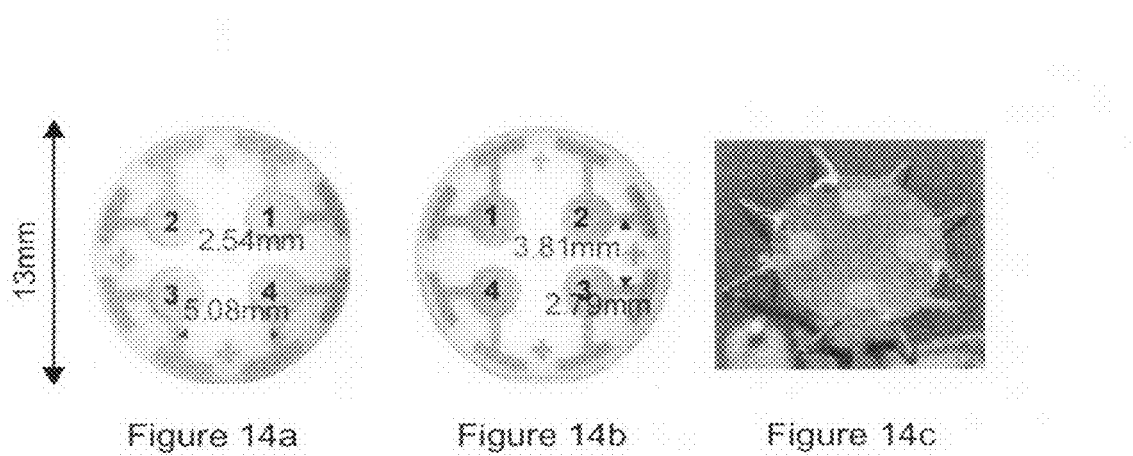

Front Side          Back Side

IONIC LIQUID THIN LAYER SENSOR FOR ELECTROCHEMICAL AND/OR PIEZOELECTRIC MEASUREMENTS

CROSS-REFERENCE TO RELATED APPLICATION

This application is a continuation-in-part of U.S. patent application Ser. No. 11/725,637, filed Mar. 20, 2007, now U.S. Pat. No. 7,886,577 which in turn claims the priority benefit of U.S. Provisional Application No. 60/787,594, filed Mar. 30, 2006, both of which are incorporated herein by reference in their entireties.

STATEMENT REGARDING FEDERALLY SPONSORED RESEARCH OR DEVELOPMENT

This research was partly supported by grants from the National Institute of Health (NIH R33EB00672 B1) and The U.S. government has certain rights to this invention.

BACKGROUND OF THE DISCLOSURE

1. Field of the Disclosure

The present disclosure relates generally to improved devices comprising surface-bound ionic liquids for solvating organic compounds and/or common environmental gases (e.g., $CO_2$, $H_2S$). Specifically, the present disclosure relates to piezoelectric gas sensors (e.g., QCM sensors) with bound films of ionic liquids which are capable of detecting volatile organic compounds such as both polar and nonpolar organic vapors and some inorganic gases such as carbon dioxide at both room and high temperatures. In another embodiment, the thin-film ionic liquid provides a basis for the amperometric (e.g., voltammetry) and/or piezoelectric (e.g., QCM) measurement of solvated organic compounds, including volatile explosive organic compounds (e.g., nitroaromatics).

2. Brief Description of Related Technology

Room-temperature ionic liquids are a relatively new class of compounds containing organic cations and anions, which melt at or close to room temperature. An early group of ionic liquids reported by Osteryoung et al. was composed of a mixture of 1-butylpyridinium chloride and aluminum chloride that was liquid at room temperature (Decastro, C., et al., J. Catalysis, 196, 86-94 (2000); and Chum, H. L., et al., J. Am. Chem. Soc., 97, 3264 (1975)). Soon after, a series of ILs based on the cations of alkylpyridinium or dialkylimidazolium were developed. The anions vary from halides, such as $Cl^-$, $Br^-$ or $AlCl_4^-$ to coordinates, such as $BF_4^-$, $PF_6^-$, $SbF_6^-$, or $NO_3^-$, $SO_4^-$, $CuCl_2^-$, and organics, such as $CH_3SO_3^-$, or $(CF_3SO_2)_2N^-$ (Zhao, D. B., et al., Catalysis Today, 74, 157-189 (2002); and Olivier-Bourbigou, H., et al., J. Molecular Catalysis A: Chemical, 182-183, 419-437 (2002)). In the last decade, ILs based on cations of tetraalkylammonium or tetraalkylphosphonium and anions of phosphinate (Robertson, A. J., et al., WO 2002079212; Bradaric, C. J., et al., in Industrial Preparation of Phosphonium Ionic Liquids, ACS Symposium Series 856; Roger, R. D., et al., Edt. American Chemical Society (2003)), alkanesulfonate and alkylbenzenesulfonate (Wasserscheid, P., et al., in New Ionic Liquids Based on Alkylsulfate and Alkyl Oligoether Sulfate Anions: Synthesis and Applications, ACS symposium Series 856, Ionic Liquids as Green Solvents, Progress and Prospects, R. D. Roger and K. R. Seddon Ed., American Chemical Society (2003)) were developed, which are "pure organic" ILs that are more stable, especially at relatively higher temperatures, less toxic and more hydrophobic. Due to its unique properties and increasing availability, room temperature ionic liquids have attracted significant research interest in the past few years.

In contrast to conventional organic solvents that are composed of molecular entities such as DMSO, DMF, $CH_2Cl_2$, $CHCl_3$, or THF, ionic liquids have unique properties (Seddon, K. R., in Ionic Liquids for Clean Technology, J. Chem. Tech. Biotech, 68, 315-316 (1997)). They have no significant vapor pressure, thus allowing chemical processes to be carried out with essentially zero emission of toxic organic solvents into the environment. Consequently, they have been considered a possibly environmentally friendly, recyclable media for synthetic organic chemistry, separation sciences and other chemical sciences and engineering (Welton, T, in Room-Temperature Ionic Liquids: Solvents for synthesis and Catalysis, Chem. Rev., 99, 20071-2083 (1999)). For example, ionic liquids have been used as solvents for organic reactions (nucleophilic and electrophilic reactions including acid catalyzed reactions), transition metal catalyzed reactions, and biotransformations (Rogers, R. D., et al., Ionic Liquids: Industrial Application of Green Chemistry, ACS Symposium Series 818, (2002); and Rogers, R. D., et al., Ionic Liquids as Green Solvents: Progress and Prospects, ACS Symposium Series 856 (2002)). In addition to enhanced reaction rates and improved chemo- and regioselectivities relative to other organic solvents, ILs also provide potential solutions for biphasic separation of reaction products via extraction, i.e. products can be obtained through distillation from these non-volatile reaction media which eliminates the need for noxious organic solvents (Visser, A. E., et al., in Task-specific ionic liquids for the extraction of metal ions from aqueous solutions, Chem. Comm. 135 (2001); Bates, E. D., et al., J. Am. Chem. Soc. 124, 926 (2002)). Ionic liquids usually have low miscibility with a number of organic solvents (such as ethers, hexane, or ethyl acetate) as well as supercritical carbon dioxide (Blanchard, L. A., et al., Nature 399, 28 (1999). Consequently, organic compounds can be extracted into supercritical carbon dioxide from ionic liquids.

Ionic liquids possess high ion concentration, high heat capacity and good electrochemical stability. They prove to be excellent candidates for highly efficient heat transfer fluids, supporting media for catalysts as well as electrochemical devices including super capacitors, fuel cells, lithium batteries, photovoltaic cells, electrochemical mechanical actuators and electroplating (Seddon, K. R., J. Chem. Tech. Biotech, 68, 315-316 (1997)). Recently, reports for the use of ILs as lubricants for steels joints (Welton, T., Chem. Rev., 99, 2071-2083 (1999); Rogers, R. D., et al., ACS Symposium Series 818 (2002); and Rogers, R. D., et al., ACS Symposium Series 856 (2002)) show that the ILs exhibits excellent friction-reduction, antiwear properties, both in air and in vacuum, which are superior to phosphazene and perfluoropolyether.

Even though significant progresses in the study of ILs have been made in the past decade, the bulk of current research of ILs is focused on their use as solvents for chemical reactions, separations and electrochemistry. Limited efforts have been made to explore ILs potential for analytical applications (Baker, G. A., et al., in An Analytical view of ionic liquids, The Analyst, 130, 800-808 (2005)). Much fundamental research effort is needed to bring forth the benefits of ILs. There is a need to address this issue and explore ionic liquids surface chemistry and its application as gas sensing materials.

Gas sensors are of increasing interest because of their potential for widespread application in ambient air monitoring, occupational health and safety, biomedical diagnostics, industrial process control, and military and civilian counter-terrorism. Sorptive-polymer interface layers have been extensively explored to temporarily concentrate the vapors near the sensor surface and to facilitate detection by whatever transduction mechanism is employed in the sensing devices (Blanchard, L. A., Nature 399, 28 (1999)). It is now generally accepted that the non-bonding vapor-polymer sorption interactions in sensor arrays do not afford sufficient collective selectivity for quantitative determinations of more than a few vapors simultaneously regardless of the number of sensors or the sensor technology employed (Handy, S.T., Chem. Eur. J., 9, 2938-2944 (2003); Ding, J., et al., Chem. Mater., 15, 2392-2398 (2003); Jensen, M. P., et al., J. Am. Chem. Soc. 125, 15466-15473 (2003); Yang, C., et al., J. phys. Chem. B, 107, 12981-12988 (2003); Barisci, J. N., et al., Electrochem. Commun. 6, 22-27 (2004); Wang, P., et al., J. Phys. Chem. B, 107, 13280-13285 (2003)). Ionic liquids with their unique properties could potentially overcome above limitation for gas detection: (1) ILs are excellent solvents that can support many types of solvent-solute interactions (hydrogen bond, $\pi$-$\pi$, dipolar, ionic., and the like). Many different interaction types may be simultaneously present in ILs, and the resulting properties of the ILs depend on which interactions are dominant. Consequently, surface design of ILs can be used to fit a particular sensing application; (3) ILs have negligible vapor pressure so that there is no drying out of the electrolyte, which is a serious problem for sensors using solid polymer electrolyte films, which reduces hazards, associated with flash points and flammability; (4) ILs possesses high thermal stability (Liu, W. M., et al., Tribology Letters, 13, 81-85 (2002)). Most ILs show typical decomposition temperatures of 350+° C. This remarkable thermal stability has important implications in the use of ILs for high temperature sensing; (5) Ionic liquids suppress conventional solvation and solvolysis phenomena, and provide media capable to dissolve a vast range of organic molecules to very high concentrations. One of the most exciting and impressive potential industrial applications of ionic liquid is their use for the storage and delivery of gases that are highly toxic, flammable, and/or reactive. Air Products has developed a subatmospheric ionic-liquid-based technology for storing and delivering gases that offers a number of advantages over the solid physical-adsorption technology. This indicates great potential in organic volatile sensing. (6) Synthetic flexibility of ionic liquids allowing them to be tailored to be chemically independent; One ion could be use to deliver one function and the second ion to deliver a different, completely independent function (Wang, H. Z., et al., Wear, 256, 44-48 (2004)). Functionalized ionic liquids are being developed that not only act as solvents but also as materials for particular applications (Ye, C. F., et al., Wear, 253, 579-584 (2002)). While there are about 300 organic solvents widely used in the chemical industry, there are potentially many more useful ionic liquids; (7) The unique charge properties allow easy construction of IL on preformed templates which could generate complex chemical selective films. In summary, IL's offer tremendous diversity in structural and chemical properties and their unique properties offer an excellent opportunity to design an array of chemically selective IL films and explore their application in pattern recognition for various analytes.

Many research groups are developing new materials and transducers for gas sensing with particular emphasis on optimizing interface properties among the gas phase, the sensitive materials and the transducer. For example, self-assembled monolayers (SAM) have been used to construct functional organic surfaces (Baker, G. A., et al., The Analyst, 130-800-808 (2005)). They have the advantage of being easily and reproducibly synthesized, and the analysis rate is typically fast since they do not need to penetrate through a diffusion barrier. The disadvantage of SAM is that the chemical selectivity depends only on the terminal groups, making the degree of chemical selectivity that can be engineered into simple SAM not as great as in thicker or more complex materials. Moreover, the total number of receptors incorporated in the film and thus the dynamic range and sensitivity of the sensor, is limited by the surface area of the substrate. In order to overcome the disadvantages of SAM, stepwise self-assembled bilayers were reported (Baker, G. A., et al., The Analyst, 130, 800-808 (2005)), which can produce films of complex molecules and molecular assemblies. However, self-assembled films of complex molecules and molecular assemblies are difficult to prepare.

Thin films made from ILs can perform well as sensor interfaces and provide additional control over selectivity and sensitivity when interacting with analytes in gas phase. Most organic solvents or vapors are soluble in ILs. Therefore, the partition process will reach equilibrium very fast after the sensor is exposed to the vapors. This ensures a fast response and excellent reversibility. At equilibrium, the distribution of organic vapors in the IL phase and the gas phase will depend on the partial pressure of the vapors so quantitative measurement is feasible. ILs have zero vapor pressure and work in a very large temperature range which is ideal for industrial high temperature sensing applications.

ILs possess high ion concentration, high heat capacity and good electrochemical stability. They prove to be excellent candidates for highly efficient heat transfer fluids, supporting media for catalysts as well as electrochemical devices including supercapacitors, fuel cells, lithium batteries, photovoltaic cells, electrochemical mechanical actuators and electroplating (Handy, S. T., Chem. Eur. J. 9 2938-2944 (2003); Ding, J., et al., Chem. Mater. 15 2392-2398 (2003: Jensen, M. P. et al., J. Am. Chem. Soc. 125 15466-15473 (2003); Yang, C., et al., J. Phys. Chem. B, 107 12981-12988 (2003: Barisci, J. N., et al., Electrochem. Commun. 6 22-27 (2004; Wang, P., et al., J. Phys. Chem. B, 107 13280-13285 (2003)). Recently, reports for the use of ILs as lubricants for steels joints (Liu, W. M., et al., Tribology Letters 13 81-85 (2002: Wang, H. Z., et al., Wear 256 44-48 (2004: and Ye, C. F., et al., Wear, 253 579-584 (2002: show that the ILs exhibits excellent friction-reduction, antiwear properties, both in air and in vacuum, which are superior to phosphazene and perfluoropolyether.

Identifying and correcting emissions from high-polluting vehicles requires small sensors working at high temperatures to monitor pollutants in exhaust gas or leaking fuels (Tsang et al., J. Phys. Chem. B, 2001, 105, 5737-5742; Kaltenpoth et al., Anal. Chem., 2003, 75, 4756-4765). High temperature gas sensing is conventionally achieved by using semi-conductive metal oxides, such as $SnO_2$ and $TiO_2$ (Dutta et al., J. Phys. Chem. B, 1999, 103, 4412-4422; Ikohura and Watson, The Stannic Oxide Gas Sensor, CRC Press: Boca Raton, Fla., 1994; Zhu et al., Anal. Chem., 2002, 74, 120-124). The resistance of metal oxides changes in the presence of organic vapors, CO or $H_2$. It takes relatively a long time to reach equilibrium for the sorption of analytes from gas phase onto the metal oxides, especially for porous materials. The dependency of the resistance of the metal oxides on the vapor concentration is not linear, which reduces the accuracy of quantitative analysis (Simon et al. J. Comb. Chem., 2002, 4, 511-515). Some metal oxides work only at temperatures higher than a "switch on" value, e.g. >700° C. for $SrTiO_3$(Hu et al., J. Phys. Chem. B, 2004, 108, 11214-11218; Wang et al., J. Am. Chem. Soc., 2003, 125, 16176-16177; Dutta et al., Chem. Mater., 2004, 16, 5198-5204).

Rubbery polymers with low glass transition temperatures ($T_g$) have been used as coatings for detection of nonpolar or weakly polar organic vapors (Grate et al., *Anal. Chem.*, 1993, 65, 987A). The vapor sorption in rubbery polymers is reversible and equilibrium is attained rapidly (Grate et al., *Anal. Chem.*, 1993, 65, 987A; (a) Jarrett and Finklea, *Anal. Chem.*, 1999, 71, 353; (b) Shinar et al., *Anal. Chem.*, 2000, 72, 5981; (c) Zellers et al., *Anal. Chem.*, 1995, 67, 1092; (d) Patrash and Zellers, *Anal. Chem.*, 1993, 65, 2055). However, the mechanical properties of rubbery polymers strongly depend upon temperature (U. W. Gedde, *Polymer Physics*, Kluwer Academic Publ., Doedrecht, Netherlands, 1999). Most polymer materials with low $T_g$ are not stable at high temperatures. Therefore, applications of polymer materials for high temperature vapor sensing are limited. Furthermore, if the vapors cannot absorb on the materials, the large surface-area to volume ratio sensing materials, such as graphite ((a) Jarrett and Finklea, *Anal. Chem.*, 1999, 71, 353; (b) Shinar et al., *Anal. Chem.*, 2000, 72, 5981; (c) Zellers et al., *Anal. Chem.*, 1995, 67, 1092; (d) Patrash and Zellers, *Anal. Chem.*, 1993, 65, 2055) or oxides (Dutta et al., *J. Phys. Chem. B*, 1999, 103, 4412-4422; Ikohura and Watson, *The Stannic Oxide Gas Sensor*, CRC Press: Boca Raton, Fla., 1994; Zhu et al., *Anal. Chem.*, 2002, 74, 120-124) would not work for high temperature gas sensing.

U.S. Pat. No. 4,236,893 to Rice, U.S. Pat. No. 4,242,096 to Oliveira et al., U.S. Pat. No. 4,246,344 to Silver III, U.S. Pat. No. 4,314,821 to Rice, U.S. Pat. No. 4,735,906 to Bastiaans, and U.S. Pat. No. 6,087,187 to Wiegland et al. each teach using a piezoelectric sensor for the detection of an analyte in a liquid sample. U.S. Patent Application Publication Nos. 2003/0077222, 2003/0073133, 2003/0072710, 2003/0068273, 2003/0053950, and 2003/0049204, all to Leyland-Jones, discloses immunosensors which in particular embodiments have antibodies, Fab fragments, or scFv polypeptides immobilized on the surface thereof.

U.S. Patent Application Nos. 2002/0094531 to Zenhausern teach sensing probes such as a QCM for detecting a biological analyte of interest in gaseous, vapor, or liquid forms. The sensing probes are coated with various materials, such as polymers, ion exchange resins, porous silicon, silanes, thiols, and oxides. However ionic liquids are not taught as a coating for the sensing probes.

U.S. Patent Application Nos. 2002/0142477 to Lewis et al. teach organic vapor measurement using a polymer-coated quartz crystal microbalance. The quartz crystal microbalance crystals are coated with polymers including poly (ethylene-co-vinyl acetate) with 25% acetate (PEVA) and poly(caprolactone) (PCL) polymer films.

There is a need for improved devices which rely upon ILs.

OBJECTS

One of the objects is to provide a single sensor unit capable of both electrochemical and piezoelectric measurements using ionic liquid films, particularly for use as a gas sensor (or in a gas sensor system) to detect redox-active gaseous analytes such as explosive vapors.

It is an object to provide devices with bound ionic liquid films, particularly for use in piezoelectric gas sensors.

It is further an object to provide such piezoelectric gas sensors which are capable of detecting both polar and nonpolar organic vapors as well as common environmental gases (e.g., $CO_2$, $NO_2$). It is an object to provide devices where an ionic liquid film is bound to an exposed surface of a substrate.

It is still further an object to provide gas sensors which have a fast linear and reversible response.

These and other objects may become increasing apparent by reference to the following description.

SUMMARY

Gas sensors are of increasing interest due to their potential applications in ambient air monitoring, occupational health and safety, biomedical diagnostics, industrial process control, and security. Electrochemical (EC) sensors have historically proven to be very effective for measurement of airborne trace compounds. However, they are also known to suffer from interference and limited specificity. Similarly, piezoelectric gas sensors are very sensitive but are typically not very selective. To overcome these critical limitations of existing technology, an integrated sensor that combines electrochemical and piezoelectric transduction mechanisms into a single miniaturized platform has been developed. The piezoelectric electrodes for mass sensing and the electrochemical electrodes for amperometric detection were fabricated on a single quartz plate, allowing two-dimensional sensing via two orthogonal detection methods: quartz crystal microbalance (QCM) sorption and amperometric electrochemical reactivity. Simultaneous sensing with these two orthogonal methods provides additional selectivity to the sensor and significantly increases the accuracy of the detection at little or no power cost. This multidimensional sensing takes advantage of the unique properties of ionic liquids to realize both the electrolyte for electrochemical detection (e.g., amperometric) and the sorption material for piezoelectric QCM detection, enabling a single gas sensor with enhanced sensitivity, specificity, and stability.

Electrochemical amperometric sensors require the use of an electrolyte, an ionically conducting medium, to transport charge within the electrochemical cells, contact all electrodes effectively, and solubilize the reactants and products for efficient mass transport. Similarly QCM mass sensors require the use of a selective coating or film over the electrodes to absorb gas into the film and generate a mass change. Ionic liquids (ILs) satisfy the requirements for both the electrolytes and the selective sorption coatings, permitting two dimensional electrochemical and piezoelectric gas sensing from a single device. ILs have high ion conductivity, wide potential window (up to 5.5V), high heat capacity and good chemical and electrochemical stability. They have been explored as media in electrochemical devices including super capacitors, fuel cells, lithium batteries, photovoltaic cells, electrochemical mechanical actuators and electroplating [1-4]. A small amount of water moisture absorbed in ionic liquids has been shown to have little effect on the electrochemical behavior of ionic liquid electrolytes [2]. ILs have negligible vapor pressure and thus low risk of drying out of the electrolytes. ILs are stable at relative high temperature (up to 350° C.), so most volatile organic contaminates could be removed by increasing the temperature of the system. Moreover, due to the excellent thermal stability of ILs, the problem of fouling by organic compounds and water moisture could be easily minimized or eliminated by heating to regenerate the ionic liquid based sensors.

To validate the two-dimensional sensing approach, redox-active explosives with nitro ($-NO_2$) groups such as TNT were selected as target analytes because they have been used extensively to make homemade bombs. The increasing incidents and threats of terrorist attacks by improvised explosive devices have been the driving force to develop highly sensitive, specific and fast detection explosives sensor devices and systems. Many chemical sensing materials and detection devices for explosives detection have been developed [5-8].

The nitro (—NO$_2$) groups in most explosive compounds can be reduced electrochemically at a negative potential where most of aqueous electrolyte solutions are not stable [9-11]. However, when ionic liquids are used, the reductions of nitro compounds can be clearly observed and investigated without any decomposition of the ionic liquid electrolytes. A series of reports on amperometric detection of explosive materials has been published [12-26]. Direct sampling of explosives is very difficult because explosives are often being concealed. Most of the current techniques for explosive detection are based on the detection of explosive vapors because most organic nitro compounds, solid or liquid, have a measureable vapor pressure at room temperature. However, some explosive materials, such as 2,4,6-trinitrotoluene (TNT), have very low vapor pressure at room temperature. Mass produced TNT always has mono- or bi-substituted toluenes as impurities that are quite volatile at room temperature [27]. Therefore, detection of ethyl nitrobenzene (ENB) and dinitrotoluene (DNT) vapors as analogues of TNT and other explosives could be an effective alternative. Ionic liquid-based QCM sensors have been developed for detection of volatile organic compounds [28,29] including ENB and DNT. QCM/IL sensors have shown sensitivities as low as 115 ppm for methane at room temperature [30].

A QCM/IL sensor alone often cannot provide the selectivity needed for identification of any specific vapor analyte. Previously, QCM/IL sensor arrays were used for classification (identification) of volatile organic compound vapors, such as ethanol, benzene, or dichloromethane [28,29]. The electrochemical behavior of ENB and DNT was first investigated in bulk ionic liquid solutions. Then, QCM and electrochemical sensing methods were tested separately on a standard QCM device and a thin-layer electrochemical setup on glass slide. Finally, QCM electrodes and the electrodes for electrochemical measurement (e.g., amperometry) were fabricated together on a single piece of quartz to produce an integrated electrochemical quartz crystal microbalance (EQCM) chip. Detection of volatile ENB vapor was tested using both QCM and amperometric methods with this new integrated chip. The results demonstrate that the EQCM sensor chip performed excellently both as a QCM sensor and as an amperometric sensor. This integrated, two-dimensional sensing technology permits reduction or elimination of false positive or false negative results and significantly increases the accuracy of the detection. The integrated device permits miniaturization, effectively reducing the size and number of the parts required for electrochemical and QCM detection, and supports lab-on-chip analytical chemistry. Furthermore, ionic liquids are proven to be a unique material that satisfies the requirements of both detection methods, being a gas absorption material for QCM and a molten electrolyte for amperometry.

Piezoelectric and electrochemical measurements also can be combined in a single sensor apparatus, for example having the ability to perform both QCM and electrochemical impedance spectroscopy (EIS) measurements. The combination measurements can be performed on QCM electrodes with ionic liquids (e.g., ionic liquids combined with conductive polymers such as polyaniline to bind the ionic liquid to the sensor substrate). Similar to the above combination of QCM and amperometric methods, the orthogonal sensing capability provided by QCM/EIS using the unique characteristics of ionic liquids has the potential to significantly increase the detection accuracy.

The disclosure generally relates to an electrochemical sensor. The sensor generally includes: (a) a substrate having a first surface and a second surface on opposing sides of the substrate; (b) a first electrode over the first surface; (c) a second electrode over the first surface and spaced apart from the first electrode; (d) a third electrode over the first surface and spaced apart from the first electrode and the second electrode; and (e) an ionic liquid film over the first surface, the first electrode, the second electrode, and the third electrode; wherein the first electrode, the second electrode, and the third electrode are spaced apart to permit electrochemical measurement of an analyte absorbed in the ionic liquid film. Preferably, the sensor is capable of performing piezoelectric measurements, in which case: (i) the substrate comprises a piezoelectric material (e.g., quartz); (ii) the sensor further comprises (f) a fourth electrode over the second surface and substantially opposite the first electrode; and, (iii) the first electrode and the fourth electrode permit piezoelectric measurement of the analyte absorbed in the ionic liquid film. While the first electrode could be used to perform both electrochemical and piezoelectric measurements, a fifth electrode (i.e., distinct from the first electrode) can be included over the first surface such that the fourth and fifth electrodes are used to perform piezoelectric measurements. Additionally, a fifth electrode (i.e., distinct from the first electrode) can be included over the first surface such that the fourth and fifth electrodes are used to perform other electrochemical measurements (e.g., electrochemical impedance spectroscopy).

Various refinements to the sensor are possible. In an embodiment, the sensor further includes an intermediate adhesion layer between the first electrode and the first surface, between the second electrode and the first surface, between the third electrode and the first surface, and between the fourth electrode (when present) and the second surface. Alternatively, the adhesion layer is not included such that (i) the first electrode, the second electrode, and the third electrode are on the first surface; and (ii) the fourth electrode (when present) is on the second surface. In an embodiment, the sensor can include (f) a fourth electrode over the first surface and spaced apart from the first electrode, the second electrode, and the third electrode and (optionally) (g) a fifth electrode over the second surface and substantially opposite the first electrode, wherein the substrate comprises a piezoelectric material, and the first electrode and the fifth electrode permit piezoelectric measurement of the analyte absorbed in the ionic liquid film. In another embodiment, (i) the second electrode comprises a portion that at least partially surrounds a portion of the first electrode; and (ii) the third electrode comprises a portion that at least partially surrounds a portion of the second electrode. More particularly, such an embodiment can be characterized by (i) a first distance between the portion of the third electrode and the portion of the second electrode that is at least partially surrounded ranges from about 10 µm to about 200 µm (e.g., about 20 µm to about 100 µm, about 30 µm to about 70 µm); and (ii) a second distance between the portion of the third electrode and the portion of the first electrode that is at least partially surrounded is more than about 500 µm (e.g., ranging from about 500 µm to about 5000 µm, about 600 µm to about 3000 µm, about 800 µm to about 2000 µm). The sensor's electrode geometry can be alternatively characterized such that (i) the first electrode comprises a substantially disk-shaped portion; (ii) the second electrode comprises a substantially ring-shaped portion that (A) is positioned radially outwardly from the substantially disk-shaped portion of the first electrode and (B) at least partially surrounds the substantially disk-shaped portion of the first electrode; (iii) the third electrode comprises a substantially ring-shaped portion that (A) is positioned radially outwardly from the substantially ring-shaped portion of the second electrode and (B) at least partially surrounds the substantially ring-shaped portion of the second electrode; and (iv) the fourth electrode (when present) comprises a substantially disk-shaped portion that is substantially aligned with the substantially disk-shaped portion of the first electrode. In another embodiment of the sensor's electrode geometry, the (i) the first electrode comprises a substantially disk-shaped portion; (ii) the second electrode comprises a substantially arc-shaped portion that is positioned radially outwardly from the substantially disk-shaped portion of the first electrode; and, (iii) the third electrode comprises a substantially arc-shaped portion that (A) is positioned radially outwardly from the substantially disk-shaped portion of the first electrode and (B) is at substantially the same radial position as the arc-shaped portion of the second electrode.

Preferably, the ionic liquid film is formed from an ionic liquid having (i) a cation selected from the group consisting of ammonium cations, phosphonium cations, imidazolium cations (alkylated imidazolium cations more preferable), pyrrolidinium cations, pyridinium cations, and combinations thereof; and (ii) an anion selected from the group consisting of sulfonates, bisulfates, inorganic halogenated anions (more preferable), organic halogenated anions, and combinations thereof. The ionic liquid film can have any suitable thickness, for example ranging from about 60 µm to about 500 µm, about 80 µm to about 400 µm, about 100 µm to about 400 µm, or about 100 µm to about 200 µm. The ionic liquid film can be bound/immobilized or otherwise positioned on the sensor/substrate/electrode surfaces based on the surface tension of ionic liquid. In a refinement, the ionic liquid film is alternatively or additionally bound to the first surface, the first electrode, the second electrode, and the third electrode with a binding agent selected from the group consisting of a self-assembled monolayer, a polyelectrolyte, a conductive polymer, a polyionic liquid, a zwitterionic liquid, and combinations thereof. In another refinement, the sensor can include a second ionic liquid film over the second surface and any electrodes thereon, in which case the second ionic liquid film can be used to perform piezoelectric measurements (e.g., to detect, quantitate, and/or identify an analyte absorbed into the second ionic liquid film).

In another embodiment, an electrochemical piezoelectric sensor generally includes: (a) a piezoelectric quartz substrate having a first surface and a second surface on opposing sides of the piezoelectric quartz substrate; (b) a first conducting metallic electrode over the first surface, the first electrode comprising a substantially disk-shaped portion; (c) a second conducting metallic electrode over the first surface and spaced apart from the first electrode, the second electrode comprising a substantially ring-shaped portion that (A) is positioned radially outwardly from the substantially disk-shaped portion of the first electrode and (B) at least partially surrounds the substantially disk-shaped portion of the first electrode; (d) a third conducting metallic electrode over the first surface and spaced apart from the first electrode and the second electrode, the third electrode comprising a substantially ring-shaped portion that (A) is positioned radially outwardly from the substantially ring-shaped portion of the second electrode and (B) at least partially surrounds the substantially ring-shaped portion of the second electrode; (e) a fourth conducting metallic electrode over the second surface, the fourth electrode comprising a substantially disk-shaped portion that is substantially aligned with the substantially disk-shaped portion of the first electrode; and (f) an ionic liquid film over the first surface, the first electrode, the second electrode, and the third electrode; wherein (i) the first electrode, the second electrode, and the third electrode are spaced apart to permit electrochemical measurement of an analyte absorbed in the ionic liquid film, and (ii) first electrode and the fourth electrode permit piezoelectric measurement of the analyte absorbed in the ionic liquid film. In a refinement, the sensor further includes (g) a fifth conducting metallic electrode over the first surface and spaced apart from the first electrode, the second electrode, and the third electrode, the fifth electrode comprising a substantially ring-shaped portion that (A) is positioned radially outwardly from the substantially ring-shaped portion of the third electrode and (B) at least partially surrounds the substantially ring-shaped portion of the third electrode. The sensor also can include any of the further sensor refinements discussed above.

In another embodiment, a piezoelectric sensor generally includes: (a) a piezoelectric substrate (e.g., quartz) having a first surface and a second surface on opposing sides of the piezoelectric substrate; (b) a first electrode over the first surface; (c) a second electrode over the second surface and substantially opposite the first electrode; and, (d) an ionic liquid film immobilized on the first electrode (and optionally on the first surface); wherein the first electrode and the second electrode permit piezoelectric measurement of an analyte absorbed in the ionic liquid film. The ionic liquid film can be bound to the first surface and the first electrode with a binding agent selected from the group consisting of a self-assembled monolayer, a polyelectrolyte, a conductive polymer, a polyionic liquid, a zwitterionic liquid, and combinations thereof. The sensor can be configured to perform electrochemical measurements, in which case the sensor further comprises third, fourth, and fifth electrodes over the first surface and having the ionic liquid film immobilized thereon; wherein the third, fourth, and fifth electrodes are spaced apart from each other to permit electrochemical measurement of an analyte absorbed in the ionic liquid film. One of the third, fourth, and fifth electrodes can be the same as the first electrode (e.g., they share the same conducting material). The sensor can include any of the further sensor refinements discussed above.

Any of the foregoing electrochemical and/or piezoelectric sensor embodiments can be incorporated into an electrochemical and/or piezoelectric gas sensing system. In an embodiment suitable for voltammetry measurements, a system includes (a) one or more electrochemical and/or piezoelectric sensors according to any of the various embodiments (e.g., multiple sensors used to form an array, optionally with different sensors having different ionic liquids, ionic liquid film thicknesses, electrode configurations); (b) when the sensor is adapted to piezoelectric measurement, an AC voltage source electrically connected to (i) the first electrode as a piezoelectric sensing electrode and (ii) the fourth electrode as a piezoelectric contact electrode; and (c) when the sensor is adapted to electrochemical measurement, a DC voltage source (e.g., potentiostat) electrically connected to (i) the first electrode as an electrochemical reference electrode, (ii) the second electrode as an electrochemical working electrode, and (iii) the third electrode as an electrochemical counter electrode. In an embodiment suitable for impedance spectroscopy measurements, a system includes (a) one or more electrochemical and/or piezoelectric sensors according to any of the various embodiments (e.g., multiple sensors used to form an array, optionally with different sensors having different ionic liquids, ionic liquid film thicknesses, electrode configurations); (b) an AC voltage source electrically connected to (i) the first electrode as a piezoelectric sensing electrode and (ii) the fifth electrode as a piezoelectric contact electrode; and, (c) a variable frequency voltage or current source electrically connected to (i) the first electrode as an electrochemical working electrode, (ii) the second electrode as an electrochemical reference electrode, (iii) the third electrode as an electrochemical counter electrode; and (iv) the fourth electrode as an electrochemical counter electrode. When the system includes a plurality of sensors, each of the sensors preferably is electrically connected to an AC voltage source and/ or a DC/variable frequency voltage or current source.

Any of the foregoing electrochemical piezoelectric sensor/ system embodiments can be used in a method of analyzing a gaseous sample for the presence or absence of an analyte (e.g., one or more organic vapor species, one or more explosive vapor species, one of more common environmental gases such as $CO_2$, CO, $NO_2$, etc.). The method generally includes: (a) exposing any of the foregoing sensors to a gaseous sample, thereby absorbing at least a portion of any analyte present in the gaseous sample into the ionic liquid film of the sensor; (b) applying a first voltage across the first electrode and the fourth electrode, and measuring a resulting change in a resonant frequency in the piezoelectric substrate; (c) applying a second voltage across the first electrode and the second electrode, and measuring a resulting voltammetric current trace across the second electrode and the third electrode; and, (d) determining the presence of the analyte absorbed into the ionic liquid film by at least one of the resonant frequency change and the voltammetric current trace. Preferably, the method further includes (e) identifying the analyte in part (d) by one or more characteristic peaks in the voltammetric current trace. Quantitative analysis also can be performed, for example by additionally ($f_1$) calculating the concentration of the identified analyte in part (e) with the one or more characteristic peaks in the voltammetric current trace (e.g., by the amplitude/magnitude of a characteristic peak) and/or ($f_2$) calculating the concentration of the identified analyte in part (e) with the resonant frequency change (e.g., by the amplitude of a positive frequency change). In an embodiment, (i) the first voltage is an AC voltage that permits piezoelectric measurement of an analyte absorbed in the ionic liquid film; and, (ii) the second voltage is a DC voltage that permits electrochemical measurement of the analyte absorbed in the ionic liquid film. In another embodiment, the first voltage and the second voltage are applied simultaneously or quasi-simultaneously (e.g., in alternating succession). In yet another embodiment, part (b) of the process is performed continuously until the resonant frequency change indicates the presence (or potential presence) of the absorbed analyte, and then performing part (c) of the process. Preferably, the second voltage is applied in a time-dependent manner to perform one or more of cyclic voltammetry (CV), square wave voltammetry (SWV), and differential pulse voltammetry (DPV). In various embodiments, the analyte can include particular species of interest detectable by the sensor, including, for example, (a) one or more nitro-containing ($-NO_2$) organic and/or explosive vapor species/compounds, (b) one or more nitro-alkylaromatic compounds, and/or (c) one or more of ethyl nitrobenzene and isomers thereof, dinitrobenzene and isomers thereof, and combinations thereof.

Any of the foregoing electrochemical piezoelectric sensor/ system embodiments can be used in an alternate method of analyzing a gaseous sample for the presence or absence of an analyte (e.g., one or more organic vapor species, one or more explosive vapor species, one of more common environmental gases such as $CO_2$, CO, $NO_2$, etc.). The method generally includes: (a) exposing the sensor of claim 7 to a gaseous sample, thereby absorbing at least a portion of any analyte present in the gaseous sample into the ionic liquid film; (b) applying a first voltage across the first electrode and the fifth electrode, and measuring a resulting change in a resonant frequency in the piezoelectric substrate; (c) applying a second voltage or current across the first electrode and the second electrode, and measuring a resulting impedance spectrum of the sensor; and, (d) determining the presence of the analyte absorbed into the ionic liquid film by at least one of the resonant frequency change and the impedance spectrum. Preferably, (i) the first voltage is an AC voltage that permits piezoelectric measurement of an analyte absorbed in the ionic liquid film; and, (ii) the second voltage or current is a variable frequency voltage or current that permits electrochemical measurement of the analyte absorbed in the ionic liquid film. In a refinement, the method further includes (e) identifying the analyte in part (d) by one or more characteristic patterns in the impedance spectrum and (optionally) ($f_1$) calculating the concentration of the identified analyte in part (e) with the one or more characteristic patterns in the impedance spectrum and/or ($f_2$) calculating the concentration of the identified analyte in part (e) with the resonant frequency change. In an embodiment, the method can include performing parts (b) and (c) simultaneously. In another embodiment, the method can include performing part (b) continuously until the resonant frequency change indicates the presence of the absorbed analyte and then performing part (c).

The present disclosure provides a device which comprises: a substrate with an exposed surface; and an ionic liquid film which is bound to the exposed surface so as to enable the ionic liquid to solvate an organic chemical which would be solvated by an unbound film of the ionic liquid. In further embodiments of the device, the ionic liquid film is phosphonium dodecylbenzene-sulfonate. In still further embodiments, the phosphonium dodecylbenzene-sulfonate is $P_{6,6,6,14}DBS$. In further embodiments, the ionic liquid film is bound to the surface by means of a self-assembled monolayer (SAM). In still further embodiments, the self-assembled monolayer (SAM) comprises carboxylic acid terminal groups or pyridine terminal groups. In further embodiments of the device, the ionic liquid film is bound to the surface by means of one or more polyelectrolyte or conductive polymer on the surface. In some embodiments, the conductive polymer is polyaniline. In still further embodiments, the ionic liquid film is bound to the surface by means of one or more polyionic or zwitterionic liquids. In some embodiments, at least one of the zwitterionic liquids comprise imidazolium, tetraalkylammonium or tetraalkylphosphonium groups. In some embodiments, the zwitterionic liquid further comprises sulfonate groups. In further embodiments, the organic chemical is methane.

The present disclosure provides a method of solvating an organic sample comprising: providing a device which comprises a substrate with an exposed surface; and an ionic liquid film which is bound to the exposed surface so as to enable the ionic liquid to solvate an organic chemical which would be solvated by an unbound film of the ionic liquid; and providing the organic chemical on the exposed surface of the ionic liquid film so that the film solvates the organic chemical. In further embodiments of the method, the ionic liquid is phosphonium dodecylbenzene-sulfonate. In still further embodiments, the phosphonium dodecylbenzene-sulfonate is $P_{6,6,6,14}DBS$. In further embodiments, the organic chemical is methane.

The present disclosure provides a gas sensor for determining the concentration of an organic vapor in a gaseous sample comprising: a quartz crystal microbalance having a transducer surface; and an ionic liquid film bound to the transducer surface of the quartz crystal microbalance, wherein when the organic vapor is present in the gaseous sample it is absorbed in the ionic liquid film on the transducer surface and changes a resonant frequency of the quartz crystal microbalance. In further embodiments, the ionic liquid film is bound to the surface by means of a self-assembled monolayer (SAM). In still further embodiments, the self-assembled monolayer (SAM) comprises carboxylic acid terminal groups or pyridine terminal groups. In further embodiments of the device, the ionic liquid film is bound to the surface by means of one or more polyelectrolyte or conductive polymer on the surface. In some embodiments, the conductive polymer is polyaniline. In still further embodiments, the ionic liquid film is bound to the surface by means of one or more polyionic or zwitterionic liquids. In some embodiments, at least one of the zwitterionic liquids comprise imidazolium, tetraalkylammonium or tetraalkylphosphonium groups. In some embodiments, the zwitterionic liquid further comprises sulfonate groups. In further embodiments, the organic chemical is methane.

The present disclosure provides a method of determining the concentration of an organic vapor in a gaseous sample comprising: providing a gas sensor for detecting the concentration of an organic vapor in a gaseous sample comprising a quartz crystal microbalance having a transducer surface; and an ionic liquid film bound on the transducer surface of the quartz crystal microbalance, wherein when the organic vapor is present in the gaseous sample it is absorbed in the ionic liquid film on the transducer surface and changes a resonant frequency of the quartz crystal microbalance; providing a reference gas to the transducer surface of the gas sensor; measuring a first reference frequency of the gas sensor; providing the gaseous sample to the transducer surface of the gas sensor; measuring a second resonant frequency of the gas sensor; subtracting the first resonant frequency from the second resonant frequency to provide a frequency change; and determining the concentration of the organic vapor in the gaseous sample by the frequency change. In further embodiments of the method, the ionic liquid is phosphonium dodecylbenzene-sulfonate. In still further embodiments, the phosphonium dodecylbenzene-sulfonate is $P_{6,6,6,14}DBS$.

The present disclosure provides a method of determining the concentration of an organic vapor in a gaseous sample comprising: providing a first gas sensor and a second gas sensor, the first and second gas sensors for detecting the concentration of an organic vapor in a gaseous sample, the sensors comprising a quartz crystal microbalance having a transducer surface, and an ionic liquid film bound on the transducer surface of the quartz crystal microbalance, wherein when the organic vapor is present in the gaseous sample it is absorbed in the ionic liquid film on the transducer surface and changes a resonant frequency of the quartz crystal microbalance; providing a reference gas to the first gas sensor; providing the gaseous sample to the second gas sensor; measuring a resonant frequency of the first sensor; measuring a resonant frequency of the second sensor; subtracting the resonant frequency of the first sensor from the resonant frequency of the second sensor to provide a frequency difference; and determining the concentration of the organic vapor in the gaseous sample by the frequency difference. In still further embodiments of the method, the ionic liquid is phosphonium dodecylbenzene-sulfonate. In still further embodiments, the phosphonium dodecylbenzene-sulfonate is $P_{6,6,6,14}DBS$.

The present disclosure provides a method of detecting an unknown organic vapor in a gaseous sample comprising: providing an array of gas sensors for detecting an organic vapor in a gaseous sample, each of the sensors comprising a quartz crystal microbalance having a transducer surface, and an ionic liquid film bound on the transducer surface, wherein when the organic vapor is present in the gaseous sample it is absorbed in the ionic liquid film on the transducer surface and changes a resonant frequency of the quartz crystal microbalance; providing a reference gas to the array; measuring a reference frequency of each of the sensors in the array; providing the gaseous sample to the array; measuring a resonant frequency of each of the sensors of the array; subtracting the resonant frequency of each of the sensors from the resonant frequency of each of the sensors to provide a frequency difference for each of the sensors of the array; and detecting the organic vapor in the gaseous sample by the frequency difference for each of the sensors in the array.

All patents, patent applications, government publications, government regulations, and literature references cited in this specification are hereby incorporated herein by reference in their entirety. In case of conflict, the present description, including definitions, will control.

Additional features of the disclosure may become apparent to those skilled in the art from a review of the following detailed description, taken in conjunction with the examples, drawings, and appended claims, with the understanding that the disclosure is intended to be illustrative, and is not intended to limit the claims to the specific embodiments described and illustrated herein.

BRIEF DESCRIPTION OF THE DRAWINGS

For a more complete understanding of the disclosure, reference should be made to the following detailed description and accompanying drawings wherein:

FIG. 1 shows structures and formulas of ILs.

FIG. 3A shows $\Delta f$ as a function of T of ionic liquid $P_{6,6,6,14}OMS$. FIG. 3B shows $\Delta f$ as a function of T of ionic liquid $P_{6,6,6,6}OCS$.

FIG. 14 illustrates a multichannel, monolithic QCM (MQCM) sensor array to give a four-channel output from the four QCM sensors set up as an array. FIGS. 14a-14c show the top surface of the sensor array (a), the bottom surface of the sensor array (b), and the sensor array with electrical connections to an external RQCM device (not shown). FIG. 14d shows the response to 10% ethanol, and FIG. 14e shows the response to 1%, 2%, 3%, 5%, and 7% $CH_2Cl_2$.

Figure 2:
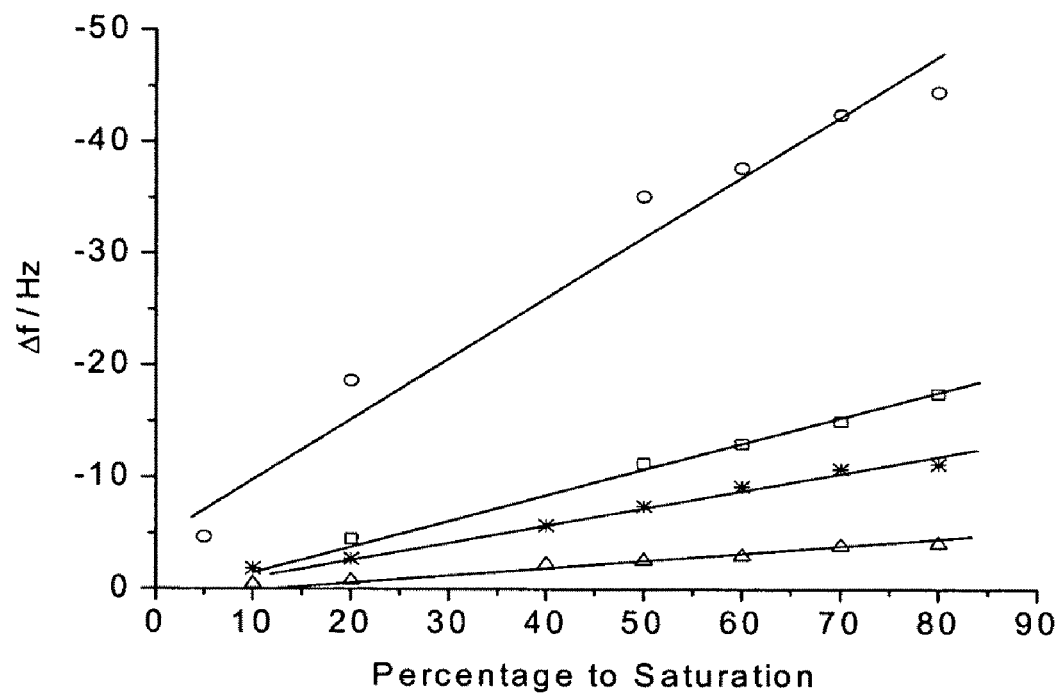
FIG. 2 is a graph showing frequency change vs. concentration of the IL/QCM sensor exposed to ethanol (square), heptane (triangle), benzene (star) and dichloromethane (circle) at 120° C.

While the disclosed compositions, apparatus, and methods are susceptible of embodiments in various forms, specific embodiments of the disclosure are illustrated in the drawings (and will hereafter be described) with the understanding that the disclosure is intended to be illustrative, and is not intended to limit the claims to the specific embodiments described and illustrated herein.

DETAILED DESCRIPTION

The present disclosure relates to an electrochemical piezoelectric sensor. The sensor includes a piezoelectric substrate, at least three electrodes over a first surface of the substrate, and another electrode over a second (opposing) surface of the substrate. An ionic liquid in the form of a film is adhered, bound, immobilized, or otherwise positioned over the substrate first surface and electrodes thereon. The ionic liquid film permits the absorption and detection of analytes from a gaseous sample, for example explosive vapors and/or explosive vapor species in the gaseous sample. Detection (optionally including analyte quantitation and qualitative identification) can be performed by both electrochemical and piezoelectric techniques using a single sensor. Systems incorporating and methods of using the electrochemical piezoelectric sensor also are disclosed.

In the present disclosure, methods are developed to immobilize one or more ionic liquids on preformed templates on electrode surfaces with controlled configurations so each film exhibits unique chemical and physical properties (e.g. defined surface morphology, porosity, hydrophobicity, wettability). The immobilized ionic liquid films are characterized by electrochemical techniques (e.g., QCM, Network Impedance analyzer, voltammetry/amperometry, impedance spectroscopy, potential step), ellipsometry, AFM and ATR and reflectance absorption infrared spectroscopy. The thermodynamics and kinetics of the modified IL film interactions are determined with various gas analytes including major vehicle emission pollutants and volatile organic compounds (e.g., $CO_2$, $CO$, $SO_2$, $NOR_x$, benzene, toluene, dichloromethane, ethanol, acetone, THF, DMF, etc.), and further including volatile explosive organic compounds (e.g., nitroaromatics such as ethyl nitrobenzene, dinitrotoluene). IL/QCM sensor arrays, high temperature IL/QCM gas sensors, and IL/EQCM sensors/arrays (i.e., IL/QCM sensors/arrays further adapted to electrochemical voltammetric measurements) are developed based on IL films (e.g., chemical-selective IL films), and pattern-recognition algorithms are developed for IL sensor arrays (e.g., where multiple ILs having different selectivities for different target analytes yield analyte-specific measurement signals from the array).

All patents, patent applications, government publications, government regulations, and literature references cited in this specification are hereby incorporated herein by reference in their entirety. In case of conflict, the present description, including definitions, will control.

The term "bound" as used herein means to hold or immobilize in place for the purpose of use of an ionic liquid (IL). In some embodiments, the IL is bound to a surface by means of electrostatic charge coupling, hydrogen bonding, physical adsorption, chemical adsorption, and/or surface tension. In some embodiments, a polymer (including, but not limited to a conductive polymer, such as polyaniline) can be formed from monomer structures having functional side groups. Thus, conductive polymer templates having additional functional groups can be generated for binding the IL to a surface. The functional groups can be used to immobilize ionic liquids with preferred orientation via various molecular interactions (i.e., hydrogen bond, p-p, dipolar, ionic. etc.) of ionic liquids and conductive polymer functional groups. Bound ionic liquids on a sensor/electrode substrate can be used for both piezoelectric measurements (e.g., QCM) and electrochemical measurements (e.g., voltammetry, impedance spectroscopy).

The term "QCM" as used herein refers to a quartz crystal microbalance. The QCM is used to measure a mass and/or viscosity that is applied to the QCM by means of the change in resonance frequency of a piezoelectric substrate (e.g., quartz crystal) when biased with an alternating voltage. The QCM is widely used as a transducer for sensing applications in solids, liquids and gases. For thin film that is elastically coupled as the whole quartz surface, the frequency change and mass change can be described as the Sauberey equation:

$$\Delta f = -\frac{2f_0^2 \Delta m}{A\sqrt{\mu_Q \rho_Q}}; \quad (1)$$

where $f_0$ is the resonance frequency of the crystal, A is the area of the deposit, $\mu_Q$ is the shear modulus of the quartz and $\rho_Q$ is its density. For thicker viscoelastic films, the thickness of the viscoelastic film is characterized by the penetration depth $\delta$ which characterizes the viscous attenuation of the shear wave amplitude by the bulk fluid. For a fluid of density $\rho_1$ and viscosity $\eta_1$, the shift of resonant frequency due to damping in a fluid is $$\Delta f = -f_0^{3/2} \sqrt{\frac{\eta_l \rho_l}{\pi \mu_Q \rho_Q}} \quad (2)$$

Figure 45:
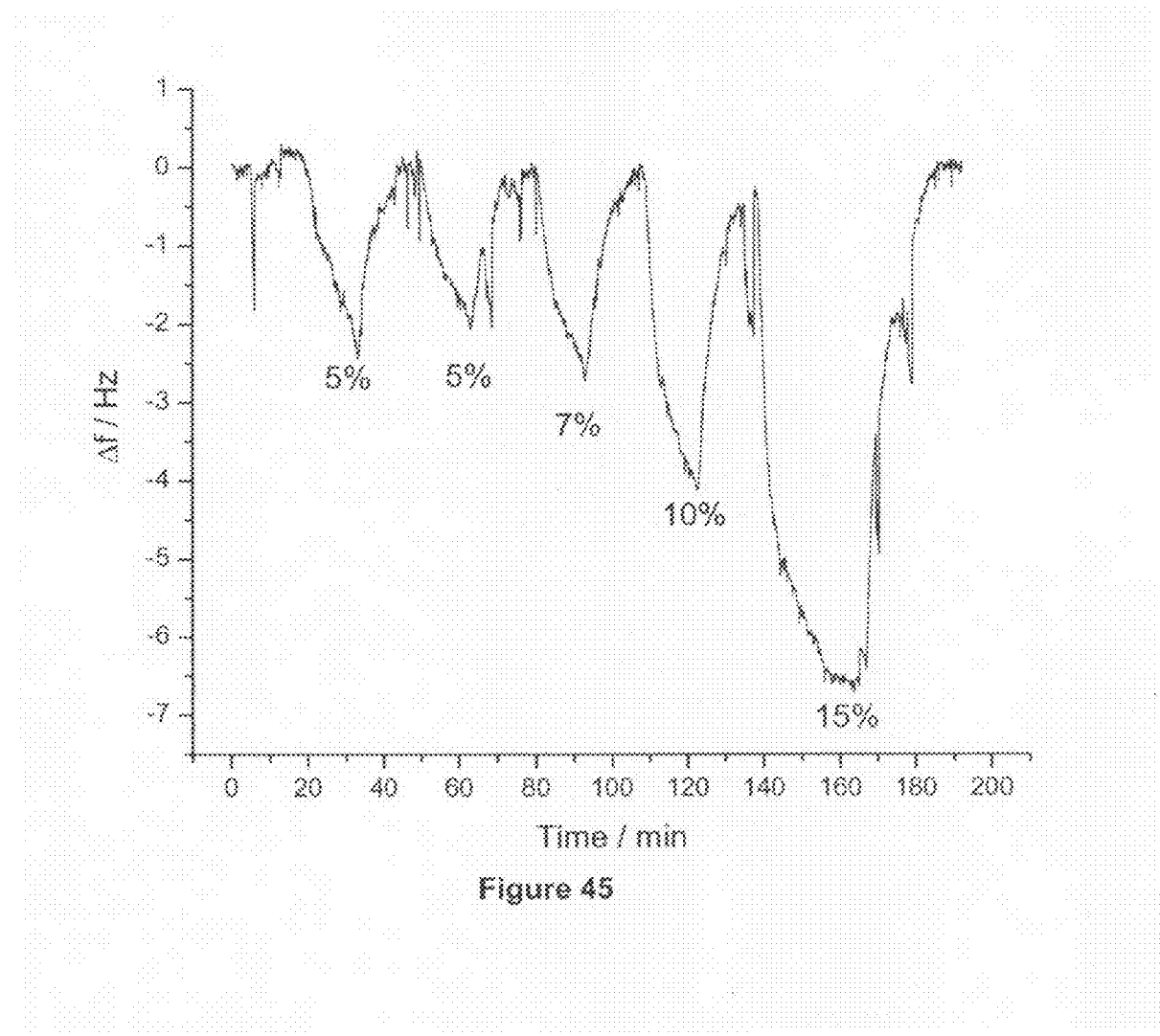
FIG. 45. Baseline-adjusted sensorgram of ENB with different concentrations on QCM electrode having a thin-film $BMIBF_4$ coating.
Figure 46A:
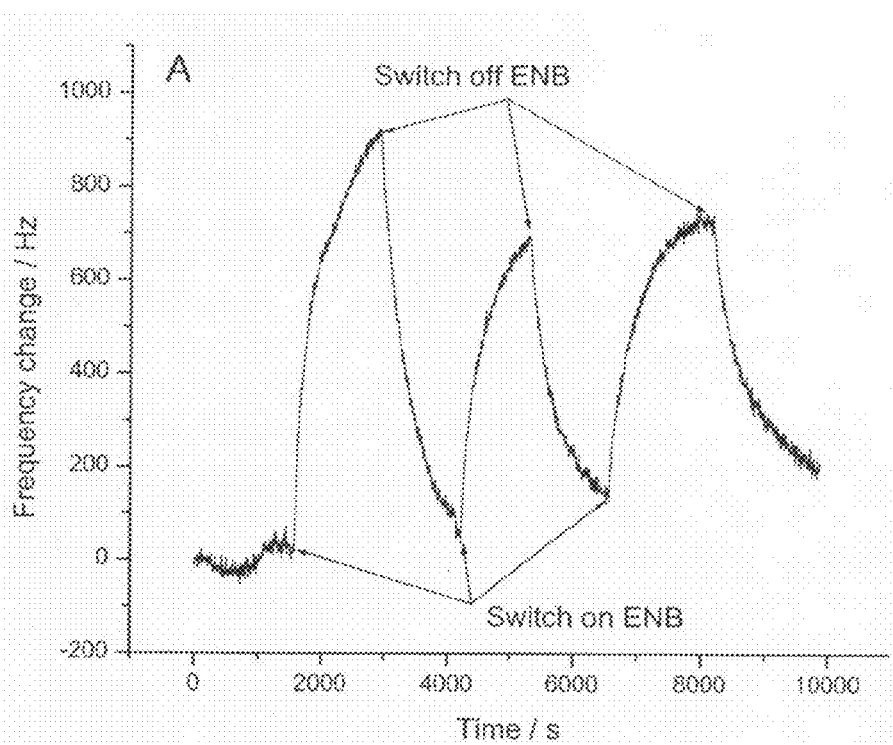
FIG. 46. Time-dependent sensorgram on the EQCM electrode resulting from the cyclical feeding of nitrogen and ENB-saturated nitrogen to the EQCM electrode (A), and resulting SWVs on the EQCM electrode (B).

For a thicker ionic liquid film, when gas solute is dissolved in the ionic liquids, it will lead to decrease of viscosity of ionic liquid on the QCM, which will result in an increase of frequency according to equation (2) (e.g., as shown in FIG. 46A). On the contrary, when ionic liquid is very thin and strongly coupled to the QCM surface, the gas analyte will be adsorbed in the QCM which will lead to an increase of mass and a decrease of frequency according to equation (1) (e.g., as shown FIG. 45).

Some examples of quartz crystal microbalance devices that can be used in the present disclosure include QCM devices available from Maxtek Inc. of Santa Fe Springs, Calif. Other QCM devices which can be used in the present disclosure are described in U.S. Pat. No. 4,236,893 to Rice, U.S. Pat. No. 4,242,096 to Oliveira et al., U.S. Pat. No. 4,246,344 to Silver Ill, U.S. Pat. No. 4,314,821 to Rice, U.S. Pat. No. 4,735,906 to Bastiaans, U.S. Pat. No. 5,314,830 to Anderson et al., U.S. Pat. No. 5,932,953 to Drees et al., and U.S. Pat. No. 6,087,187 to Wiegland et al., U.S. Pat. No. 6,890,486 to Penelle, U.S. Pat. No. 6,848,299 to Paul et al., U.S. Pat. No. 6,706,977 to Cain et al., U.S. Pat. No. 6,647,764 to Paul et al., U.S. Pat. No. 6,492,601 to Cain et al., U.S. Pat. No. 6,439,765 to Smith, U.S. Pat. No. 6,190,035 to Smith, U.S. Pat. No. 6,106,149 to Smith, U.S. Pat. No. 5,885,402 to Esquibel, U.S. Pat. No. 5,795,993 to Pfeifer et al., U.S. Pat. No. 5,706,840 to Schneider, U.S. Pat. No. 5,616,827 to Simmermon et al., U.S. Pat. No. 5,484,626 to Storjohann et al., U.S. Pat. No. 5,282,925 to Jeng et al., U.S. Pat. No. 5,233,261 to Wajid, U.S. Pat. No. 5,201,215 to Granstaff et al., U.S. Pat. No. 4,999,284 to Ward et al., and U.S. Pat. No. 4,788,466 to Paul et al. Examples of control circuitry for quartz crystal microbalances and methods for detecting materials using piezoelectric resonators are described in U.S. Pat. No. 5,117,192 to Hurd and U.S. Pat. No. 5,932,953 to Drees et al. Some methods which have been used to attach substances to surfaces such as the receptor surfaces of the QCM are described in U.S. Pat. No. 6,475,809 to Wagner et al., U.S. Pat. No. 6,475,808 to Wagner et al., U.S. Pat. No. 6,368,877 to Zhang et al., U.S. Pat. No. 6,319,674 B1 to Fulcrand et al., and U.S. Pat. No. 5,622,826 to Varma, and Yang et al., Nature Materials 1: 253-257 (2002). Each of the above references is hereby incorporated herein by reference in its entirety.

The term "organic vapor" as used herein refers to gaseous phase organic molecules. The term encompasses both polar organic molecules (including, but not limited to ethanol and dichloromethane) and nonpolar organic molecules (including, but not limited to heptane and benzene).

The term "environmental gas" as used herein refers to gaseous phase molecules that can be present in the environment (e.g., ambient indoor or outdoor air) and can be indicative of industrial pollution, environmental hazards, and/or health hazards. Examples of such target gaseous phase molecules for detection include $CH_4$, CO, $CO_2$, NO, $NO_2$, $SO_2$, $O_3$ (ozone), and $CH_2O$ (formaldehyde).

The term "explosive vapor" as used herein refers to gaseous phase organic molecules that are themselves explosive (i.e., chemically/energetically unstable and capable of sudden expansion upon ignition or other initiation to release heat and to create large changes in pressure) or are common co-constituents of explosive materials. The positive detection of one or more common co-constituents of an explosive material can be used to conclude that the explosive material is present in or near the sampled material. A QCM can detect essentially any analyte/explosive vapor that can adsorb and/or dissolve on an ionic liquid coating. Explosive vapors suitable for electrochemical detection include those with redox-active functional groups, for example including nitro groups, hydroxyl groups, carbonyl groups, amines/amino groups, and others. Nitro-containing ($—NO_2$) organic compounds are particularly suitable for electrochemical detection. Preferably, the detectable explosive vapor species are relatively volatile at room temperature such that they have high enough vapor pressures under normal conditions to significantly vaporize and enter the atmosphere. The higher the vapor pressure, the easier to detect as the concentration of the analyte will be high. A particularly relevant class of explosive vapors include nitroaromatic and/or nitro-alkylaromatic compounds (e.g., mono- and/or di-nitro aromatics/alkylaromatics). Common alkylaromatics have aromatic cores (e.g., substituted benzene, substituted naphthalene) with one or more alkyl groups (e.g., one or two alkyl groups; alkyl groups having 1 to 4 carbon atoms), for example including toluene, ethylbenzene, and/or xylene. Representative species of such compounds include the various isomers of ethyl nitrobenzene and/or dinitrotoluene, which can be both themselves explosive and are representative co-constituents of common, yet less volatile explosive materials such as trinitrotoluene (TNT). Other possible nitro-containing explosive compounds can include nitroglycerin, nitrocellulose, cyclotrimethylenetrinitramine (RDX), Pentaerythritol tetranitrate (PETN), 1,3,5,7-tetranitro-1,3,5,7-tetrazocane (HMX). Different ionic liquids have different affinities for target analytes, so the EQCM technique can detect most if not all gaseous compounds with targeted selection of IL coating materials using a sensor array.

The term "voltammetry" as used herein refers to electroanalytical/amperometric methods used to characterize an analyte in a medium (e.g., organic/explosive or other gaseous molecules that have been absorbed/solvated in an ionic liquid medium). Information about the analyte is obtained by applying a voltage potential across the medium (e.g., across a working electrode and a reference electrode) and by measuring the resulting current through the medium (e.g., across the working electrode and a counter electrode). Representative forms of voltammetry used herein include Cyclic Voltammetry (CV), Square Wave Voltammetry (SWV), and Differential Pulse Voltammetry (DPV). In CV, the potential is cyclically ramped upwardly and downwardly at a specified scan rate and with a defined period. In SWV, the potential is the superposition of a linear upward ramp (having a specified scan rate) and a square wave (having a specified amplitude and period). In DPV, the potential is ramped upwardly at a specified scan rate and periodic voltage pulses are superimposed upon the linear ramp.

The term "electrochemical impedance spectroscopy" (EIS) as used herein refers to an electroanalytical methods used to characterize an analyte in a medium (e.g., organic/explosive or other gaseous molecules that have been absorbed/solvated in an ionic liquid medium, where the ionic liquid medium can be immobilized with a chemical means such as a conductive polymer). The technique involves the measurement of the impedance of a system in response to cyclic electrochemical perturbations (e.g., alternating potentials or currents) over a range of frequencies. The results are generally expressed graphically in a Bode plot or a Nyquist plot.

Ionic Liquids

The term "ionic liquid" or "IL" as used herein generally refers to a liquid salt consisting solely of ions. The term encompasses room-temperature ionic liquids which melt at or close to room temperature (e.g., about 15° C. to about 40° C., or 20° C. to about 30° C.), and typically they are salts whose melting point is below approximately 100° C. Preferably the ionic liquids have negligible vapor pressure and have high thermal stability. The term ionic liquid (IL) encompasses liquids having organic cations and anions. The ILs typically comprise bulky asymmetric organic cations such as 1-alkyl-3-methylimidazolium, 1-alkylpyridinium, N-methyl-N-alkylpyrrolidinium or ammonium ions and a wide range of anions. Many ionic liquids are phosphonium salts. Phosphonium salts are more thermally stable than the corresponding ammonium salts and imidazolium salts, however any can be used in the present disclosure. Examples of some ionic liquids useful for the present disclosure include, but are not limited to, those ILs listed herein and those described in U.S. Pat. No. 6,852,229 to Mehnert et al., U.S. Patent Application Publication No. 2003/0204041 to Laas et al., U.S. Patent Application Publication No. 2004/0054231 to Abbott et al., U.S. Patent Application Publication No. 2004/0262578 to Wasserscheid et al., and U.S. Patent Application Publication No. 2005/0005840 to Bonrath et al. hereby incorporated herein by reference in their entirety.

More generally, the IL cations can include ammonium, phosphonium, imidazolium, pyrrolidinium, and/or pyridinium cations substituted with one or more hydrocarbon residues (e.g., alkyl groups) preferably having 1 to 20 carbon atoms. Suitable ammonium cations include $[NR_4]^+$, where R represents independently selected alkyl groups (e.g., $C_1$ to $C_{10}$, $C_3$ to $C_{10}$, $C_3$ to $C_8$, including linear and/or branched (e.g., isopropyl) groups). Suitable phosphonium cations include $[PR_4]^+$, where R represents independently selected alkyl groups (e.g., $C_2$ to $C_{20}$, $C_4$ to $C_{16}$). Suitable imidazolium cations include $[ImR_2]^+$, where Im represents an imidazole core and R represents independently selected alkyl groups (e.g., $C_1$ to $C_6$, $C_1$ to $C_4$) substituted at the 1- and 3-nitrogen positions of the imidazole core. Suitable pyrrolidinium cations include $[PylR_2]^+$, where Pyl represents a pyrrolidine core and R represents independently selected alkyl groups (e.g., $C_1$ to $C_{10}$, $C_1$ and $C_3$ to $C_{10}$) substituted at the 1-nitrogen position of the pyrrolidine core. Suitable pyridinium cations include $[PyrR]^+$, where Pyr represents a pyridine core and R represents an alkyl group (e.g., $C_2$ to $C_{10}$, $C_3$ to $C_8$) substituted at the 1-nitrogen position of the pyridine core. Similarly, the IL anions generally can include sulfonates (e.g., $[CF_3SO_3]^-$, $[C_3H_7SO_3]^-$, $[C_4H_9SO_3]^-$, $[C_4F_9SO_3]^-$, other alkyl sulfonates, other fluorosulfonates), bisulfates, inorganic halogenated anions (e.g., $[PF_6]^-$, $[BF_4]^-$), and/or organic halogenated anions (e.g., $[N(CF_3SO_2)_2]^-$, $[N(CF_3CF_2SO_2)_2]^-$). The sulfonate is preferably coupled to a hydrocarbon residue, for example having 1 to 20 carbon atoms and optionally including halogens. Such hydrocarbon residues can generally include aliphatic (e.g., alkyl) groups, cyclic (e.g., cycloalkyl) groups, aromatic (e.g., phenyl) groups, and/or combinations thereof (e.g., an alkylphenyl sulfonate).

This disclosure relates to the design and control of the molecular character of the ionic liquids on electrode surface for their applications in gas sensing, especially their application in sensor arrays and high temperature sensing for volatile organic and automobile tailpipe emission exhaust. High-temperature gas sensors are described in Zeng et al. U.S. Pat. No. 7,464,580, which is incorporated herein by reference in its entirety. A great deal of attention has been given to imidazolium ionic liquids which consist of halogen containing anions such as $[AlCl_4]^-$, $[PF_6]^-$, $[BF_4]^-$, $[CF_3SO_3]^-$, or $[N(CF_3SO_2)_2]^-$. For many technical applications, the presence of halogen atoms in the imidazolium ionic liquid can cause concerns if the hydrolytic stability of the anion is poor (e.g. for choroaluminate and hexafluorophosphate systems) or if a thermal treatment of the spent ionic liquid is desired. In some embodiments of the disclosure, phosphonium ionic liquids with alkanesulfonate and alkylbenzenesulfonate anions are preferable (Robertson, A. J., et al., WO 2002079212; and Bradaric, C. J., et al., in Industrial preparation of Phosphonium Ionic Liquids, ACS symposium Series 856, Ionic Liquids as Green Solvents, Progress and Prospects, R. D. Roger and K. R. Seddon Edt. American Chemical Society (2003); and Wasserscheid, P., et al., in New Ionic Liquids Based on Alkylsulfate and Alkyl Oligoether Sulfate Anions: Synthesis and Applications, ACS symposium Series 856, Ionic Liquids as Green Solvents, Progress and Prospects, R. D. Roger and K. R. Seddon Ed., American Chemical Society, (2003)). They possess high hydrolytic and thermal stability and acceptable viscosity. Very few investigations of this type of ILs have been reported in the literature. Imidazolium ionic liquids with non-halogen anions are provided for gas sensing.

FIG. 1 shows a table with structures and formulas of ILs. $BmiBF_4$, $bmiN(SO_2CF_3)_2$ and $hpPF_6$ were prepared following literature procedures, which are based on the metathesis of the corresponding imidazolium chlorides with appropriate salts (Wilkes, J. S., et al., J. Chem. Soc., Chem. Commun., 965 (1992); Bonhote, P., et al., Inorg. Chem., 35, 1168 (1996)). Water-immiscible ionic liquids, such as, bbiN $(SO_2CF_3)_2$ and $bbiPF_6$, were prepared based on a process known as "one-port synthesis of ionic liquids" (Ren, R. X., et al., WO 0294883 (2002); Ren, R. X., in Green synthesis of Ionic Liquids for Green Chemistry, Chapter 6 in the American Chemical Society Symposium Series #865 Ionic Liquids as Green Solvents: Progress and Prospects, American Chemical Society: Washington, D.C., pp. 70-81 (2003)). By mixing aqueous formaldehyde with two equivalent of 1-butylamine, hexafluorophosphoric acid, or bis(trifluoromethanesulfon) imide and aqueous glyoxal solution, the hydrophobic ionic liquid (lower layer) thus formed can be separated directly from the reaction mixture (Ren, R. X., et al., WO 0294883 (2002)). Sulfonate ionic liquids with various cations were all made via alcohol-to-alkyl halide conversion method, which is also a one-pot synthesis of ionic liquids (Ren, R. X., et al., WO 0351894 (2003)). By using primary alcohols (ROH), suitable acids (HA), the 1,3-dialkylmidazolium halides, pyridinium halides, tetraalkylammonium halides and tetraalkylphosphonium halides (all designated as $Q^+X^-$) can be converted to the new ionic liquids ($Q^+A^-$) with the anions being the conjugated bases of the acids used.

In FIG. 1, $N_{l,m,n,j}$ and $P_{l,m,n,j}$ represent the tetraalkylammonium and the tetraalkylphosphonium respectively. The subscripted numbers, l, m, n and j represent the numbers of carbons in each alkyl substitutes. For example, $N_{7,7,7,7}$ is tetraheptylammonium. The anion, dodecylbenzenesulfonate ($SO_3$-Ph-$C_{12}H_{25}$), was also abbreviated as DBS in the text. bmi and bbi are 1-butyl-3-methylimidazolium and 1,3-dibutylimidazolium, respectively. bei and pmi are 1-butyl-3-ethyl-imidazolium and 1-propyl-3-methyl-imidazolium, respectively. hp and bp are hexylpyridinium and butylpyridinium, respectively.

The table of FIG. 1 lists over twenty ionic liquids, which have been synthesized. Besides using traditional metathesis methods for the synthesis of $BF_4^-$, $PF_6^-$, $(CF_3SO_2)_2N^-$ and phosphinate anion-based ILs, a safer, more efficient and more environmentally friendly ("green") method for synthesis of bisulfate, alkanesulfonate and alkylbenzenesulfonate ionic liquids has been developed (Hsieh, M., et al., Anal. Chem., 76, 1885-1895 (2004)). This novel, innovative technology eliminates the shortcomings in the previously widely used methods of making ionic liquids via anion metathesis approaches which utilize conventional organic solvents and generate aqueous and solid wastes, and have technical difficulty in industrial scale-up. The extension of this technology will be directed at the synthesis of functionalized ionic liquids. Ionic liquids in FIG. 1 are now commercially available through IL-TECH. Other vendors for ILs are Cytec Inc., BASF and Degussa's Oligomers & Silicones.

EXAMPLE 1

QCM Sensor Array

An IL gas sensor at room and high temperatures (Chemical Communication, 2005, 2277-2279) has been described. Ionic liquids have high thermal stability (e.g. typical decomposition temperature is about 350° C. (by TGA) (Zhang, Z., et al., in EPD Congress (2002), P. R. Taylor, ed.; TMS, Warrendale Pa., p. 1999 (2002); Ngo, H. L., et al., Thermochim. Acta, 97, 357-358 (2000); Bonhote, P., e6 al., Inorg. Chem. 35, 1168-1178 (1996); Holbrey, J. D., et al., J. Chem. Soc., Dalton Trans. 2133 (1999); Takahashi, S., et al., Plasmas & Ions, 2, 91-105 (1999)). Reports also show that ionic liquids are able to protect the monellin from thermal degradation. The inventors have demonstrated both tetraalkylphosphonium and tetraalkylammonium IL thin films show enhanced sensitivity and selectively to the organic vapors (ethanol, dichloromethane, heptane or benzene) at room temperature and elevated temperatures as high as 200° C. when comparing to a bare gold electrode.

Figure 3A:
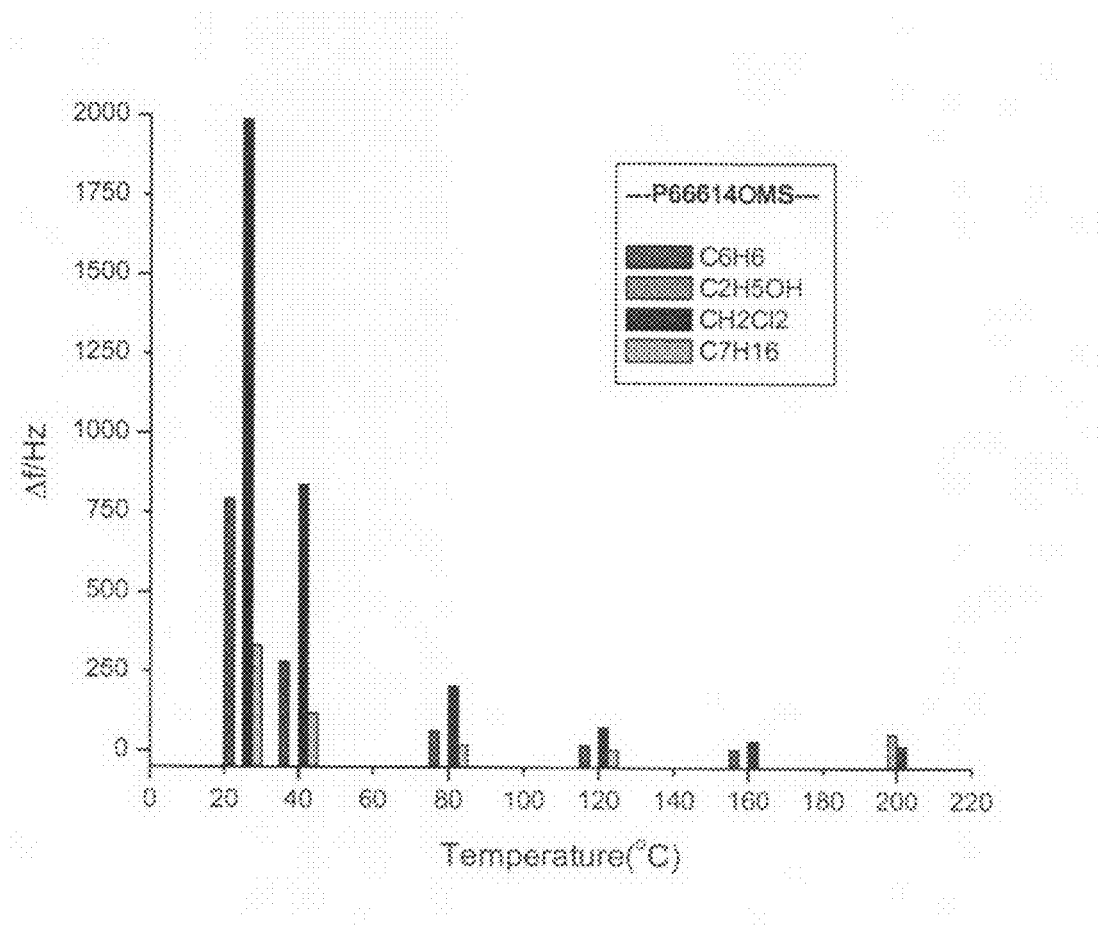
FIGS. 3A and 3B are graphs showing the frequency changes of the IL/QCM sensors exposed to 80% ethanol, heptane, benzene and dichloromethane at various temperatures.
Figure 3B:
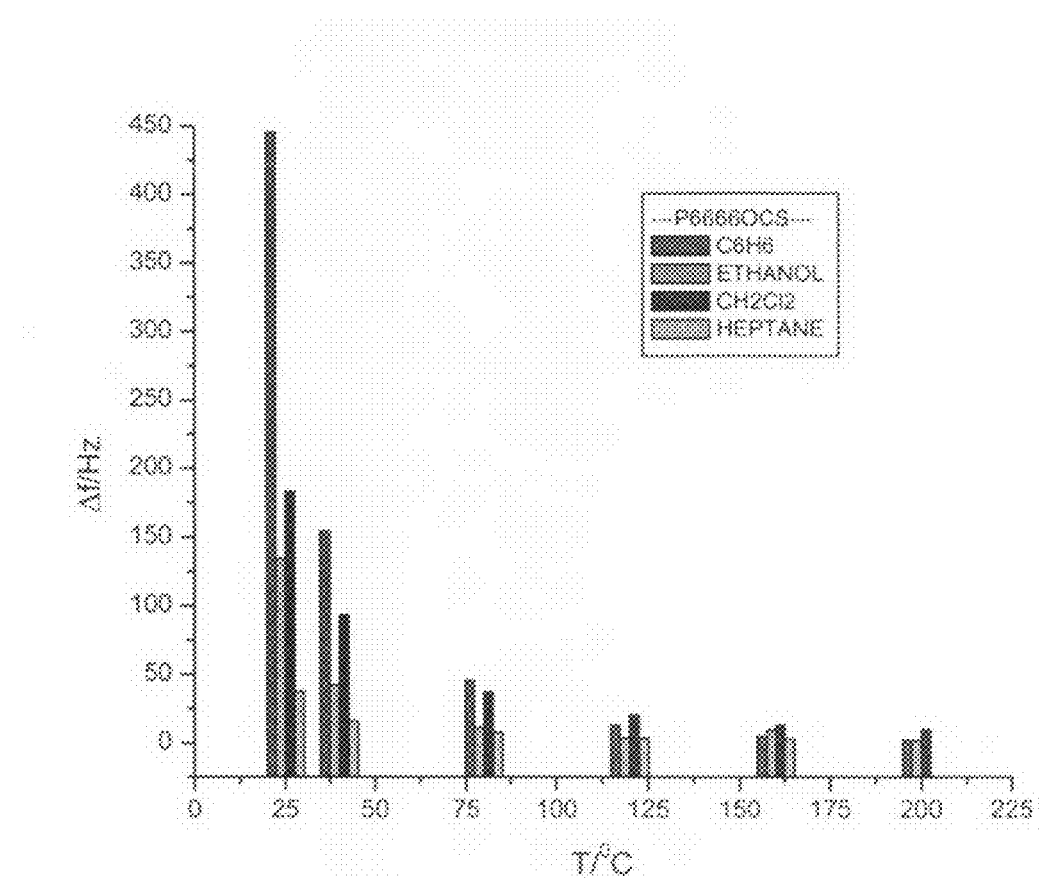

FIG. 2 shows the linear relationship of the frequency changes and the concentrations of vapor were obtained over the 0% to 100% saturation vapor pressure range at 120° C. for all the organic vapors tested. The detection limit could reach as low as 5% (e.g. 7 mg/L for ethanol). When the system was cooled down to 24° C., the IL/QCM sensor gave reproducible response at 24° C. again indicating high stability and reversibility. This procedure has also been used to remove the volatile impurity in the ionic liquid coatings. IL sensors offer significant advantages over conventional metal oxide sensors for high temperature industrial sensing applications. FIGS. 3A and 3B show the temperature dependence of the sensors' response to various vapors with two different ILs. The sensitivity reduced with the increase of temperature. However, until 200° C., the sensors kept relative strong sensitivity.

Figure 4B:
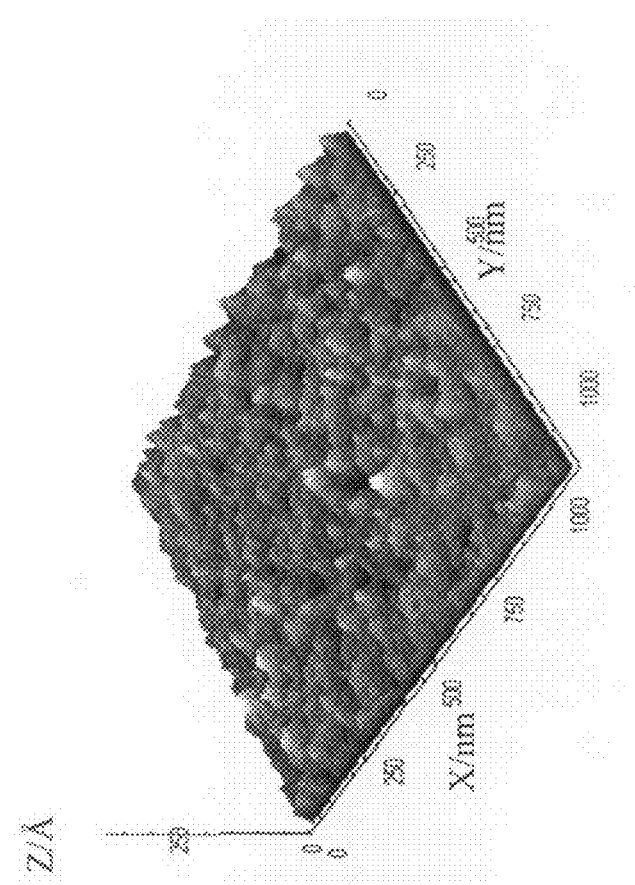
FIGS. 4A and 4B are AFM images of a polished Au QCM surface (FIG. 4A), and after it was modified with IL thin film (FIG. 4B). Contact mode.
Figure 4A:
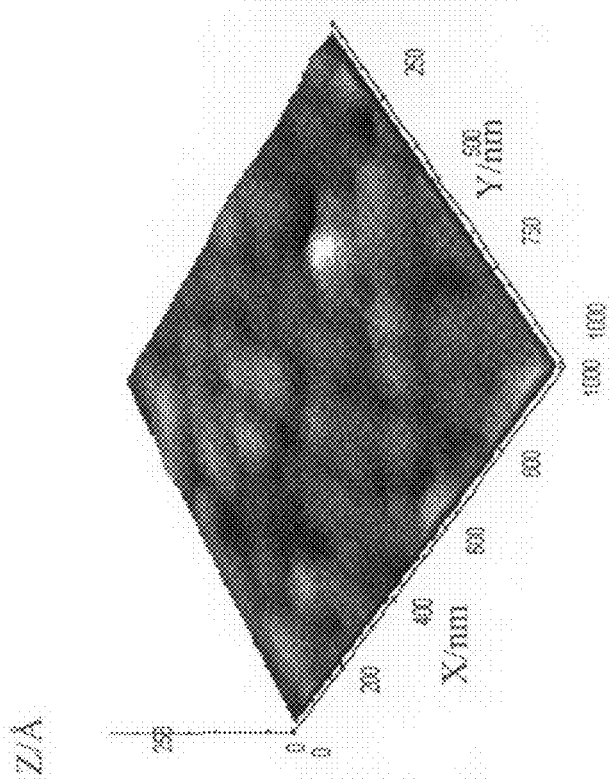
Figure 5:
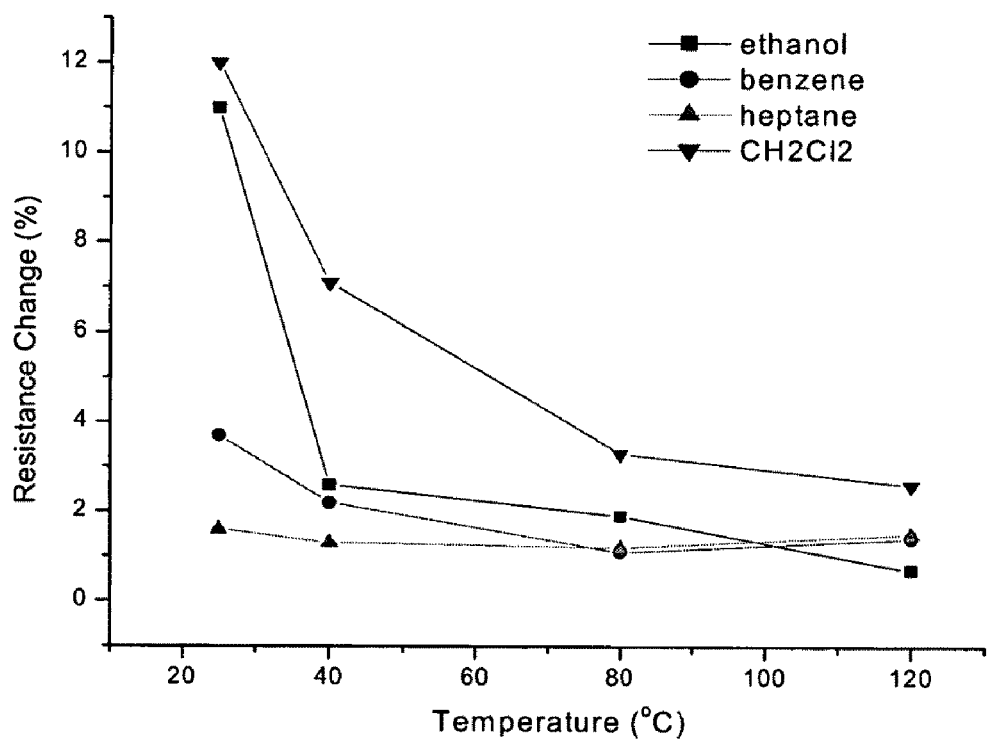
FIG. 5 is a graph showing $\Delta R$ % vs. temperature curve.

Early literature of ionic liquid gas sensors quantified the analyte concentration by viscosity induced frequency change (Wilkes, J. S., et al., J. Chem. Soc., Chem. Commun., 965 (1992); Bonhote, P., et al., Inorg. Chem. 35, 1168 (1996)). The sensor response is more complicated and can vary depends on experimental conditions. Mass detection by using Sauerbrey's equation (Ren, R. X., et al., WO 0294883 (2002); Ren, R. X., in Green Synthesis of Ionic Liquids for Green Chemistry, Chapter 6 in the American Chemical Society Symposium Series #865 Ionic Liquids as Green Solvents: Progress and Prospects, American Chemical Society: Washington, D.C., pp. 70-81 (2003)) (i.e. $\Delta f = -2\Delta m n f_0^2/(A(\mu_q \rho_q)^{1/2})$, where n is the overtone number, $\mu_q$ is the shear modulus of the quartz ($2.947 \times 10^{11}$ g/(cm sec$^2$), and $\rho_q$ is the density of the quartz (2.648 g/cm$^3$)) assumes the foreign mass is strongly coupled to the resonator. This condition can be met when the device is operating in the gas or the vacuum phase, the added mass binds tightly to the surface. Thin, rigid IL film was made so that the Sauerbrey equation is valid. Thin IL film was characterized by AFM (FIGS. 4A and 4B). Its rigidity is characterized by simultaneously measuring the damping resistance and the frequency change during the vapor detection experiments using MAXTEK RQCM. Table 1 summarizes the data of damping resistance (R) and its change ($\Delta R$ %; FIG. 5) for the four analytes tested at different temperatures. At room temperature, the $\Delta R$ % values are relatively large especially for ethanol (11%) and dichloromethane (12%), indicating a viscosity change of the film upon the adsorption of organic vapors. The $\Delta R$ % value decreases with increasing temperature. This is consistent with the thermodynamics i.e. the partition coefficient of gas molecules in liquid film reduces with increasing temperature. At 120° C., the $\Delta R$ % was less than 2.6% for the four samples tested. This means that the change of viscosity caused by the gas adsorption on the IL film is very small at high temperature. The frequency changes were contributed mainly from the mass loading in the IL film and the Sauerbrey Equation relating frequency change to pure mass loading is valid. This enables qualification of the thermodynamic and kinetic parameters of the interaction of IL film with volatile organic molecules by QCM technique. Table 2 shows the Henry's constants of various vapors in ILs obtained from our experimental results. Ethanol, benzene and heptane have similar vapor pressure but heptane has higher Henry constant. This result indicates that some organic vapors interact strongly with the cations of ILs; while others interact strongly with the anions of ILs. Therefore, by orientating of the immobilized ILs with either cationic terminal or anionic terminal could lead to selective response of IL film to various compounds.

Figure 6:
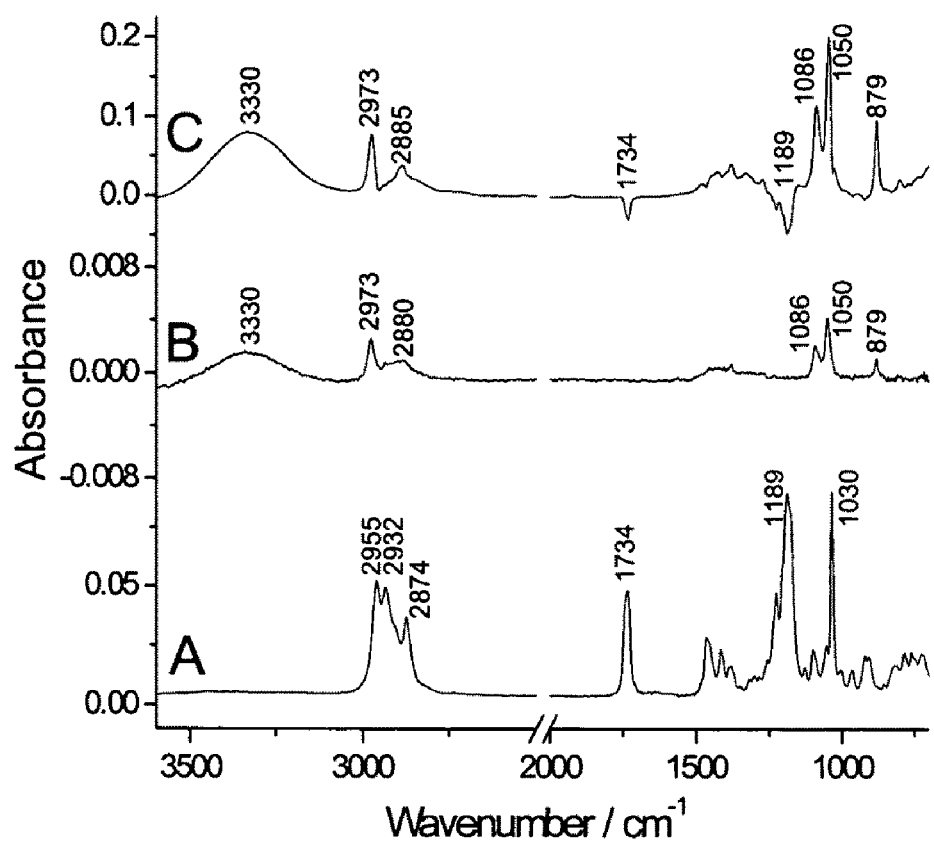
FIG. 6 illustrates three ATR-FTIR spectra (A, B and C) on a single plot. The graphs show the ATR-FTIR spectra of ionic liquid $P_{6,6,6,14}OCS$ film (Spectrum A), ethanol vapor exposed to bare substrate (Spectrum B) and to $P_{6,6,6,14}OCS$ film covered substrate (Spectrum C).

The key to a sensor array is to develop chemically selective interfaces which exhibit high level of chemical independence and structural order. Consequently, the information about which functional groups of an ionic liquid interacts with the organic volatiles is critical for the controlled configuration of IL on surface to generate IL films with a great diversity in structural and chemical properties. ATR FT-IR was used to characterize the gas/IL interaction to guide the surface design of IL selective interfaces. FIG. 6, spectrum A, is the absorbance spectrum of $P_{6,6,6,6}$OCS thin film. The peak at 1730 cm$^{-1}$ originates from the C=O (carbonyl) group. Peaks at 1187 cm$^{-1}$ and 1035 cm$^{-1}$ come from the O=S=O (sulfonyl) group. The other peaks come from the alkyl groups. FIG. 6, spectrum B, is the spectrum of ethanol when there is no IL film on the ATR crystal. When the IL film is exposed to ethanol, its absorbance spectrum is shown in FIG. 6, spectrum C. The negative peaks of C=O and O=S=O groups of $P_{6,6,6,6}$OCS indicate their interactions with ethanol vapor. Additionally, the intensity of the ethanol peaks were enhanced about fifty fold when interacting with only 10 μg/cm$^2$ IL film. This preliminary study shows that the intensity of ethanol peaks depends on the thickness of the film and on the concentration of the ethanol vapor in gas phase. ATR-FT-IR alone or by combination with other techniques can be invaluable to obtain information of IL orientation, kinetics, concentration of the vapor and the physicochemical interactions of ILs with the gas analytes to facilitate the configuration of IL on surface.

Figure 7:
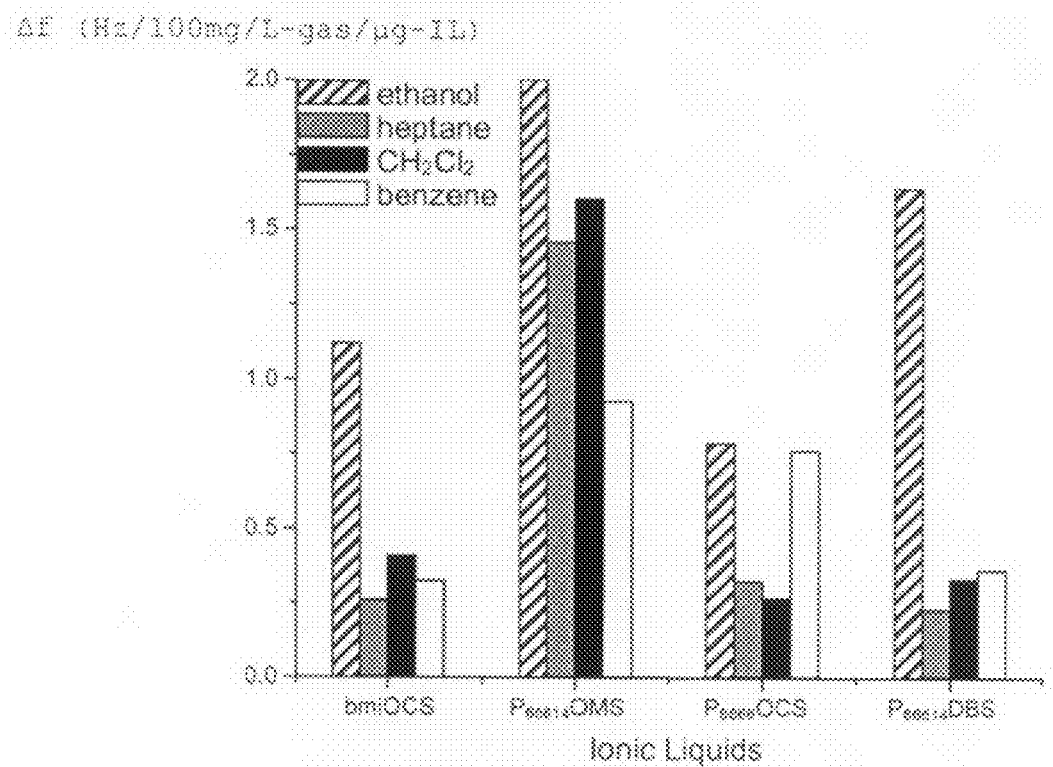
FIG. 7 is a graph showing normalized relative response pattern of IL sensors (coated with bmiOCS, $P_{6,6,6,14}DBS$, $P_{6,6,6,14}OMS$, and $P_{6,6,6,14}OCS$) for ethanol, heptane, $CH_2Cl_2$, and benzene at 120° C. The signals are normalized by the weight of IL coatings and the vapor pressure of each analyte.

FIG. 7 shows the different patterns when four different coating materials (three ionic liquids and a polyaniline) respond with ethanol, benzene, heptane and dichloromethane vapors by QCM. The preliminary results illustrate the feasibility of IL high temperature gas sensing and sensor arrays.

TABLE 1

Value of Damping Resistances and Their Changes During Experiments.

| | Temperature | | | | | | | |
| --- | --- | --- | --- | --- | --- | --- | --- | --- |
| | 24° C. | | 40° C. | | 80° C. | | 120° C. | |
| Resistance | R (Ω) | ΔR % | R (Ω) | ΔR % | R (Ω) | ΔR % | R (Ω) | ΔR % |
| Ethanol | 4.7 | ±11% | 3.9 | ±2.6% | 4.0 | ±1.9% | 4.4 | ±0.7 |
| Benzene | 3.3 | ±3.7% | 3.4 | ±2.2% | 3.4 | ±1.1% | 3.6 | ±1.4% |
| Heptane | 3.2 | ±1.6% | 3.1 | ±1.3% | 3.2 | ±1.2% | 3.4 | ±1.5% |
| Dichloromethane | 3.5 | ±12% | 3.5 | ±7.1% | 3.6 | ±3.3% | 3.9 | ±2.6% |

TABLE 2

| Henry Constant (units: Pa) | | | | |
| --- | --- | --- | --- | --- |
| Ionic Liquid | Ethanol | Benzene | CH$_2$Cl$_2$ | Heptane |
| beiOCS | 3.25E5 | 1.05E6 | 1.15E6 | 1.87E6 |
| bmiOCS | 5.57E5 | 2.03E6 | 1.55E6 | 2.58E6 |
| P6666OCS | 5.80E5 | 5.51E5 | 1.31E6 | 1.42E6 |
| P66614OMS | 3.85E4 | 4.33E5 | 2.25E5 | 0.31E6 |
| P66614DBS | 2.00E5 | 8.26E5 | 8.75E5 | 1.26E6 |
| P8888DBS | 7.23E5 | 1.25E6 | 9.71E5 | 1.88E6 |
| N7777DBS | 1.27E6 | 1.37E6 | NA | 2.50E6 |

Using various ionic liquids that were successfully prepared during the past four years (FIG. 1) along with those commercial available, the characteristics and techniques for preparation of thin (0.5 μm -50 μm) or ultra thin (5 nm -100 nm) IL films with controlled properties were investigated. Their applications in gas sensing both at room and elevated temperatures were explored. Preliminary work shows that the interface function group of the IL film plays important roles for its interaction with gas phase volatile organics. In the present disclosure, we take advantage of the broadly defined self-assembly and nano fabrication techniques to prepare orientation-controlled IL or IL/template films to optimize the sensor performance. AFM, FT-IR, ellipsometry and electrochemistry are used to study the modified IL film properties. The various combinations of electrochemical and surface techniques provide powerful ways to correlate structure and reactivity of surfaces and interfaces.

EXAMPLES 2-3

Thin-Film Immobilized IL/QCM Sensors

A model system using phosphonium dodecylbenzenesulfonate (i.e. $P_{6,6,6,14}DBS$) at a gold electrode is used to describe the experimental protocol for immobilizing thin-film ILs on a substrate for use in a QCM sensor. A similar protocol is applied to other ionic liquids (e.g. imidazolium ionic liquids). This leads to understanding the properties of the modified ionic liquid films on the gold surface. A series of chemically sensitive and selective ionic liquid interfaces can be designed whose responses to a range of vapors and gases are characterized, allowing selection of the best subset of materials for a particular application. Pattern recognition algorithms are developed. A portable QCM sensor array is developed for environmental monitoring for gas quality and automobile emission. The invention has substantial scientific and practical impacts in surface chemistry, material sciences and sensor technology.

Rigidity of the surface film is important for quantitative analysis by QCM technique. A thick film has a slow response time due to long diffusion pathway, but also its response is complicated by both the mass loading and the viscosity change of the film. A thin film allows fast adsorption equilibrium, short response time and accurate quantification by Sauerbrey equation. Consequently, in one embodiment the invention focuses on developing methods to make rigid IL thin films (e.g., thin (0.5 µm -50 µm) or ultra thin (5 nm-100 nm)).

Most of the ILs are soluble in common volatile organic solvents, such as ethanol, acetone and dichloromethane. An IL thin film can be easily prepared from its solution by casting, spin coating or spray coating. The thickness of the film can be controlled by the solution concentration. When spin coating technique is used, the film thickness can also be controlled by the spin velocity. The thickness of an IL film coated by spray coating can be affected by several parameters of the spray gun aperture size and spray pressure. All of these three methods can provide a thin and uniform IL film but they cannot provide controlled molecular orientation. Furthermore, a small degree of "slippage" could occur at high temperature if the film is physically adsorbed on the gold substrate. Electrostatic, hydrophobic interactions, covalent attachment and polymer entrapment methods have been used extensively in the literature to immobilize organic or biological molecules with improved orientation. Covalently immobilizing ILs using their incorporated HS group or $Si(OR)_3$ group were also reported. However, this approach requires synthetic effort to modify each of the IL molecules and is labor intensive.

Owing to the unique charge properties of ionic liquid, they can be immobilized on a gold surface based on the electrostatic interactions of ionic liquid and a charged template. The properties of these immobilized films can be compared to those casting, spin coating or spray coating methods. The goal is to prepare a range of immobilized IL thin films with broad chemical diversity so that these interface materials respond sensitively and selectively to a variety of analytes. All developed IL thin films are characterized by an electrochemical technique, elliposometry and AFM, and then are investigated for their interaction with organic vapors by QCM, network impedance analyzer, and ATR FT-IR.

Self-Assembled Monolayer (SAM): The first approach is to take advantage the well established SAM technology. The beauty of SAMs is in their spontaneous association of molecules under equilibrium conditions that gives stable, structurally well-defined two-dimensional aggregates. The vast majority of alkanethiolate SAMs provide simple, reproducible, relatively well-ordered materials platforms with chemically diverse charged terminal groups. By varying the SAM terminal group, the interfacial functionality of the monolayer can be changed. Even though the SAM can either have the function of performing some aspect of gas sensing in its own right, using it as a "primer" onto which the ionic liquid will be "grafted" should provide more complex bilayers with additional control over selectivity and sensitivity.

Figure 8A:
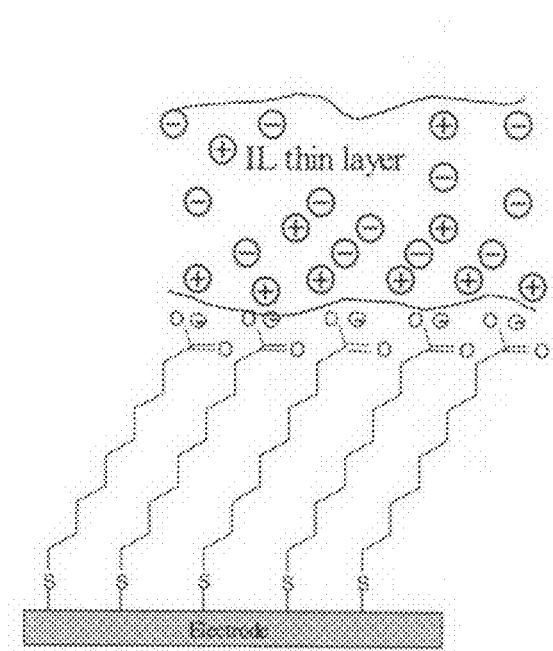
FIGS. 8A and 8B show immobilization via electrostatic interaction between cations/anions of ILs and SAMs.

As shown in FIG. 8A, a SAM with carboxylic acid terminal groups and various chain lengths can be used as a surface modifier to change the physical and chemical nature of the Au substrate (for example, an electrode). The surface can then be treated with alkali solution and the carboxylic acid can be converted to carboxylate, rendering the surface negatively charged. Next, the surface can be immersed in an $P_{6,6,6,14}DBS$ solution. The interaction between the carboxylate group and the tetraalkylammonium or tetraalkylphosphonium cations can render some level of preferred orientation of the $P_{6,6,6,14}DBS$ modified electrode surface. The hydrophobic interaction among alkane chains in SAM and ILs should play additional roles for the IL/SAM composite.

Figure 8B:
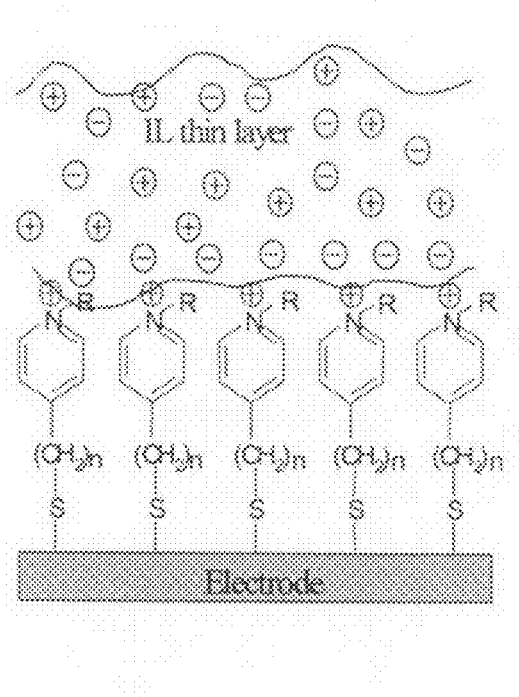

Alternatively, as shown in FIG. 8B, the electrode surfaces will be made positively charged using a SAM with pyridine terminal groups, which can be treated with iodoalkane solution (Liang, C., et al., Anal. Chem. 74, 2172-2176 (2002)). The pyridine can react with the iodoalkane to produce pyridinium cations (Ohe). Afterwards, the surface can be immersed in a $P_{6,6,6,14}DBS$ solution. The ILs can be immobilized on the electrode surface via the interaction between the pyridinium groups and the organosulfonate anions.

Other SAMs with charged organic terminal groups, for example ammoniums, phosphate anions, or sulfonates, which can form anions or cations can be used. Ethanol can be used as a solvent for n-alkanethiols up to a chain length of about 18 methylene units (n=18). Above 18 methylenes, the compounds tend to precipitate. In this case hexane, dimethyl ether, or tetrahydrofuran can be used as solvents. For shorter chain thiols, which are water soluble, aqueous solutions will be used.

EXAMPLE 2

Thin-Film Immobilized IL/QCM Sensors (SAM Formation)

Gold beads were prepared by annealing in a methane/$O_2$ flame (Grate, J. W., et al., Sens. Actuators B 3, 85-111 (1991); and Finklea, H. O., in: Encyclopedia of Analytical Chemistry, Ed. R. A. Meyuers, Self-assembled monolayers on Electrodes, John Wiley & Sons, Chichester, 1-26 (1999)) to produce a smooth surface with predominant Au(111) facets. Freshly prepared gold beads were immersed in 1 mM $HS(CH_2)_{10}COOH$/THF solution for 3 days, followed by treatment with 0.1 M KOH solution for 15 min. Finally it was soaked in 5 mM IL ($P_{666,14}DBS$)/EtOH solution for 2 days. After the above treatment, the gold bead was rinsed in EtOH for 24 hours. Characterization of the gold bead was carried out in 1 mM $Fe(CN)_6^{3-/4-}$ solution containing 0.1 M $NaClO_4$ by Cyclic Voltammetry (CV) and Electrochemical Impedance Spectrometry (EIS) at each step of modification.

Figure 9:
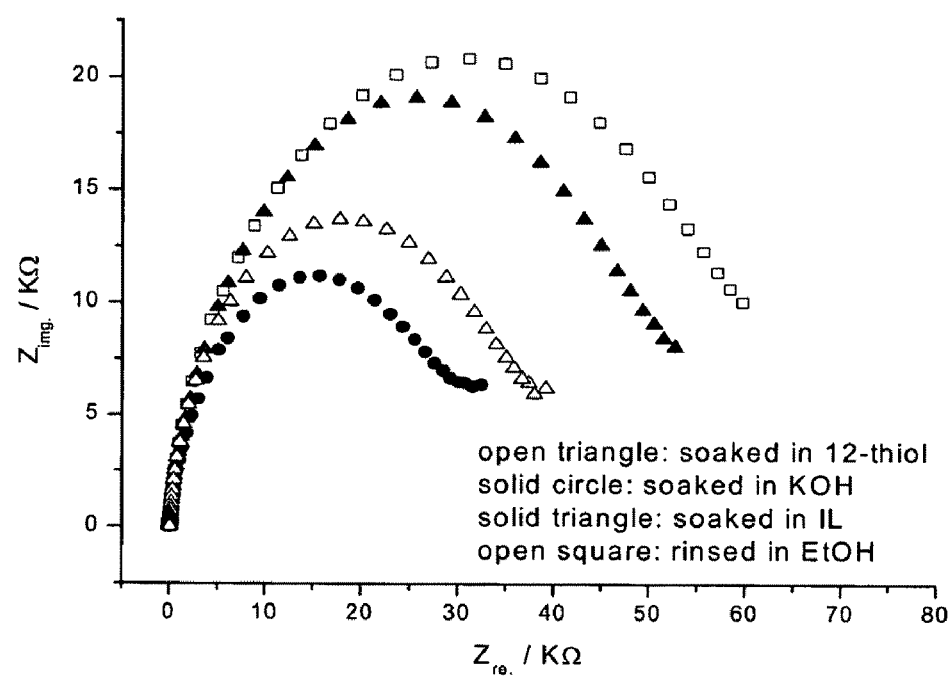
FIG. 9 is a graph showing Nyquist plots of EIS study of 1 mM $Fe(CN)_6^{3-/4-}$ in 0.1 M $NaClO_4$ on a gold electrode modified by soaking sequentially in: 1 mM $HS(CH_2)_{10}COOH$/THF solution for 3 days (open triangle), 0.1 M KOH for 15 min (solid circle), 5 mM IL $P_{6,6,6,14}DBS$/EtOH solution for 2 days (solid triangle) solutions and ethanol (open square). The gold electrode was prepared by annealing in a gas/$O_2$ flame, to produce a smooth surface with predominant Au(111) facets. After each treatment, the gold electrode was rinsed in ethanol (EtOH) for 24 hours before EIS study was carried out.

FIG. 9 shows that the charge transfer resistance ($R_{et}$) value increases after each step of modification. Immobilization of the ILs results in a more passive surface. After the thiol/IL modified electrodes were rinsed with THF, the $R_{et}$ increased further. This result confirms that a strongly immobilized IL layer was made; otherwise the $R_{et}$ value would have decreased if the solvent removed IL. The thiol/IL modified gold surface may be at its dynamic state when soaking in the solvents, allowing for further organization of the thin film.

Polymers/Polyelectrolytes: Polymers (e.g. poly(dimethysiloxane) or rubbery polymers (Finklea, H. O., in: Electroanalytical chemistry Ed. A. J. Bard, I. Rubinstein, Electrochemistry of Organized monolayers of thiols and related molecules on electrodes, Marcel Dekker, New York, Vol. 19, 109-336 (1996)) are the favorite materials for gas sensing, however they often act as passive supports or structure materials to provide stability for sensing and tend to show very little specificity and are not useful as "stand alone" sensors (Nuzzo, R. G., et al., in Adsorption of bifunctional organic disulfides on gold surfaces, J. Am. Chem. Soc., 105, 4481-4483 (1983)). Conductive polymers and polyelectrolytes have mostly been studied for applications in microelectronics, photo electronics and energy storage. Conductive polymers are often regarded as polyions after they are doped. Their use as gas sensing materials are not well explored. Both polyelectrolyte and conductive polymer have charge which make them ideal materials as a template materials to make IL composite films. The fundamental idea has a much broader scope, and various pairs of conductive polymer/polyelectrolyte and IL composites can be imagined. The value and importance of the wide range electrodes modified by immobilization of a single species (conductive polymer or polyelectrolyte) is widely acknowledged and we believe that using appropriately chosen pairs of immobilized species can produce unique surfaces with valuable chemical properties (e.g. controlled porosity, orientation and tunable thickness).

Figures 10A, 10B:
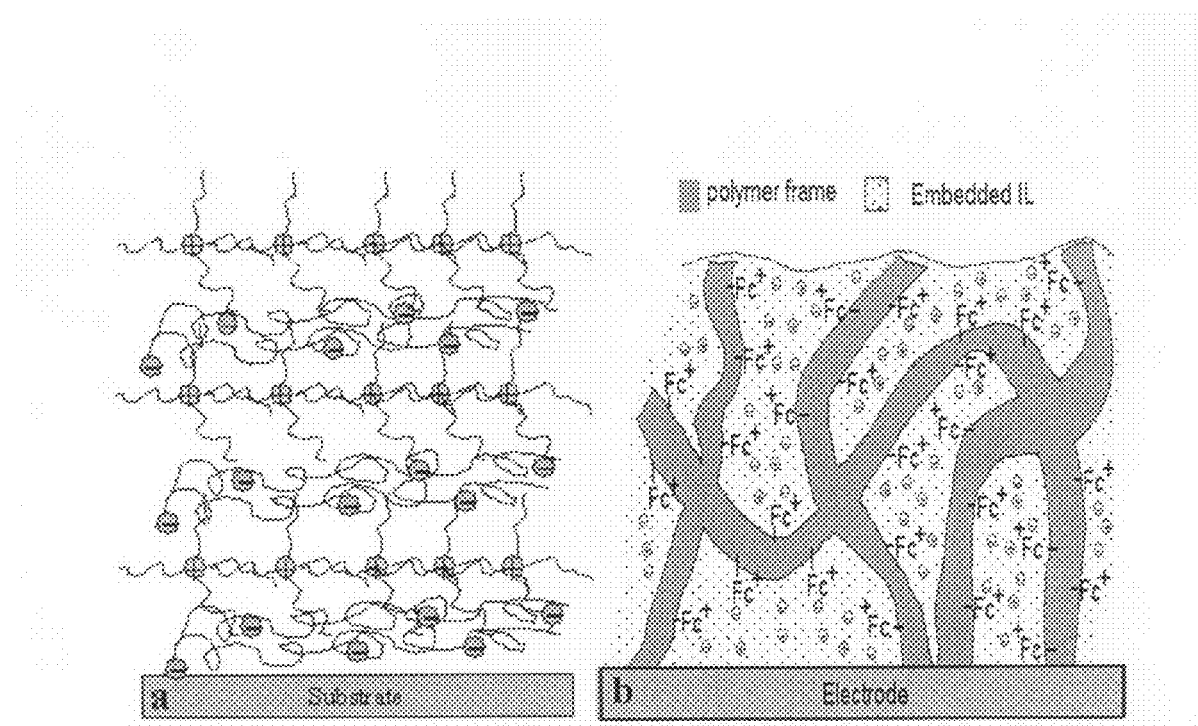
FIG. 10A illustrates layer-by-layer deposition of polysulfonate styrene having negative (−) charges, and ionic liquid having positive charges (+), on a substrate.
FIG. 10B illustrates an electrode having PVF with charged groups ($Fc^+$) as a polymer frame embedded with ionic liquid.

Polysulfonate styrene (polystyrene sulfonate, PSS) and poly(vinylferrocene)(PVF) can be used in the present invention, however other polyelectrolytes can be used to prepare the IL film on the surface. The layer-by layer deposition of polyelectrolytes (ie. ionomers such as polysulfonate styrene) and ionic liquids can be used (FIGS. 10A and 10B). Two methods can be used for PVF/IL film preparation. One is to deposit it on an electrode electrochemically from ionic liquid bathing electrolyte, the other is by mixing it with ionic liquids in certain organic solvents (e.g. $CH_2Cl_2$) and cast on the gold substrate.

Figure 11:
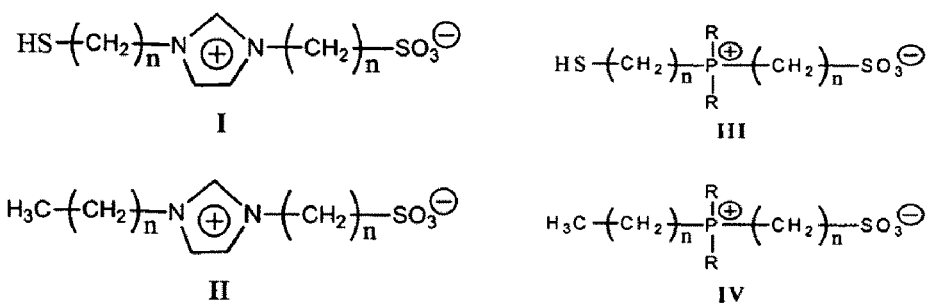
FIG. 11 shows chemical structures of thiolated zwitterionic liquids (I, III) and primary zwitterionic liquids (II, IV).
Figure 12A:
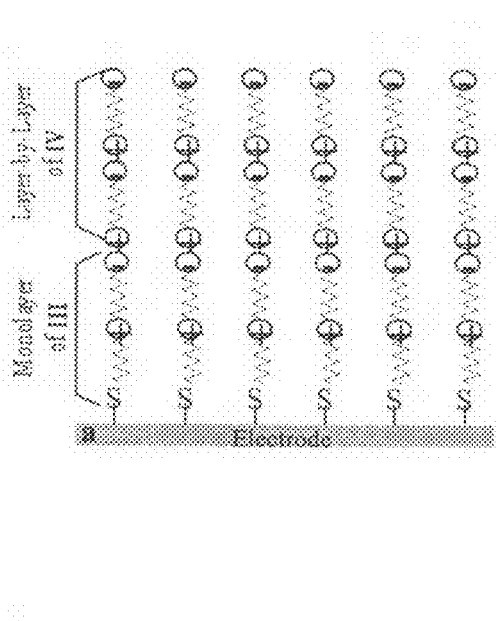
FIGS. 12A and 12B are schematics of the layer-by-layer deposited zwitterionic liquid film structure (FIG. 12A) and polyionic liquid film structure (FIG. 12B).
Figure 12B:
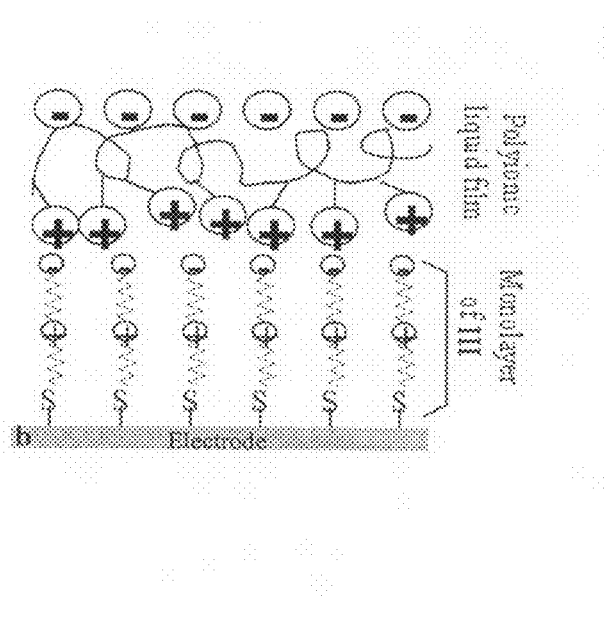

Zwitterionic/Polyionic Liquids: Recently, zwitterionic liquids or polyionic liquids (FIG. 11, compounds I and II), for example based on imidazolium sulfonate, have been synthesized (Nuzzo, R. G., et al., J. Am. Chem. Soc., 109, 2358-2368 (1987)). In polyionic liquids, one of the ions is attached to a flexible polymer backbone as side groups or is incorporated into the polymer backbone. They are liquid macromolecules at temperatures lower than 100° C. (Christensen, P. A., et al., J. Electroanal. Chem., 318, 407 (1991)). Zwitterionic liquids or polyionic liquids surface assembly can provide additional control and rigidity than those discussed above. Zwitterionic liquids based on tetraalkylammonium or tetraalkylphosphonium, compounds III and IV can be synthesized. A layer-by-layer strategy of immobilization of the zwitterionic liquids can be developed for zwitterionic liquids (FIG. 12A) and polyionic liquids (FIG. 12B). The number of layers and the terminal layers effects on film properties can be considered.

The immobilized (bound) IL thin films can be used for their physical and chemical properties by means of electrochemical methods, QCM, AFM, Ellipsometry and Reflectance Absorption Infrared Spectroscopy (RF-FT-IR) to obtain structural, thickness, rigidity, orientation, stability, and surface coverage information of the immobilized IL thin films. QCM method can be used to study the thermal stability and solubility of the analyte in the IL films and to obtain thermodynamic (e.g. Henry's constant) and kinetic information (e.g. rate constants). Electrochemical methods can be used to develop the interface properties of ILs thin film, for example, the hydrophobicity/hydrophilicity of ILs film, the permeability of water, ions or redox species within the IL films and the ionic conductivity of the IL film. AFM and ellipsometry can be used to study the morphology change of the IL films before and after the exposure to organic vapors. RF-FTIR can be used to study the orientation of ILs and the interactions of IL film with vapor molecules. That information provides important guidance for ILs synthesis and surface immobilization strategies for IL sensor array, and provide invaluable fundamental understanding of the ILs and volatile organics interactions which are essential to the future industrial and laboratory applications.

High temperature gas sensing devices can be provided using IL thin films developed above via QCM transducers and perform a systematic evaluation for the long-term thermal stability of those IL surface assemblies. The target application is emission control and industrial application rather than the trace volatile analysis which is best done by GC-MS. Consequently, the sensitivity is not the limiting factor. But we can improve the sensitivity by controlling film thickness and using high frequency transducer or overtones. AT-cut quartz crystals that exhibit a high frequency stability ($\Delta f/f=108$) and almost zero temperature coefficient between 0° C. to 50° C. can be used. Above 50° C., the resonance frequency of QCM can depend on the temperature. If the temperature is very stable, the frequency response can reflect the mass loading and viscosity change on the IL/QCM. In order to ensure an accurate measurement, a dual QCM system (DQCM) can be used at high temperature conditions. The DQCM method includes a cell incorporating two quartz crystals. The reference sensor consists of a bare Au quartz crystal, and the other sensor consists of the IL immobilized Au quartz crystal. While interaction of gas analytes in the DQCM cell, the frequency difference between the reference and sensing crystals can be monitored. This design will improve sensitivity and detection limits.

Preliminary data show a good linear relationship for IL sensor which suggests low viscosity changes of the IL films upon absorption of organic vapors. At an ideal condition, the frequency change is only caused by the mass loading on the surface. To evaluate mass loading effects experimentally, an equation was derived, from the Sauerbrey Equation, relating sensor responses to partition coefficients: $\Delta f_{v(mass)} = \Delta f_n C_v K/\rho$, where $\Delta f_{v(mass)}$, $\Delta f_n$, $C_v$, $K$ and $\rho$ are, respectively, the frequency shift caused by the adsorption of the vapor, the coating thickness in kHz, the vapor concentration in the gas phase, the partition coefficient and the coating material's density. However, reports show that both the mass loading and the viscosity change of the IL film upon the absorption of vapors can cause the frequency change at room temperature. The change of the viscosity or modulus of the coating is reflected by the change of damping resistance fitted by the BVD circuit. At higher temperatures, the viscosity decreases significantly. For example, phosphonium based ionic liquids tend to have viscosities somewhat higher than their ammonium counterparts, especially at or near room temperature.

However, on heating from ambient to typical industrial reaction temperatures (e.g. 70-100° C.) their viscosities generally decreased to <1 cPs (Aslanoglu, M., et al., Analyst, 123, 753-757 (1998)). Ionic liquid viscosities are also very sensitive to solutes, and the addition of reactants and or catalysts can be expected to further reduce viscosity. Consequently, the quantitative relationship between frequency change and analyte concentration can be evaluated based on several variables (temperature, viscosity, mass loading). Correlation of these relationships with data on the vapor pressure of ILs at high temperature will also be investigated. An advance technique with Network Impedance Analysis instruments and real-time data fitting software is used to measure both the frequency and the resistance real-time for above study.

The real time sensorgram can provide kinetic and thermodynamic information to reveal the interaction between gas molecules and ionic liquid coating. This information can be used to improve the performance of IL/gas sensors. Some variables need to be considered in the gas sensing kinetics. The most important one is the partial pressure of the gas to be detected. The partial pressure also determines the maximum response or the equilibrium response if the contact time is long enough. Another important variable is the flow rate. Primary results show that the response time not only depends on the nature of the gas and the ILs, but also depends on the flow rate. Theoretically, if the response is rate-limited by the diffusion of gas molecules in gas and liquid phase, increase the flow rate can reduce the thickness of the diffusion layer and thereafter reduce the response time. In addition, the flow rate also generates an extra pressure called dynamic pressure. According to Bernoulli's equation, the total pressure is the sum of static pressure and dynamic pressure. Bernoulli's equation is:

$$P_t = P_s + \frac{1}{2}\rho v^2,$$

where $P_t$ is the total pressure that determines the association rate and equilibrium amount; $P_s$ is the partial pressure in static gas; $\rho$ is the density of gas and v is the velocity of the gas in meter per second (m/s). The higher flow rate not only speeds up association rate but also increase the equilibrium amount of gas in IL. However, the time to reach equilibrium does not necessarily decrease. Increased amount of gas that can be associated with IL can require more time to reach the equilibrium although the association rate is fast now. An effective kinetic model can be developed to take these important variables into account.

Figure 13:
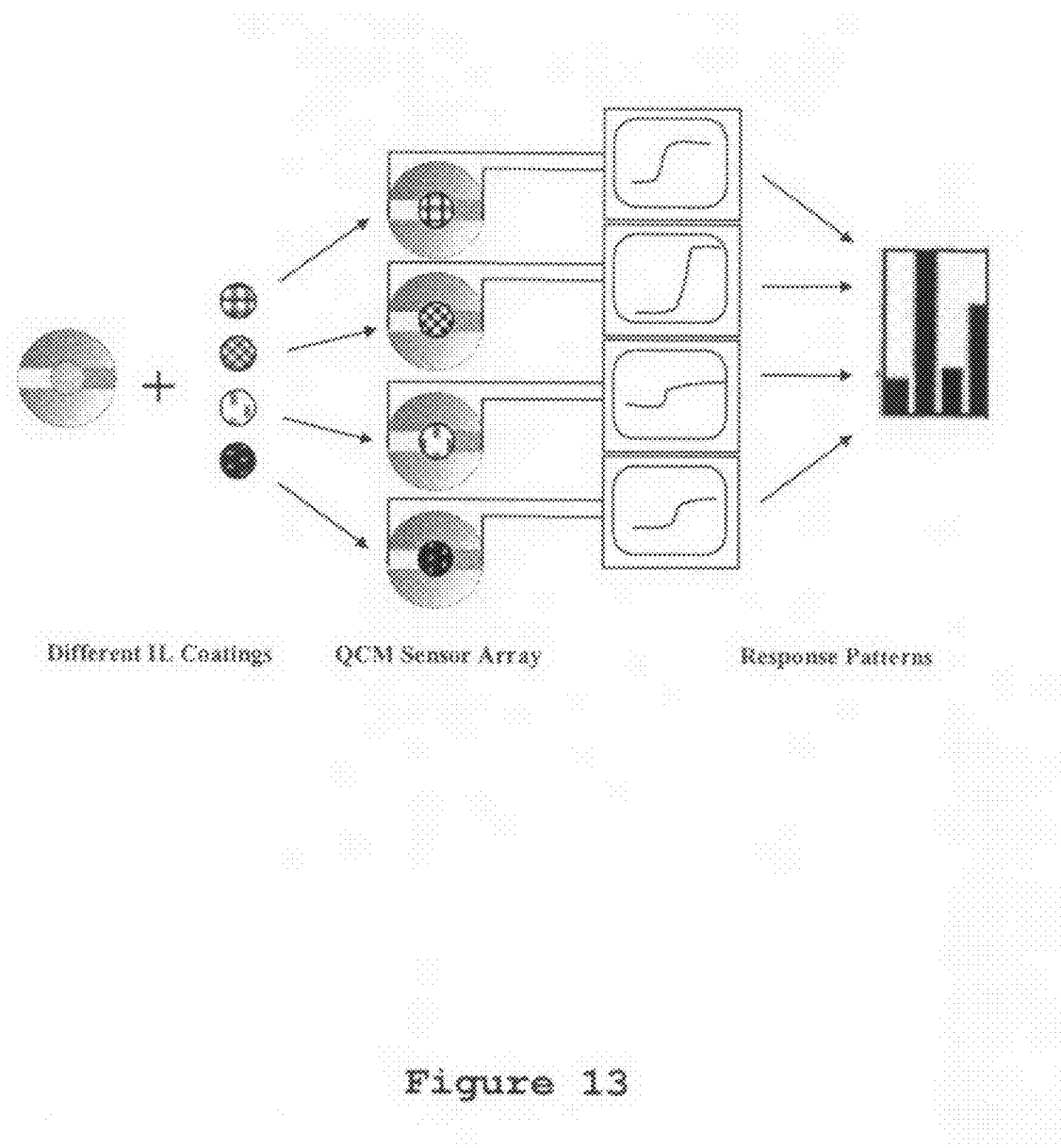
FIG. 13 is a drawing showing a schematic of a sensor array of QCM devices having different ionic liquid (IL) coatings and response pattern reorganization.

The chemical selective ionic liquid films developed can be used to design a QCM sensor array. The chemical selectivity of ILs to volatile organics depends on the interactions of ILs with volatile analyte. Therefore, varying the structure, and hence the properties, of the ILs can enhance the selectivity of the ILs/QCM sensors. For example, increasing the length of the alkyl chain in the cations can increase the sensitivity to olefins vapors; introduction of aromatic rings, such as naphthalene, anthanthrene or phenanthroline, can increase the sensitivity to fragrance vapors; ILs with inorganic anions, such as $BF_4^-$, $PF_6^-$, can have strong absorption to $O_2$ or $CO_2$; ILs with chloro- or fluoro-groups can have strong absorption to halogenated hydrocarbon. ILs offer many options for chemical modifications and hence a huge flexibility in tailoring molecular recognition sites by controlled organic synthesis and surface designs. Consequently, surface design and organic synthesis can be combined to modify the properties of each sensitive layer to develop sensors which can generate independent features with the same type of transducer. The signals of these sensors are recorded simultaneously. Due to their partly overlapping sensitivities, instead of a simple calibration function, multicomponent analysis or pattern recognition (Grate, J. W., et al., Faraday Discuss. 107, 259-283 (1997); Grate, J. W., et al., Anal. Chem. 70, 199-203 (1998); Ricco, A. J., Electrochem. Soc. Interface 3(4), 38-44 (1994)) can be developed to obtain the desired analytical information (FIG. 13). For the initial study, a simple gas mixture can be analyzed so to provide information about the limitation and potential of IL sensor arrays.

The vast chemical diversity of selected interfacial materials provides solid database for statistical pattern recognition. Differential interaction among the set of IL layers in the array produces response patterns that can be correlated with the identities, or at least the functional group classes, of the analyte vapors. Based on the response frequency and other characteristics (e.g. damping resistance) from sensor arrays, classification models can be established to identify different classes of compound through a series of supervised learning algorithms such as linear discriminant analysis, classification tree and neural networks etc. These models not only characterize the compound clusters numerically with low misclassification rates but also have good ability of predictability. Unknown volatile organic compounds and urban gas pollutants can be identified by statistical models to classes with same or similar chemical characteristics. Due to the uncertainty of the identification process, false positive and false negative rates can also be calculated through statistical modeling techniques. Sensory arrays with low misclassification rates have high reliability in practical applications. However, if the stand-alone IL sensor arrays run into difficulty meeting the performance requirements of many potential applications. The IL's can be combined with other techniques, such as gas chromatography (GC).

Figure 14D:
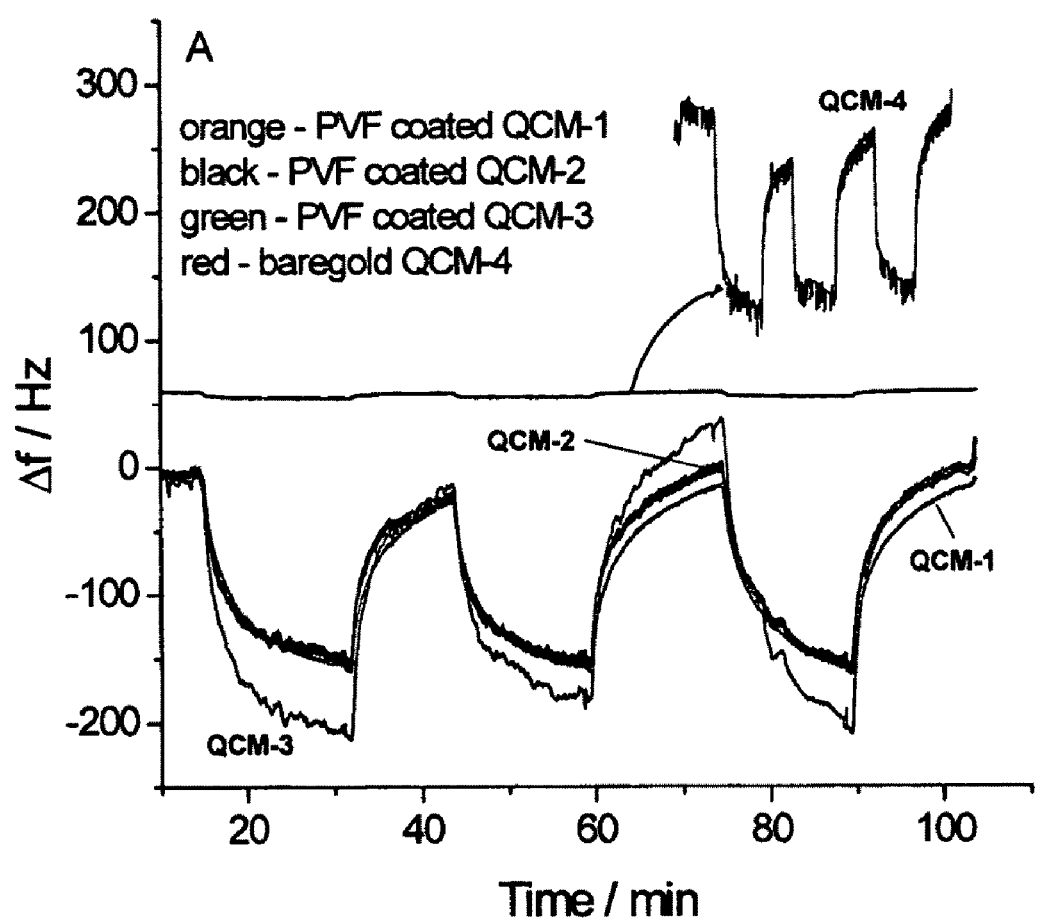
FIGS. 14d and 14e show QCM sensorgrams of the symmetric MQCM array. QCM-1 is bare gold, QCM-2 and QCM-3 are coated with 216 nm and 217 nm PVF respectively, and QCM-4 is coated with 311 nm PVF.
Figure 14E:
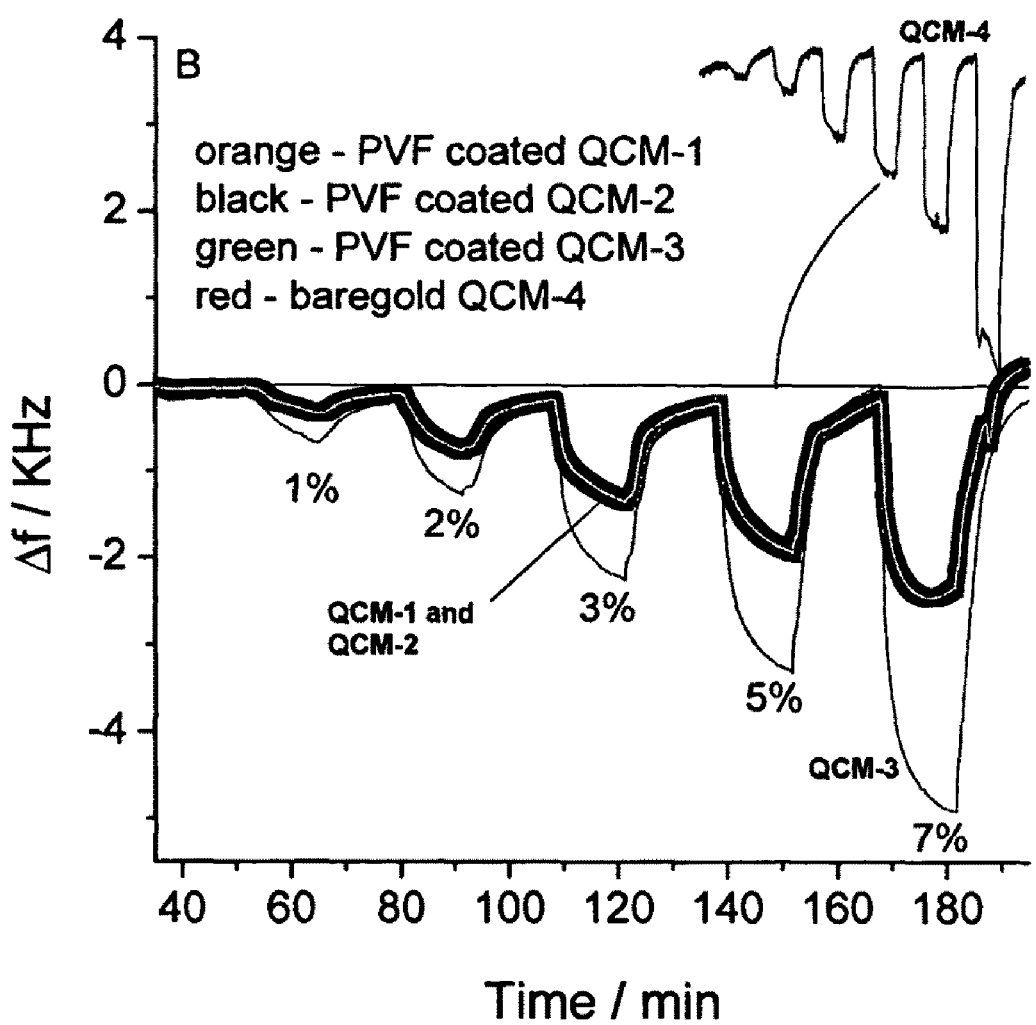

The requirements of various sensors are based to a large extent on their respective applications, but the common stipulations are (1) sensitivity in the range of interest; (2) selectivity for the analyte; (3) broad dynamic range; (4) reversibility; (5) robustness and reliability; (6) lack of frequent calibration; (7) fast response; (8) inertness to sample matrix; (9) unattended operation, robot-compatibility, user friendliness; (10) small size; and (11) low cost (McQuade, D. T., et al., Chem. Rev., 100, 2537-2574 (2000)). The recently designed QCM transducer with state-of-the art high-speed Digital Signal Processing (DSP) hardware and wireless connectivity through UWB/RF (illustrated in FIG. 13) can be used to do field test for organic pollutants, and FIG. 14 shows a graph of frequency vs. time for four sensors in an array. The IL sensor arrays not only permit measurement of multiple analytes in the same small sample but also reduce the analysis time. With every element in the sensor array chosen to respond to a number of different chemicals or classes of chemicals but not necessarily individually highly selective toward any given analyte, so the difficulty of developing new materials with high chemical specificity for each analyte is reduced. Instead, the collection of sensors can contain as much chemical diversity as possible, so that the array responds to the largest possible cross-section of analytes (Tatumi, R., et al., Chem. Commun., 83-85 (2005); Yoshizawa, M., et al., Chem. Commun., 1828-1829 (2004); and Ohno, H., et al., Electrochimica Acta, 48, 2079-2083 (2003)).

EXAMPLE 3

Thin-Film Immobilized IL/QCM Sensors
(Polyaniline Scaffold)

This example shows ionic liquids immobilized on polyaniline scaffold for methane detection. Flammable gas sensors are essential in ambient air monitoring, occupational health and safety, biomedical diagnostics, industrial process control, and military and civilian counter-terrorism. Among various flammable gases, recent mine explosions showed that current methods for methane detection are not adequate. Methane is the major constituent of natural gas. The lower and upper explosive limits of methane in air are 5% and 15%, respectively. The warning percentage is often set to 0.5-1%. After carbon dioxide, methane is the second most important greenhouse gas that contributes to global warming. Methane is odorless. If inhaled, methane effectively replaces the oxygen in the body, causing suffocation and ultimately death will result. The detection of this potent gas is essential in the environmental, industrial and domestic worlds.

Although methane reacts drastically with chlorine or oxygen, it is in essence a fairly chemically inert gas. This low reactivity therefore makes it difficult to develop strategies that rely upon its chemical interactions for sensing. The physical adsorptions of methane on most solid-state materials are very weak. Since the chemical inertness of methane, commercially available methane sensors on the market so far are based upon either adsorption on semiconductors or optical methods. The most frequently used metal oxide is tin oxide ($SnO_2$). Its conductance or resistance changes upon adsorption of various gases. However, methane cannot be directly absorbed on $SnO_2$ and detected. The present of oxygen is a requirement for the successful detection. The oxygen chemisorbs onto the surface, thereby decreasing the concentration of electrons and increasing the electrical resistance. In the presence of methane, the gas detection mechanism involves the oxidation of methane with adsorbed oxygen to form $CO_2$ and $H_2$. This reaction consumes the oxygen on the surface, thereby increasing the conductance of the material. Due to the chemical inertness of methane, its oxidation has to take place at temperatures above 400° C. to obtain the required sensitivity. In addition, the dependency of the resistance of the metal oxides on the vapor concentration is not linear, which reduce the accuracy of quantitative analysis. Optical based methane sensors that have significant advantages in terms of sensitivity, owing to the very sensitive optical detectors, and of selectivity, as the absorption lines are usually a unique feature of the gas under detection. But they are often expensive and less-portable. Other detection methods are constantly explored, such as amperometric detection, biosensors, and piezoelectric sensors, but commercialization development has been slow.

Three things are needed to support a fire or explosion: a source of fuel (e.g. flammable gas or vapor), air (oxygen) and a source of ignition (e.g. spark, open flame, or high temperature surface). As a result, a sensor for flammable methane gases requires the sensing materials to be non-reactive, of low vapor pressure, have strong physical or chemical interactions with methane and functioning over a broad temperature range. As aforementioned, the chemical inertness of methane makes its absorption on most solid-state materials very weak. Room-temperature Ionic Liquids (ILs) represent a promising material for methane sensing. ILs have negligible vapor pressure at ambient pressure and possess high thermal stability in air. Typical IL decomposition temperature is 350+° C. Furthermore, literature reports show that flammable gases (i.e. $CH_4$, $C_2H_4$, $C_2H_6$, $CO_2$, $O_2$) have wide varying gas solubilities in ILs. For example, it has been reported that methane has a Henry's constant of 1690 bar in ionic liquid $bmiPF_6$ (1-n-butyl-3-methylimmidazolium hexafluorophosphate). The value is much lower than that of nitrogen, >20000 bar and oxygen, 8000 bar indicating a sufficient solubility of methane in $bmiPF_6$.

For all chemical sensors, sensitivity, selectivity, speed of response and reversibility are a consequence of the thermodynamics and kinetics of coating material/analyte interactions. In the past few years, the unique thermal stability of room temperature ionic liquids (ILs) were explored for their applications for high temperature gas sensing and gas chromatography stationary phase. Results from our lab demonstrated that ILs allows fast and reversible mass transfer for gas detection and IL sensor array in conjunction with the real-time, portable, low cost characters of QCM transducer can successfully classify volatile organic compounds at high temperature. The challenge in using ILs as sensing materials lie in their low sensitivity at high temperature since thermodynamics does not favor of gas analyte partition or adsorption on the liquid or solid interface at high temperatures. At high temperatures, when ILs were directly casted on the gold QCM surface, they may dewet from the surface and spread out from the center of gold if the adhesive intermolecular force is not strong enough. This can significantly affect the sensitivity and the reproducibility of the sensor. To achieve high sensitivity and reproducibility, it is essential that ILs can be coated as a smooth, thin and homogenous film that maintains its integrity without forming droplets or spread out when the measurement temperature is increased. Thin films further satisfy mass detection based on Sauerbrey's equation if a QCM transducer is used. The obvious approach to increase the sensitivity is to increase the amount of sensing materials coated. But increasing sensitivity via a thick IL film has several drawbacks such as non-rigid film with significant film viscosity change upon gas adsorption and a slow response time due to long diffusion pass way. An alternative approach is to use a stable, porous solid template that is readily wet by ILs to form IL thin films to achieve high sensitivity but at the same time maintain its thin rigid properties. Alumina nanopores were explored as such template for IL immobilization via QCM. When the nanopores were partially filled with ILs, the viscoelastic effect is absent and good quantitative analysis was achieved. Although the nanopores can hold more IL than a smooth surface, the detection limits were still very high. For two nonpolar examples, the values were 1875 $mg/m^3$ and 7634 $mg/m^3$ for cyclohexane and isooctane, respectively. The ideal template will be a porous solid scaffold that is stable, with large surface area and can be chemically modified or tuned to enhance the wettability of ILs. Owing to the unique charge properties of an IL, a solid template that has various charge states will be preferred so that its wettability can be increased through the electrostatic interactions between the ionic liquid and the charged template.

In this example, conductive polymer polyaniline (PAN) was selected as a template to immobilize ILs for methane detection via QCM transducers. PAN meets most if not all above requirements as an ideal support for IL immobilization. PAN is one of the most well studied conductive polymers. The properties of PAN film including conductivity, thickness, morphology, and oxidation states could be reproducibly controlled by varying the conditions of the polymerization both by chemical or electrochemical oxidation. PAN film possesses excellent stability in conductivity, structure and morphology at a large temperatures range from very low temperature to as high as 250° C. PAN has been explored successfully as a matix or sensing materials for gas sensor. The methods to electrochemically deposit a PAN film on gold with expect properties and morphologies were well established. Most importantly, PAN charge states can be easily controlled by varying the redox potential. Our results show that at its doped state, a positively charged PAN serves as a stable support for IL immobilization. Negatively charged IL anion interacts strongly with the PAN polymer via hydrogen bond. Significantly improvement of sensitivity (0.1% methane in nitrogen) and stability of methane sensors were observed when ILs were immobilized on PAN. Little PAN interaction with the methane analyte was observed indicating excellent wettability of ILs on PAN surface with no complication for the sensing mechanism. The study fully revealed the advantageous of IL as sensing material through immobilization on PAN templates.

Chemicals: Butylmethylimidazolium camphorsulfonate (BMICS), butylmethylimidazolium methylsulfonate (BMIMS), tetrahexylphosphonium camphorsulfonate (P6666CS), trihexyltetradecylphosphonium methylsulfonate (P66614MS) ILs are synthesized by Dr. Rex Ren, IL-TECH Inc. (Middletown, Conn.) with over 98% purity. Ultra high purity methane (99.99%) in compress cylinder from (AGA Gas Inc., Canton, Mich.) was used as source of methane. Aniline (Merck) is purified by distillation under $N_2$ atmosphere and used immediately after distillation. All other chemicals are analytical grade, and 18 MD Millipore purified water is used for all the aqueous solutions.

Preparation of Pan Film with IL: Pan Films were Deposited on Both Sides of the QCM electrodes with an EG&G 273 potentiostat from 0.1 M aniline solution containing 1.0 M $HClO_4$ by controlling the electrode potential at 1.0 V vs SCE for 500 s or dynamically scan the electrode potential between −0.3 V to 1.0V vs SCE for 30 cycles at a scan rate of 100 mV/s. The counter electrode is Pt wire. The electrolyte solution is purged with $N_2$ for thirty minutes prior to experiments. After the polymerization, the PAN film was characterized in a 1.0 M $HClO_4$ solution by cyclic voltammetry. The final potential is set to −0.3 V, 0.35 V and 1.0 V to control the oxidation state of the result PAN film. At −0.3 V, 0.35 V and 1.0 V, the PAN film is at its reduction, partially oxidation, and oxidation states, respectively. The PAN/IL composites are prepared by soaking the PAN film in IL solutions in ethanol with various concentrations overnight. After the soaking, the PAN film is dried in $N_2$ atmosphere without further rinse.

Figure 15:
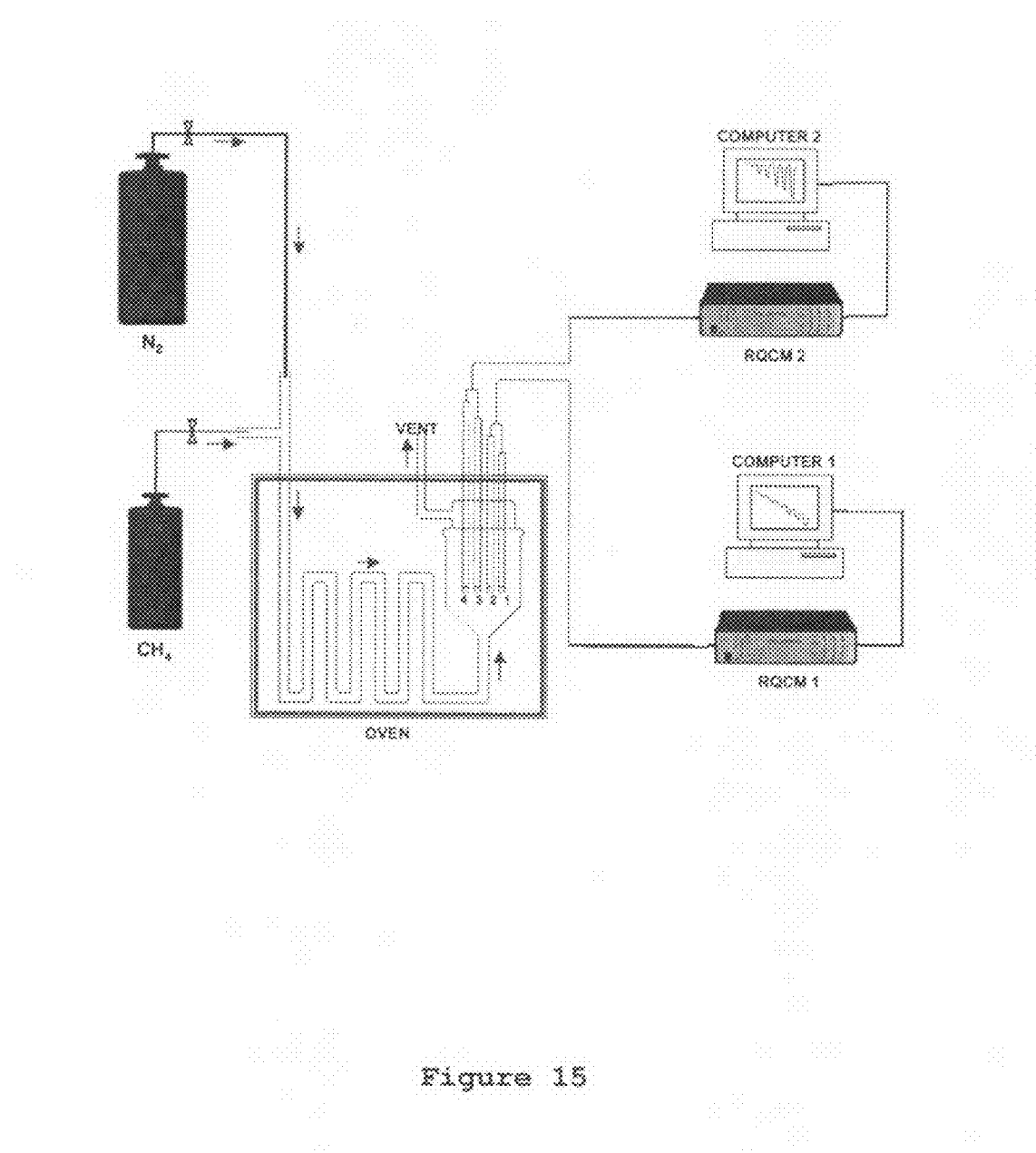
FIG. 15 shows the flow system setup for characterization of the PAN/IL sensors.

Flow system setup and characterization of the PAN/IL sensors: The flow rate of methane and the $N_2$ carrier gas was controlled by digital mass-flow controllers (MKS Instruments Inc.). A total gas flow rate of 200 ml/min was used. The methane flow was diluted by a $N_2$ flow and the final concentration was calculated based on ideal gas laws. The diluted sample gas flowed through tubing, ca. 1 m length, into the sensor chamber. As illustrated in FIG. 15, the tubing and the sensor chamber were located in a GC oven ("oven"), where the temperature was precisely controlled. The long pathway ensured homogeneous mixing of the sample vapor and the carrier gas. All the QCM used are AT-cut 10 MHz (International Instruments Inc., OK). A MAXTEK RQCM ("RQCM") instrument was used to measure the resonant frequency and the damping resistance.

IL selections: The criteria for IL selections is to avoid the covalent interaction of ILs with PAN substrate but maximum the Van Der Waal interactions, such as electrostatic and hydrogen bonding interactions between PAN and ILs so that the properties and advantageous of ILs as sensing materials will not compromised upon immobilization on PAN. Four identical PAN films are immersed in four 0.1 M IL solutions. The ILs are bmiCS, bmiOMS, P666140MS, and P6666CS. The PAN-IL films were studied for their response to methane via QCM and results are in Table 3.

TABLE 3

Frequency Change After Soaked in IL Solutions (0.1M).

| IL | bmiCS | bmiMS | $P_{6,6,6,14}OMS$ | $P_{6,6,6,6}CS$ |
|---|---|---|---|---|
| Δf (KHz) | 36 | 37 | 22 | 33 |

Figure 16:
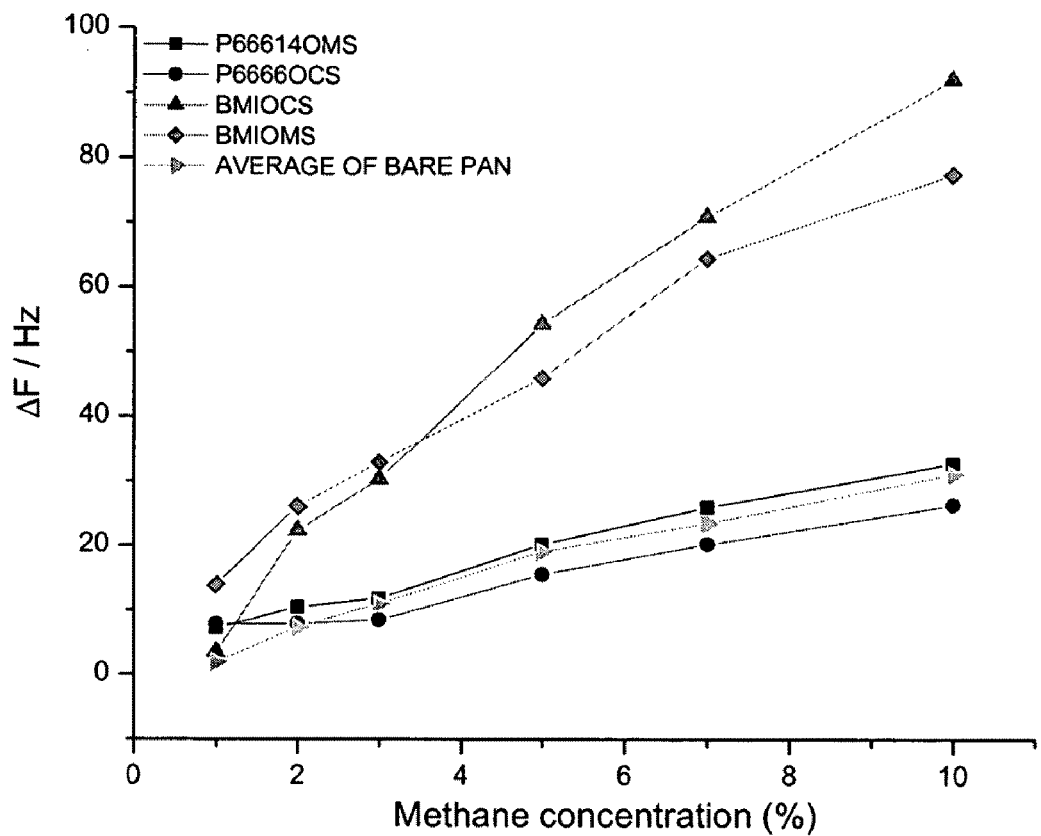
FIG. 16 shows isotherms from different ILs.

Since the PAN film is identical, the total amounts of ILs immobilized on the PAN films should be at the similar order of magnitude. However, the methane sensing signals from PAN/bmiCS and PAN/bmiMS films are much stronger than that from the other two films, see FIG. 16. FIG. 16 shows the isotherms from different ILs. This can be explained by the wettability of PAN. BmiCS and bmiMS are hydrophilic; therefore, they could easily form a very thin film on the interface of a porous PAN film. However, phosphonium based ILs are hydrophobic, they may aggregated to make tiny drops within the PAN film.

Figure 17A:
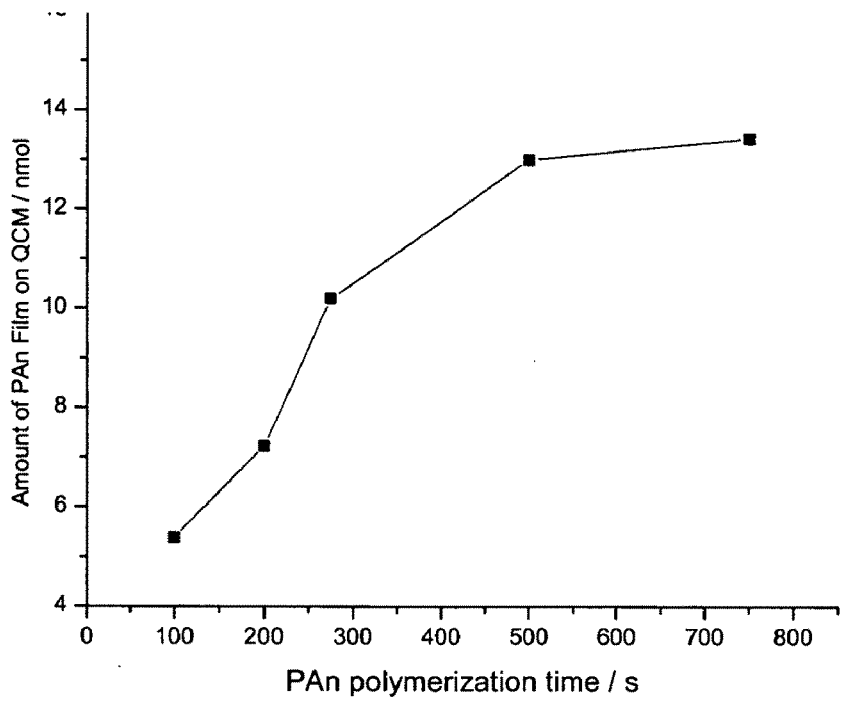
FIG. 17A shows the amount of PAN deposited vs. polymerization time.
Figure 17B:
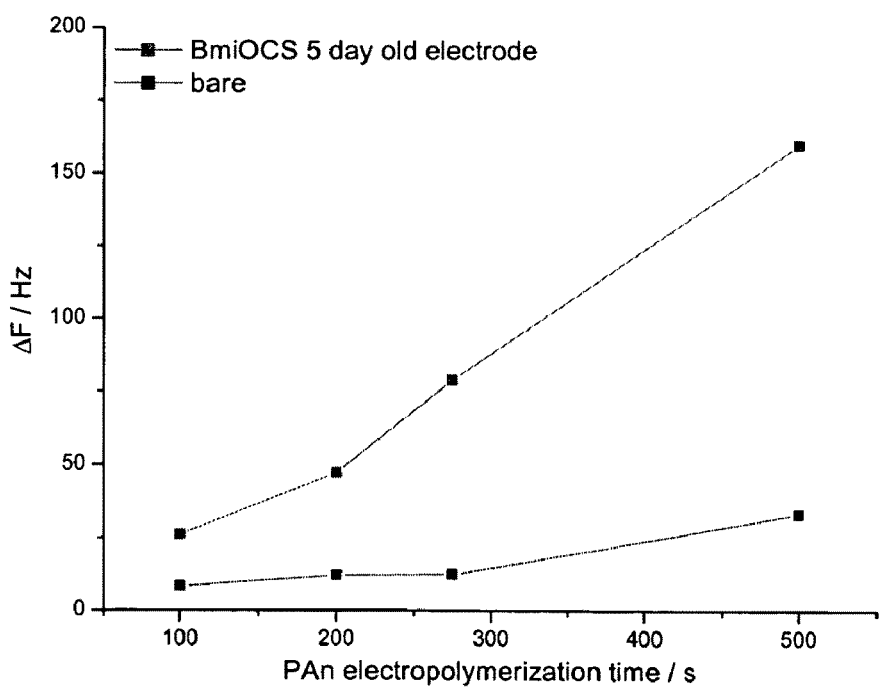
FIG. 17B shows Δf vs. polymerization time.

PAN template thickness effect: PAN film thickness was controlled by varying the time of electrochemcial polymerization at 1.0 V. The resulting films were characterized by Cyclic Voltammetry and the amount of PAN deposited on the electrode was calculated from the CV results using Farady's Law. Assuming the PAN film is homogeneous, the film thickness will be proportional to the amount of PAN at a constant electrode area. FIG. 17 shows the amount of PAN deposited vs. polymerization time (FIG. 17 A) and Δf vs. polymerization time (FIG. 17B). All Films soaked in 0.2 M bmiCS solution and tested at methane concentration of 10%. Shown in FIG. 17, the amount of methane adsorbed increased with increasing film thickness for both bare PAN and IL-PAN film but the amount of increase is much more significantly in the PAN-IL film than that of the bare PAN film. This result shows that the PAN template has very low diffusion barrier for IL molecules and the IL is not only immobilized on the surface of the PAN film, but also can diffuse into the PAN film to make a composite. As a result, methane molecules can absorbed not only on the surface but also into the PAN or PAN/IL film.

Figure 18:
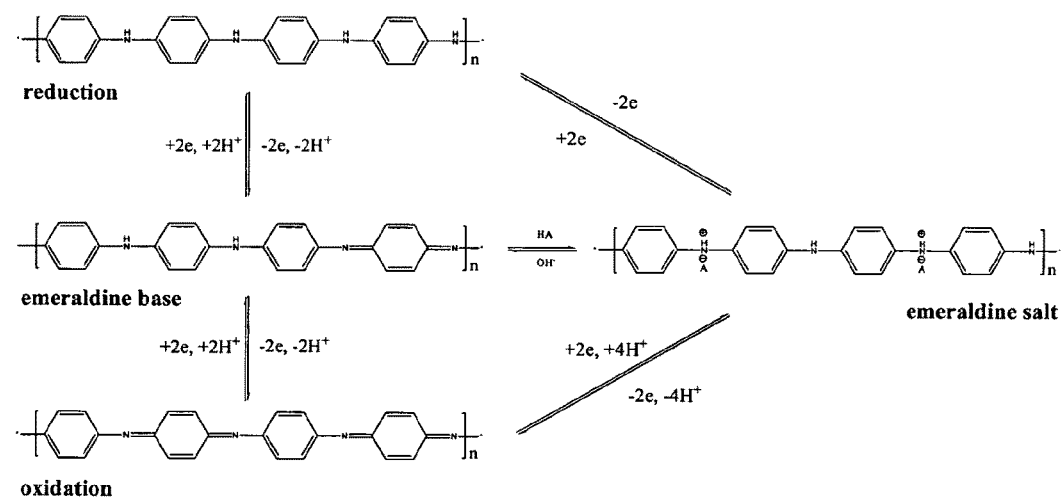
FIG. 18 shows the structures of PAN.
Figure 19:
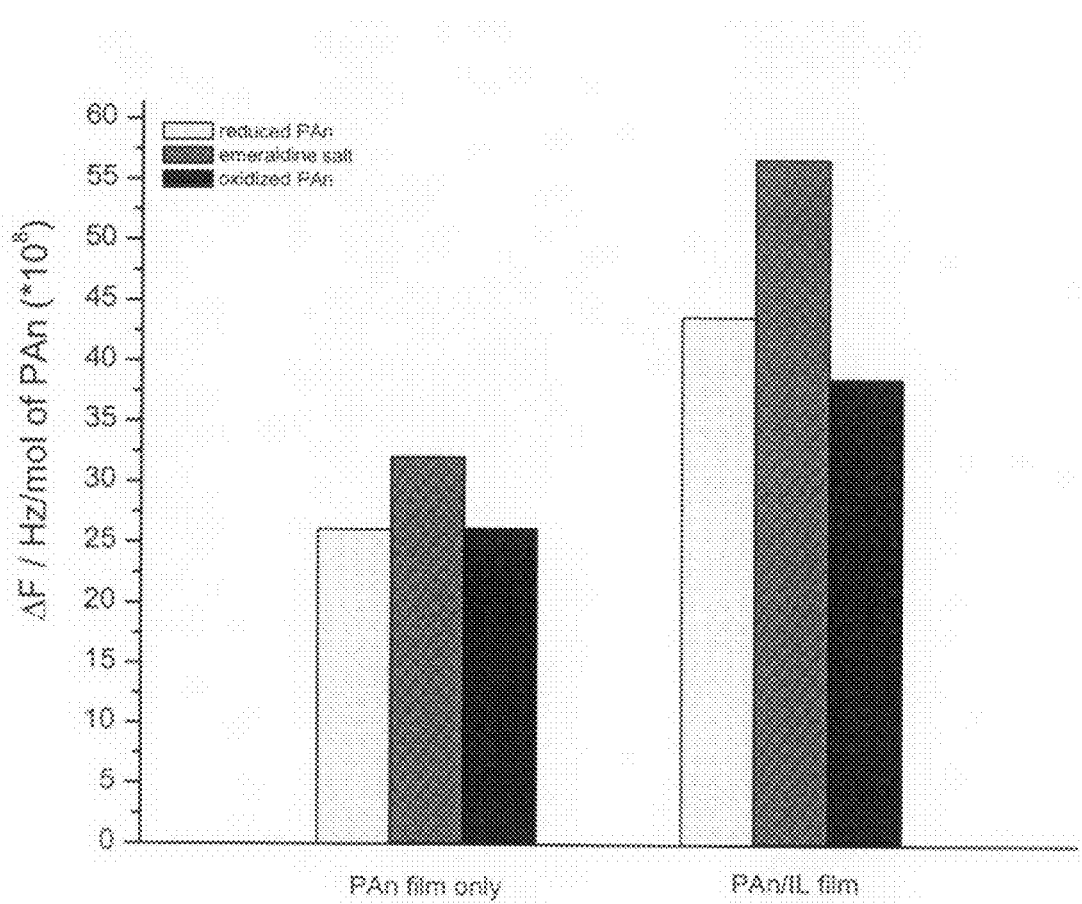
FIG. 19 shows the methane sensing results of the PAN films at different oxidation states before and after the immobilization of IL.

PAN oxidation state effect for IL immobilization: FIG. 18 shows the structures of PAN. As shown in FIG. 18, there are essentially four different redox state of PAN: reduction state, emeraldine base, emeraldine salt, and oxidation state. Oxidation state of PAN will not affect the morphology of the PAN film but it will have different charge. FIG. 19 shows the methane sensing results of the PAN films at different oxidation states before and after the immobilization of IL. Results show that immobilization of IL on the PAN increases the sensitivity of methane detection and the PAN at emeraldine state showed the largest sensitivity for methane. PAN at the emeradine salt state is a charged polymer, the other two states are not. This confirmed our hypothesis that ILs, comprised entirely by ion, will bond favorably with charged PAN and the electrostatic interaction between ILs and charged PAN can facilitate the evenly distribution of IL within a charged polymer resin. To our benefit, the Emeralsine salt and emeraldine base are also more stable than the reduced or oxidized PAN. Therefore, in our work, we used medium oxidized PAN.

Figure 20:
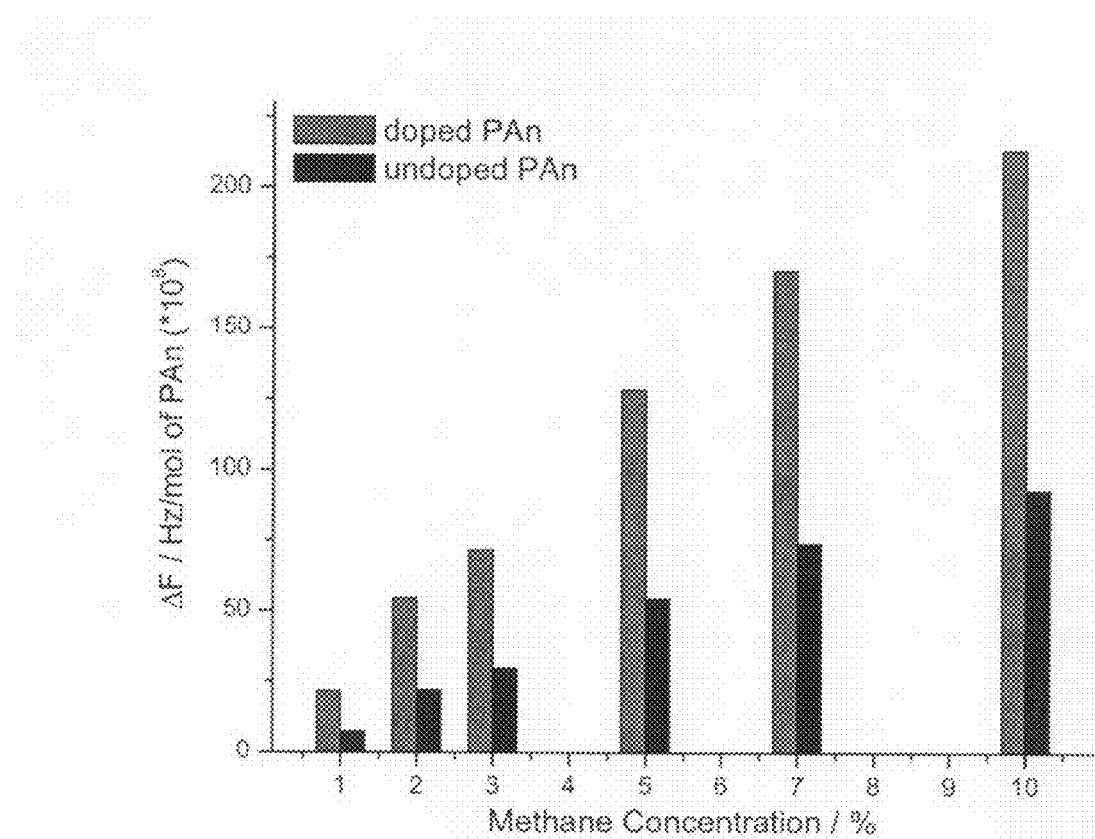
FIG. 20 shows the frequency change of same PAN film at different state: doped and undoped, 10% methane.

The sensitivity of methane adsorption on both PAN emeraldine salt and emeraldine base states was compared, shown in FIG. 20. FIG. 20 shows the frequency change of same PAN film at different state: doped and undoped, 10% methane. The doped PAN/IL film showed larger sensitivity than the undoped PAN/IL film. This is consistent with our prediction that IL, containing cations and anions, is more efficient to absorb into the charged PAN film (i.e. doped PAN) and can spread evenly within the PAN film.

Figure 21A:
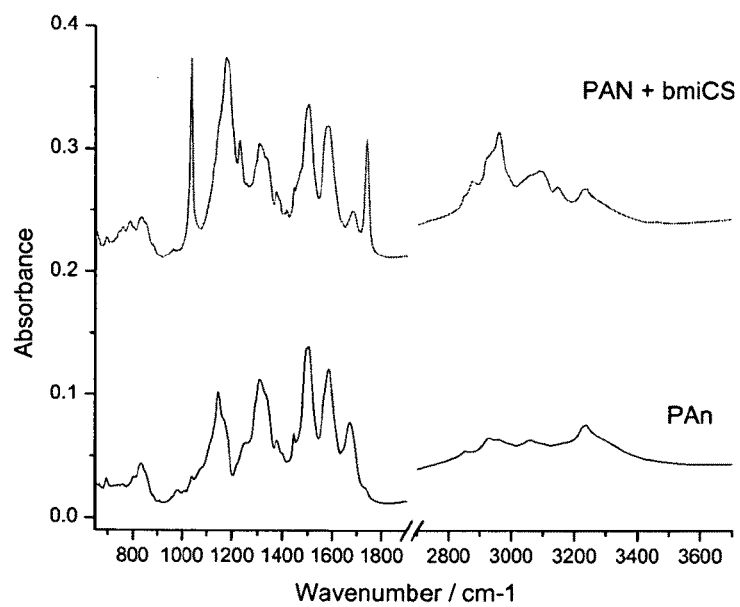
FIG. 21A shows FTIR of PAN and PAN+bmiCS.
Figure 21B:
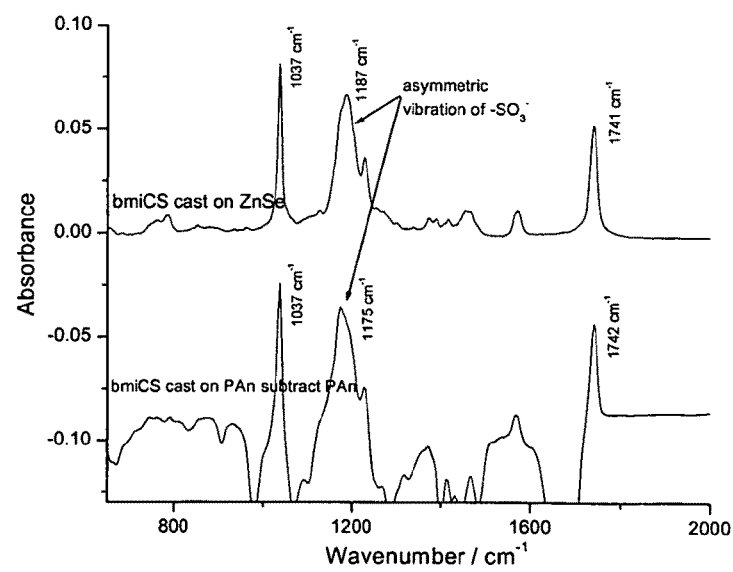
FIG. 21B shows FTIR of bmiCS and PAN+bmiCS subtract PAN.
Figure 22:
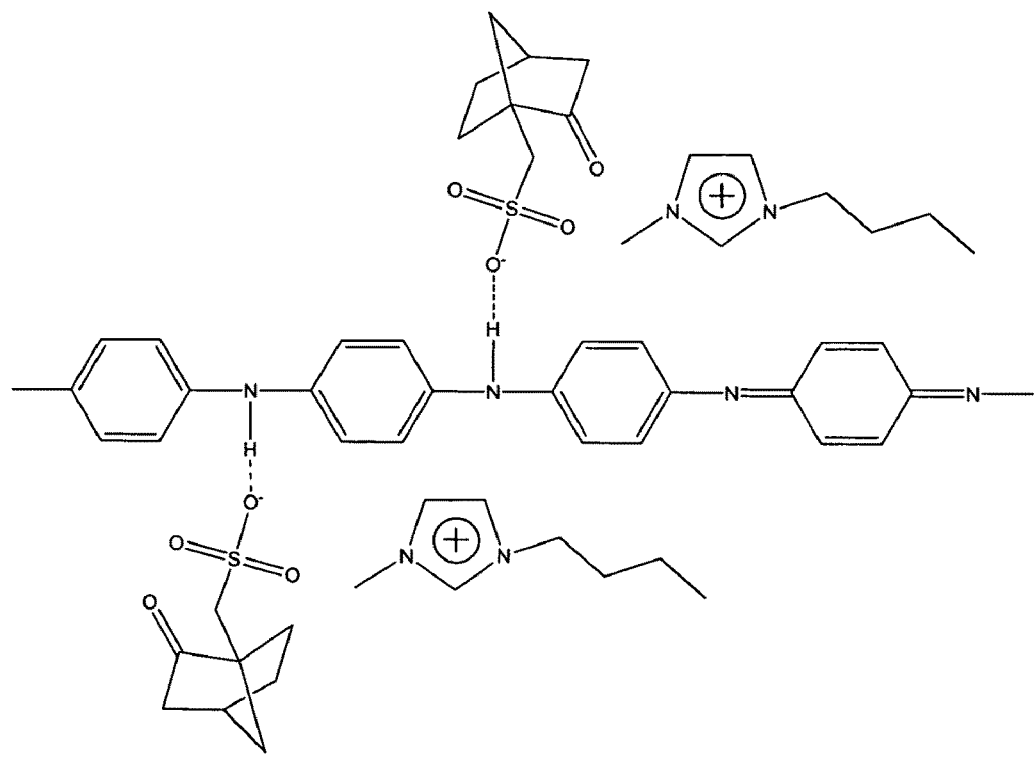
FIG. 22 shows scheme 2.

Characterization of PAN by FTIR and UV: The interaction of PAN and IL bmiCS was further characterized by ATR-FTIR and UV-Vis. A spectrum of undoped PAN cast film was first obtained by ATR method on a ZnSe crystal. All the typical peaks of undoped PAN are showed at 1592,1495, 1305,1163, and 833 $cm^{-1}$, corresponding to the functional groups of PAN. The PAN film was cast from its NMP solution and some of the NMP remained in the PAN film, so that there are peaks at 1688 $cm^{-1}$ and 2930 $cm^{-1}$, which come from the vibration of NMP molecules. When a layer of bmiCS was coated on the PAN film, both the peaks of PAN and the peaks of IL were observed. Since the ATR-FRIT method can only obtain a spectrum of substance within a few microns from the surface of the ZnSe crystal, this result again suggests that the PAN porous structure is wettable by IL and it has little resistance for IL to penetrate through and reach to the surface of ZnSe. Interestingly, when bmiCS was cast on bare ZnSe crystal, the asymmetric vibration of —$SO_3^-$ group of bmiCS gives a peak at 1187 $cm^{-1}$. When bmiCS was cast on a PAN/coated ZnSe crystal, this peak shifted to 1175 $cm^{-1}$. There is no other change in the spectra of bmiCS after interact with PAN. The peaks of PAN did not change. Previously, we have assigned this red shift of the asymmetric vibration of —$SO_3^-$ group to the formation of hydrogen bond. The hydrogen bond could exist between the —$SO_3^-$ group and the amine group of PAN, see scheme 2. This is supported by the fact that the peaks of PAN did not change. The N—H vibration peak around 3300 $cm^{-1}$ of PAN is very broad. The peak position change caused by the formation of the H-bond with —$SO_3^-$ group is not very significant and hard to observe. FIG. 21A shows the FTIR of PAN and PAN+bmiCS; FIG. 21B shows the FTIR of bmiCS and PAN+bmiCS subtract PAN. FIG. 22 shows scheme 2.

Figure 23A:
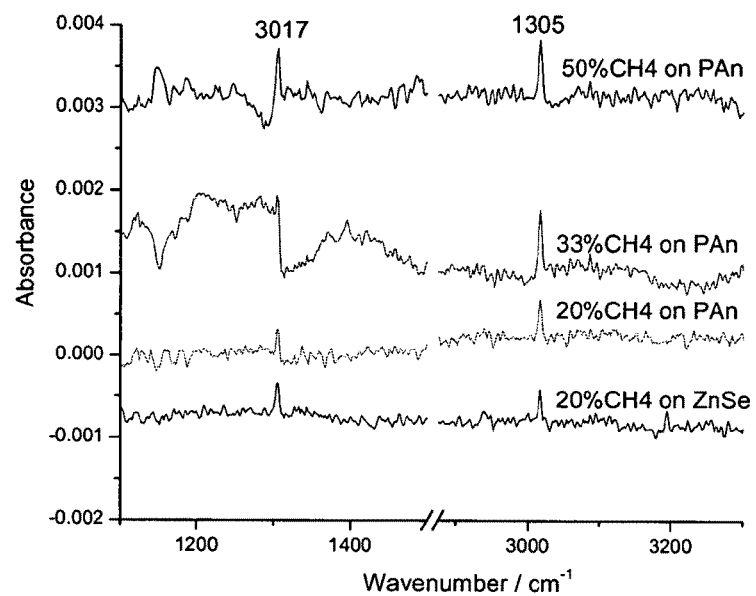
FIG. 23A shows the spectra of methane on ZeSe and on PAN.
Figure 23B:
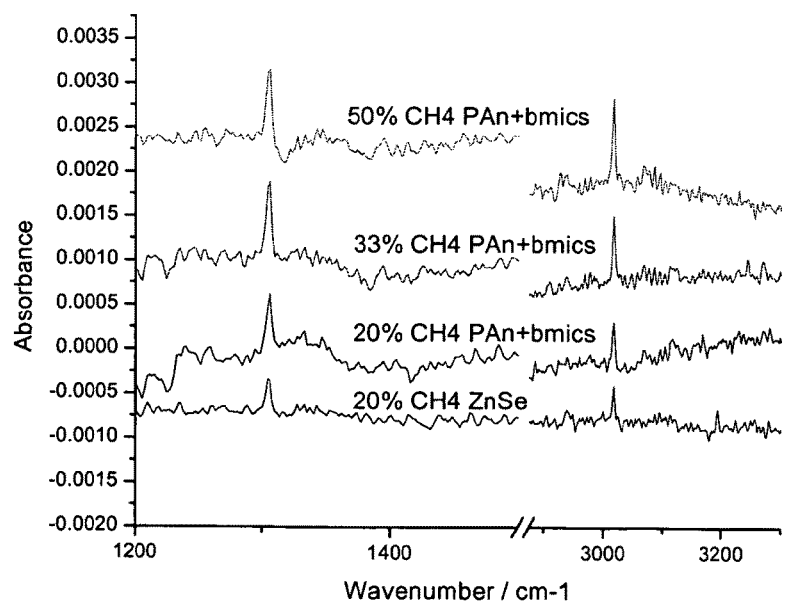
FIG. 23B shows the spectra of methane on ZnSe and on PAN+IL.

The spectroscopy of methane interactions with PAN and PAN-IL films were studied. FIG. 23A shows the spectra of methane on ZeSe and on PAN, FIG. 23B shows the spectra of methane on ZnSe and on PAN+IL. Shown in FIG. 23A, methane has two absorption peaks at 3017 $cm^{-1}$ and 1305 $cm^{-1}$ on bare ZnSe crystal. When a PAN film was cast on ZnSe crystal, there is absorption of methane on PAN. The peak positions did not change. However, the intensities increased slightly by a factor of about 1.23, which is probably due to the porous morphology of PAN that has increased the surface area. Methane is also absorbed into the PAN/IL composite film, FIG. 23B. The peaks position did not changed too. However, if we compare the two lines at the bottom, when IL is applied, the intensity increased by a factor of about 1.5. The applying of IL will not increase the surface area of the film but changed the surface properties. Therefore, the absorption of methane has been enhanced when IL was cast on PAN film and hence a PAN/IL composite film formed. The difference of the two factors (1.23 and 1.5) is not significant because the ATR-FTIR method only record the vibration spectra within a few microns of the ZnSe surface. The overall difference upon methane absorption might be significant if we consider the whole PAN/IL film could be much thicker than microns.

In addition, we can also see that the intensity of the methane peaks increased with the increasing of methane concentration, FIG. 23, which allowed quantitative detection by our sensor. The spectra of methane do not change after adsorption in PAN film and PAN/IL film. Thus the interaction of methane and PAN/IL should be only Van de Waal's interactions. This guaranteed a fast and reversible detection of methane.

Figure 24:
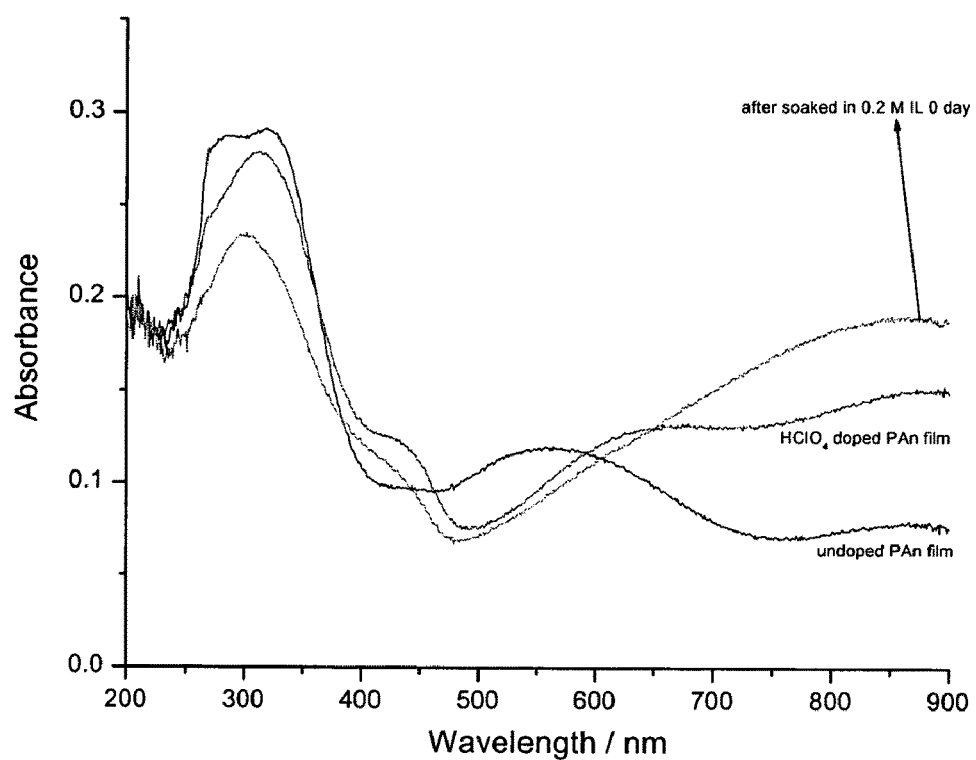
FIG. 24 shows the UV-Vis of PAN film soaked in IL solution.
Figure 25:
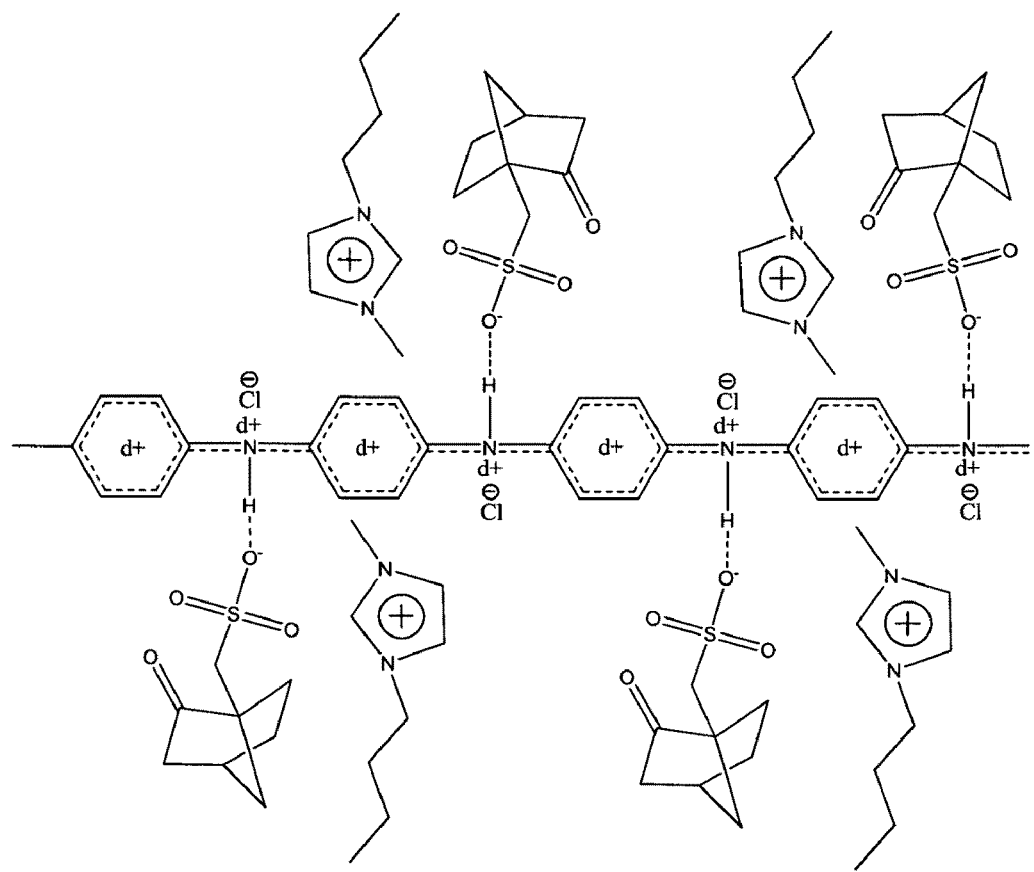
FIG. 25 shows scheme 3.

FIG. 24 shows the UV-Vis of PAN film soaked in IL solution. The UV-vis spectra of three different treated PAN films are shown in FIG. 24. PAN film was electrochemically deposited on an ITO electrode and then dedoped in $NH_4OH$ solution. The UV-vis spectra of dedoped PAN are very typical. There are absorption bands around 300 nm ($\pi_b-\pi_b'$) and 550 nm ($\pi_b-\pi_q$). After doped with $HClO_4$ solution, the band around 300 nm became weaker; a shoulder around 415 nm (N-$\pi$) showed up, the band around 550 nm shifted to about 650 nm, and there is high profile absorption beyond 700 nm (long range conjugation). All these characters are come from the doped PAN. After soaking in 0.2 M IL solution, the band around 650 nm totally disappeared, and the absorption between 700 and 900 nm are even higher. These may indicate that the doped PAN interacts with IL and enhance the long-term conjugation of PAN backbone. As we have proposed the formation of H-bond by the FTIR results, this interaction of doped PAN and IL might be described by Scheme 3, as shown in FIG. 25. These FTIR and UV results suggest that there are molecular interactions between IL and PAN which increase the wettability of IL on the PAN film. In each repeat units of PAN, there are two —NH— groups when PAN is dedoped. While there are four —NH+-groups when PAN is doped. Therefore, doped PAN has larger capacity to form H-bond with IL. This may explain why doped PAN has better sensitivity than dedoped PAN when both of them were used to immobilized IL and detect methane.

Figure 26:
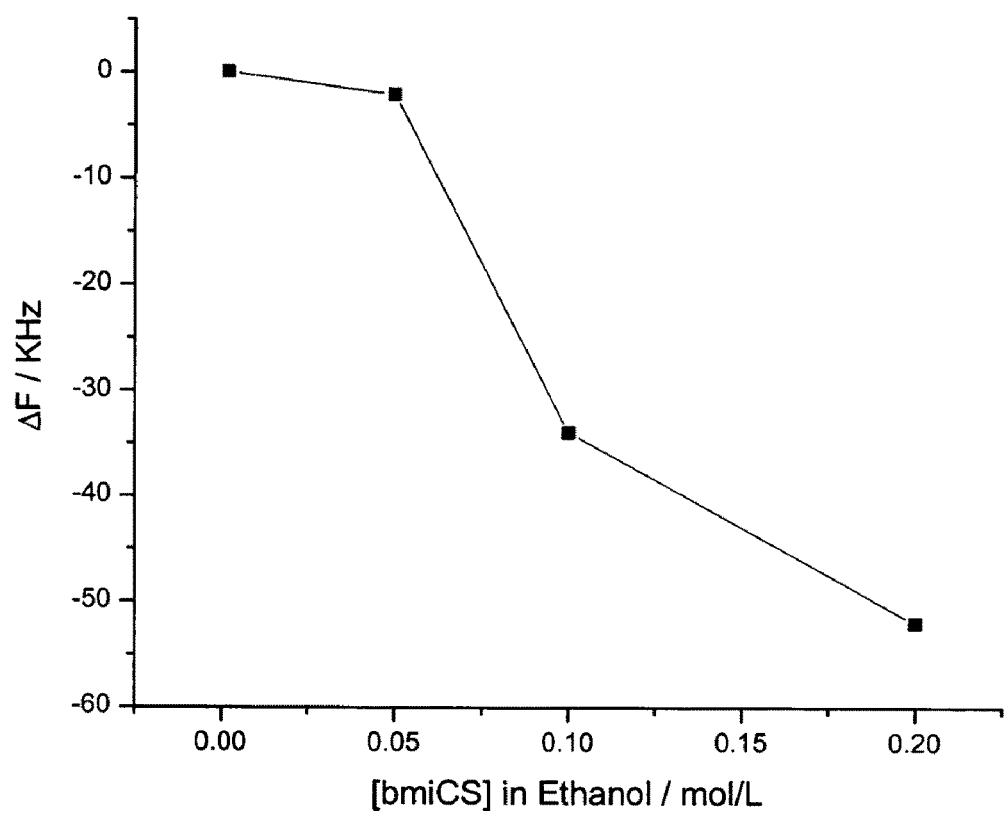
FIG. 26 shows the Δf caused by IL loading as a function of [bmiCS].

Sensitivity vs. amount of IL loaded: The optimum condition for PAN-IL film were used to prepare four identical PAN film (at 1.0 V vs. SCE, 500 seconds) to study IL loading effect on the methane sensitivity. Each of them were soaked overnight in 0.002M, 0.05M, 0.1 M and 0.2M bmiCS solutions in ethanol, respectively. FIG. 26 shows the $\Delta f$ caused by IL loading as a function of [bmiCS]. Shown in FIG. 26, the higher the IL coating concentration, the bigger the frequency shift when methane adsorped. The resonance frequency of the PAN covered QCM is not significant in the lowest IL coating solution: 0.002 M bmiCS solution but the frequency decrease from 2 KHz (soaked in 0.05 M bmiCS) to 52 KHz (soaked in 0.2 M bmiCS). This indicates the amount of the IL loaded is related to the IL concentration. When the IL solution concentration is 0.5 M or larger, there is too much IL absorbed in the PAN film. Oscillation of the QCM can not be established.

Figure 27A:
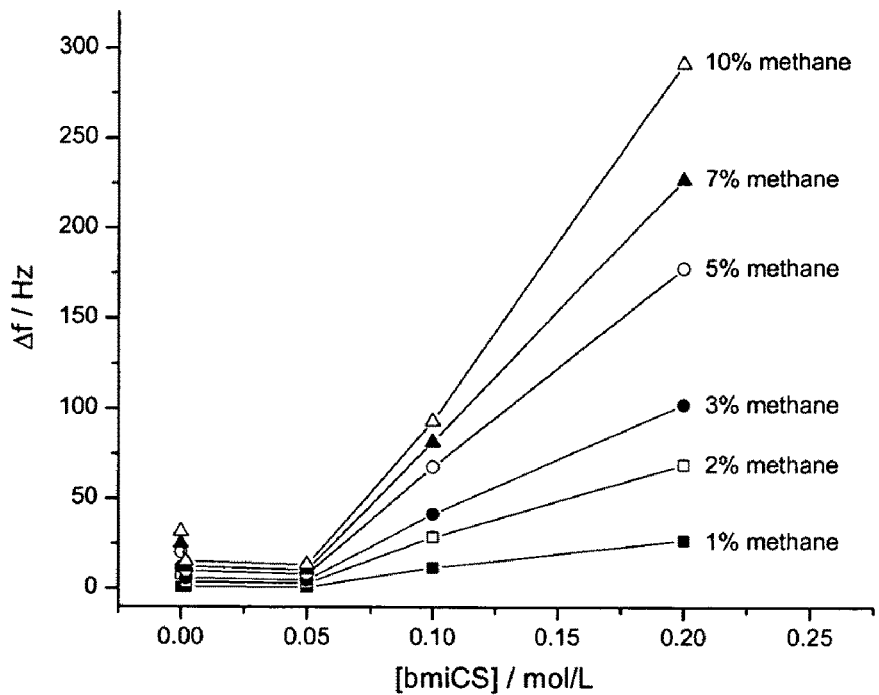
FIG. 27A shows the Δf caused by methane absorption vs. [bmiCS]

FIG. 27A shows the $\Delta f$ caused by methane absorption vs. [bmiCS], and (b) $\Delta f$ caused by methane absorption vs. methane concentration of PAN films before and after treated in IL solutions. FIG. 27 showed the quantitative study of the sensitivity of methane vs. bmiCS concentration. In low IL coating solution, i.e. 0.002 M and 0.05 M bmiCS solution, there is no significant change in methane absorption, comparing with that on PAN film itself. However, when higher concentration solutions of bmiCS, e.g. 0.1 M or 0.2 M, were used to coat PAN, the absorption capacity of the PAN/IL film significantly increased. For example, the response is as larger as about 291.5 Hz for 10% methane. In a control experiment, PAN film was modified in pure ethanol overnight; the absorption of methane was similar to the bare PAN film and no enhance sensitivity was observed after the ethanol was dried.

Figure 28A:
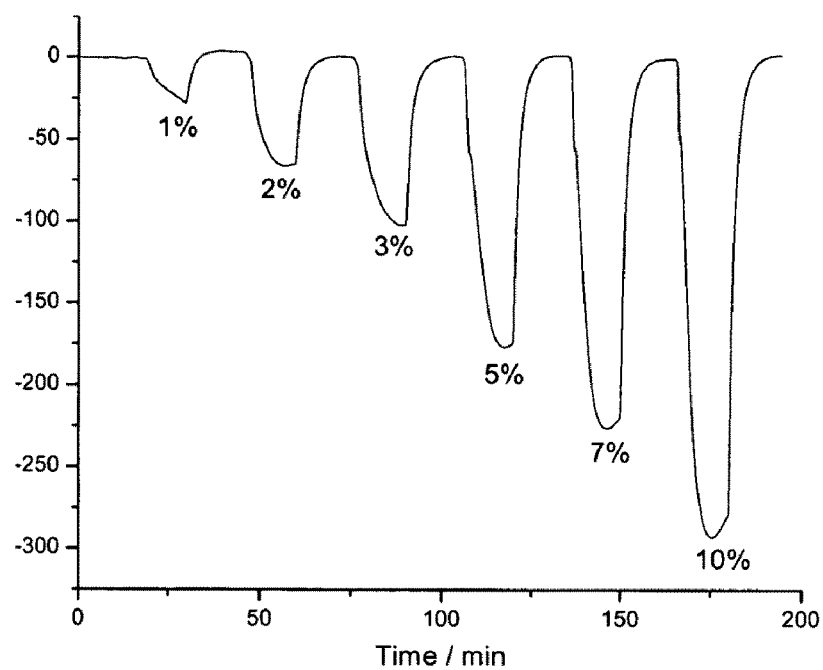
FIGS. 28A and 28B shows the time course response (Δf) curve of PAN/bmiCS (0.2) film response to methane with varied concentration at room temperature.
Figure 28B:
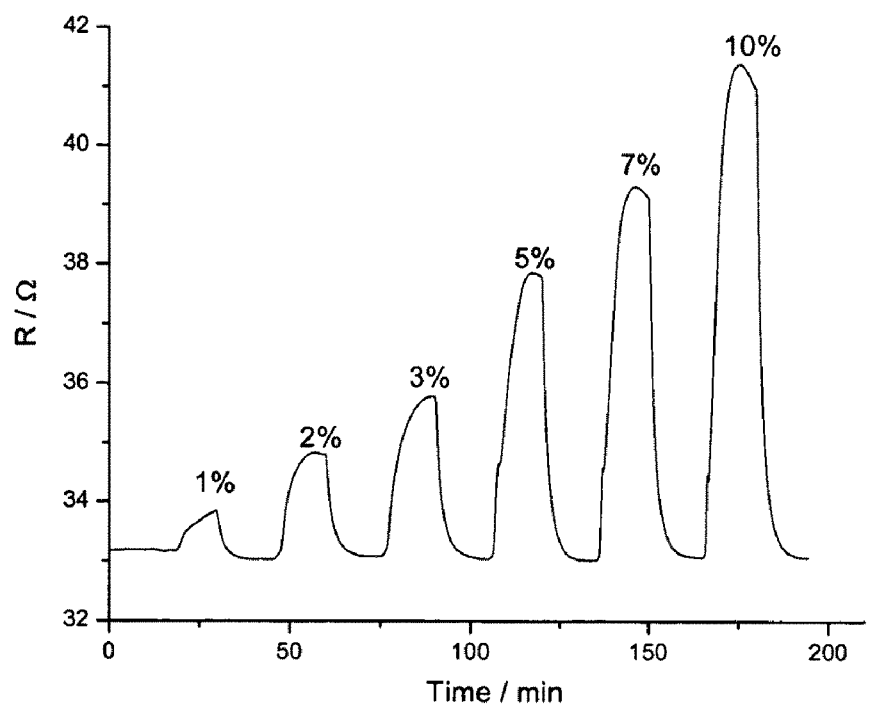

The PAN-IL film shows not only enhanced sensitivity for methane detection but also excellent reversibility. FIGS. 28A and 28B show the time course response ($\Delta f$) curve of PAN/bmiCS (0.2) film response to methane with varied concentration at room temperature. FIGS. 28A and 28B are representative frequency shift and resistance shift sensorgrams of the PAN/bmiCS film response to methane concentration from 1% to 10%. The adsorption and desorption of methane on PAN/bmiCS film is reversible. Each time the methane gas was switch on or off, the response reaches the equilibrium value in less than 10 min (except at very low concentrations for example 1%). This response time include the time to fill the sensor's chamber, which is about three minutes. In our previous reports with pure IL films the response is faster, about 5 min. The longer response time is because the PAN/IL film is much thicker than the cast IL film in the previous reports. It need more time for the dissolved gas molecules diffuse within the film to reach equilibrium. However, the cost of the response time is worthwhile because the PAN/bmiCS film showed significant improvement for the sensitivity to the methane gas. The lower explosion limit if methane is 5%. At this concentration, the frequency change is about 178 Hz. The response is close to 30 Hz at 1% of methane and 300 Hz at 10% of methane. The base line has about 0.2 Hz noise. Therefore, assuming a detectable signal/noise ratio of ten, we can convincingly detect about a 2 Hz frequency-change, which corresponds to about 0.07% of methane. That means a detection limit of about 400 ppm, or 500 mg/m$^3$. This value is significantly lower than the reported detection limits with QCM/IL sensors. In these reports, the detection limits are larger than thousands ppm for organic vapors with much larger molecular weight than methane. This value is also lower than the occupational exposure limit of methane, which is 1000 ppm.

Figure 27B:
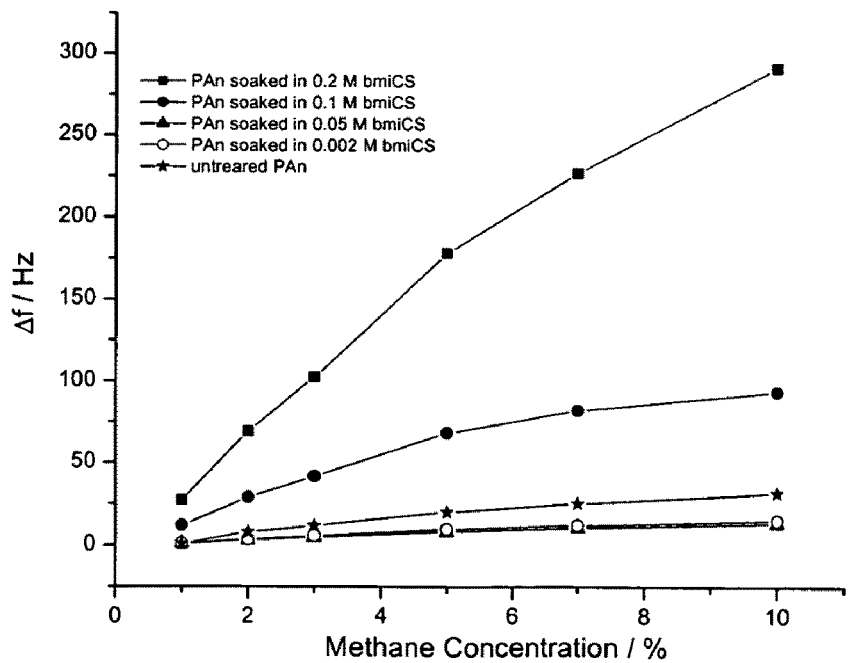
FIG. 27B shows Δf caused by methane absorption vs. methane concentration of PAN films before and after treated in IL solutions.
Figure 29A:
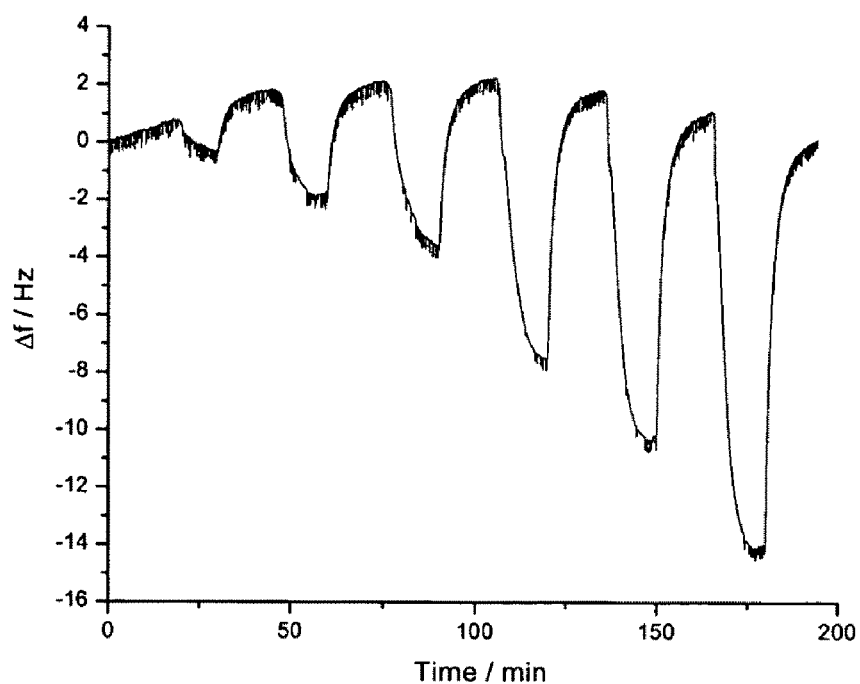
FIGS. 29A and 29B shows the time course response (Δf) curve of PAN/bmiCS (0.002) film response to methane with varied concentration at room temperature.
Figure 29B:
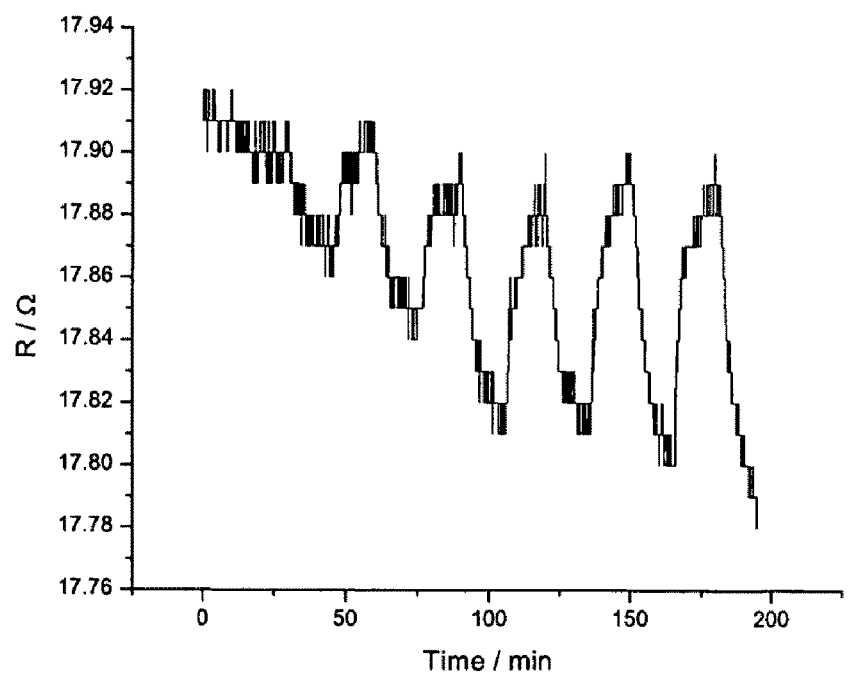

An IL methane gas sensor was successfully developed with an experimental detection limits less than 0.1% and linear range of 0.1% to 20% of methane. 0.1% methane is about 400 ppm which is the best detection limits available with piezoelectric devices. FIG. 27B shows a dynamic linear range of the methane detection to about 5% in which the response is proportional to the methane concentration. At high concentrations, however, the responses deviate from the linear relationship. This may be caused by saturation of the methane with the IL film. The modulus or viscosity change of the PAN/IL film upon absorption of methane could also contribute to the deviations. FIG. 28B shows the damping resistance change vs. methane concentration. When a PAN film is treated in 0.2 M bmiCS solution, the resistance change is as large as 10 Ω at 10% of methane. However, when the PAN film is treated in a very dilute bmiCS solution, 0.002 M, the resistance change upon absorption of methane is very small, less than 0.2 Ω, see FIG. 29. FIG. 29 also shows the frequency change of the PAN/IL film treated in 0.002 M bmiCS solution. FIG. 29 shows the time course response ($\Delta f$) curve of PAN/bmiCS (0.002) film response to methane with varied concentration at room temperature. The sensorgram resembles the features in FIG. 28A, but much smaller in magnitude.

Figure 30A:
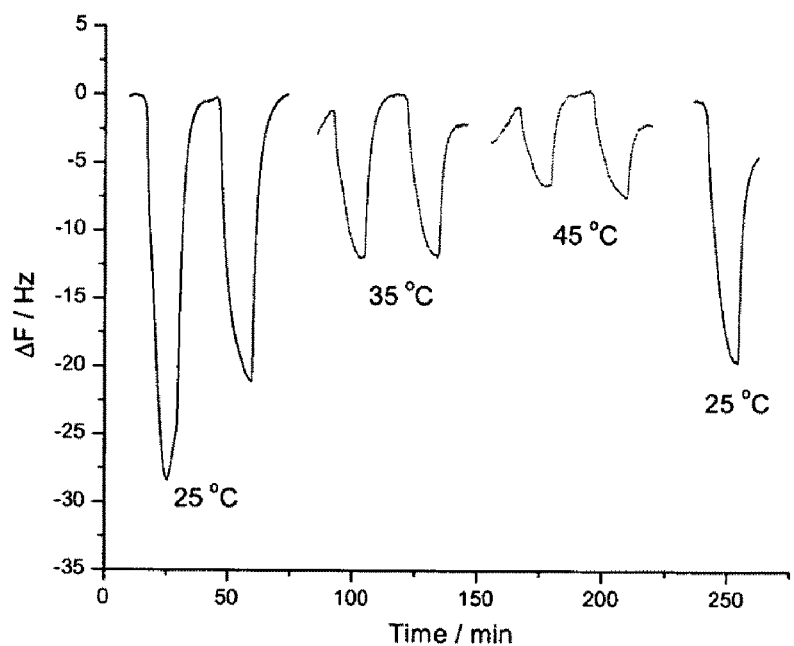
FIG. 30A shows Δf vs. time at various temperatures.
Figure 30B:
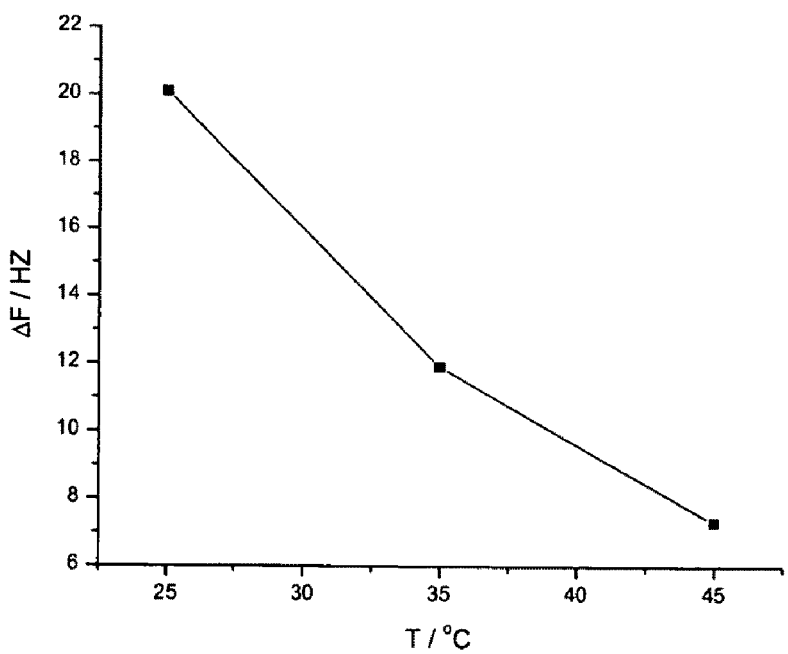
FIG. 30B shows the Δf plotted vs. temperature, at methane concentration of 3%.
Figure 31A:
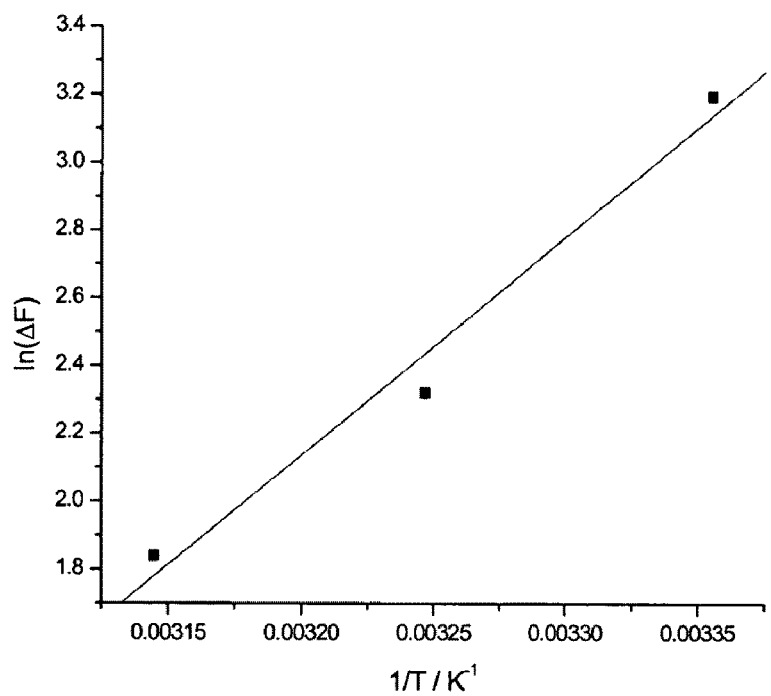
FIG. 31A shows ln(Δf) vs. 1/T.
Figure 31B:
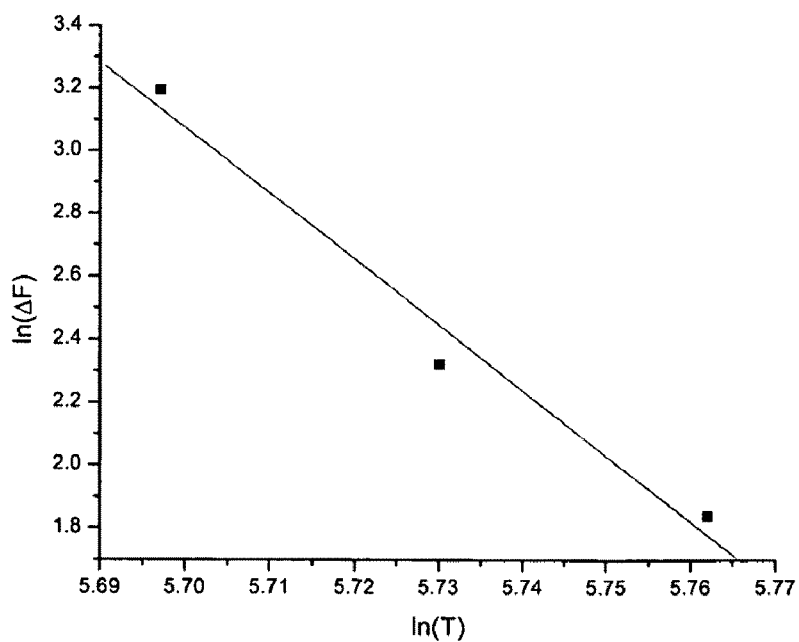
FIG. 31B shows the ln(Δf) vs. ln(T).

Interactions of methane with IL-PAN film at various temperatures: FIG. 30A shows $\Delta f$ vs. time at various temperatures, and FIG. 30B shows the $\Delta f$ plotted vs. temperature, at methane concentration of 3%. The results from a doped PAN film soaked in 0.2 M IL solution responses to 3% methane at different temperature are shown in FIG. 30. When the temperature increased from 25° C. to 45° C., the response reduced to about ¼ of the original value. When the temperature was reduced to 25° C. again, we can recover the response. So the PAN/IL film is stable within this temperature range and the temperature effect is reversible. In our previous reports, we have calculated the AH and AS based on the slopes of ln(Xi) vs 1/T and ln(Xi) vs. ln(T) according to van't Hoff equation. In this work, we cannot calculate the values of the molar fraction, Xi. But the Xi is proportional to the frequency shift, if we still use the Sauerbrey Equation. Therefore, the ln($\Delta f$) vs. 1/T and the ln(xi) vs 1/T should have the same slope but different intercept; the ln($\Delta f$) vs. ln(T) and the ln(xi) vs ln(T) should also have the same slope but different intercept. FIG. 31A shows ln($\Delta f$) vs. 1/T, and FIG. 31B shows the ln($\Delta f$) vs. ln(T). FIG. 31 is used to calculate AH and AS. FIGS. 31A and 31B showed the ln($\Delta f$) vs. 1/T and the ln($\Delta f$) vs. ln(T) relationship. We can calculate the $\Delta H$ and $\Delta S$ according to the slopes. The absorption enthalpy (AH) of methane in PAN/bmiCS is −53.5±7.9 KJ/mol. The absorption entropy is 173.7±27.4 J/K·mol. These values are much larger than those reported by groups in the literature.

Selectivity results: Various pairs of conductive polymer/polyelectrolyte and IL composites can be imagined. The value and importance of the wide range electrodes modified by immobilization of a single species (conductive polymer or polyelectrolyte) is widely acknowledged and we believe that using appropriately chosen pairs of immobilized species can produce unique surfaces with valuable chemical properties (e.g. controlled porosity, orientation and tunable thickness).

In some embodiments, a polymer (including, but not limited to a conductive polymer, such as polyaniline) can be formed from monomer structures having functional side groups. Thus, conductive polymer templates having additional functional groups can be generated for binding the IL to a surface. The functional groups can be used to immobilize ionic liquids with preferred orientation via various molecular interactions (i.e. hydrogen bond, p-p, dipolar, ionic. etc.) of ionic liquids and conductive polymer functional groups.

EXAMPLES 4-11

EQCM Sensors

The following examples illustrate the disclosed apparatus and methods related to EQCM sensor fabrication, detection, selectivity, and sensitivity, but are not intended to limit the scope of any claims thereto.

In the following examples, the ionic liquid butylmethylimidazolium tetrafluoroborate (BMIBF$_4$) was purchased form Acros Organics, Inc. (Geel, Belgium) with over 98% purity and was used as received. Nitroaromatic compounds including 1-ethyl-2-nitrobenzene (ENB), 2,4-dinitrotoluene (2,4-DNT), 3,4-dinitrotoluene (3,4-DNT), and 2,6-dinitrotoluene (2,6-DNT) were purchased from Aldrich Inc. (St. Louis, Mo.) and also were used as received without any further purification.

EXAMPLE 4

Sensor Fabrication

Figure 32A:
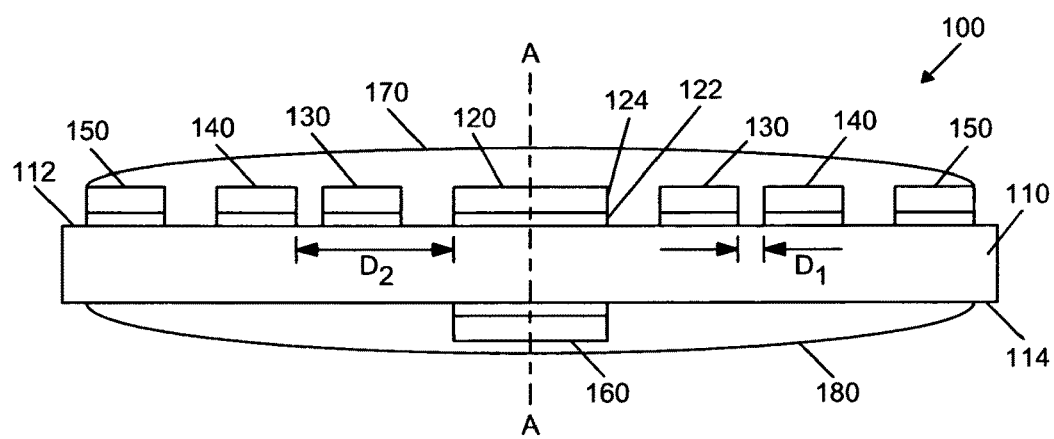
FIG. 32. Cross-sectional (A), top (B), and bottom (C) view of an electrochemical piezoelectric gas sensor according to the disclosure.
Figure 32B:
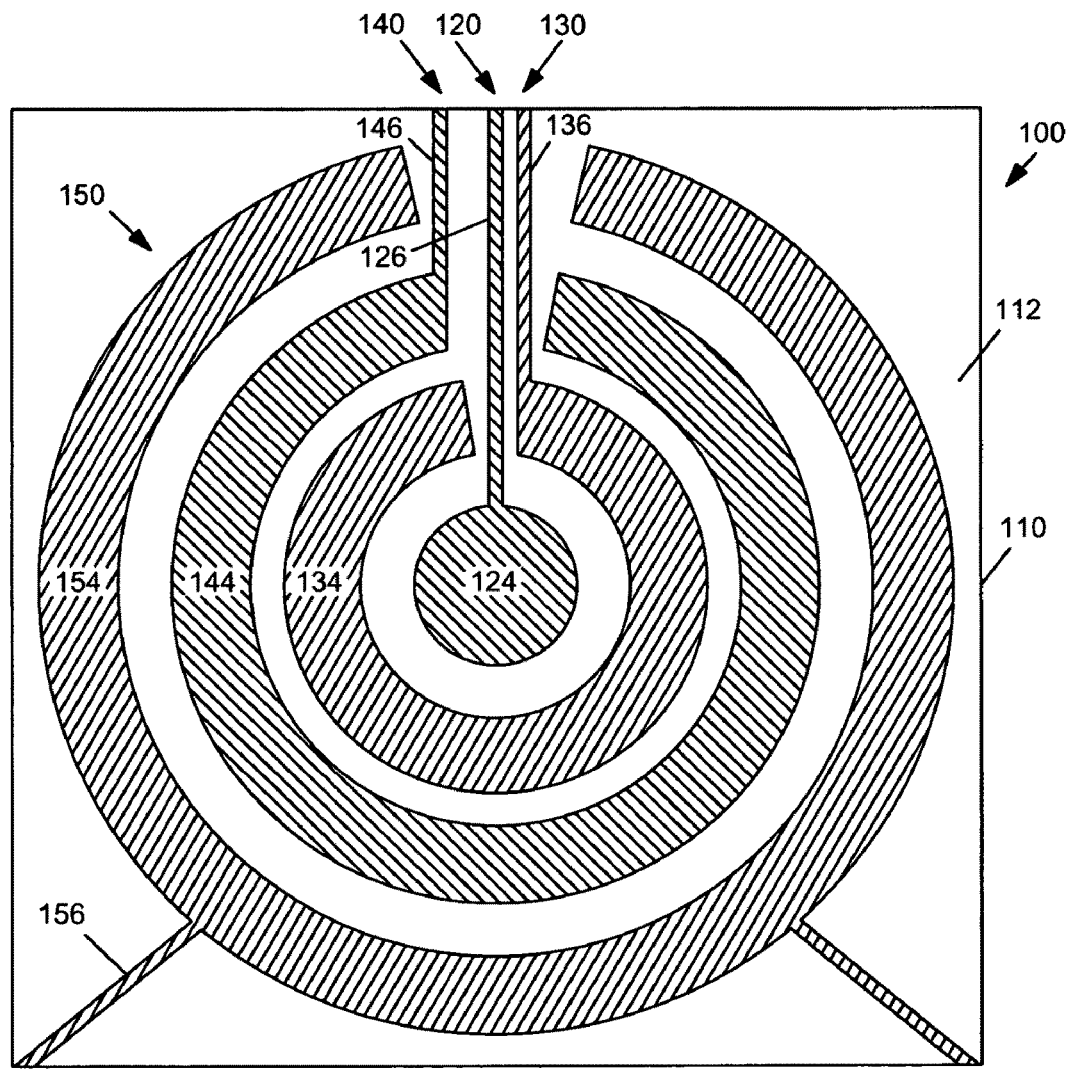
Figure 32C:
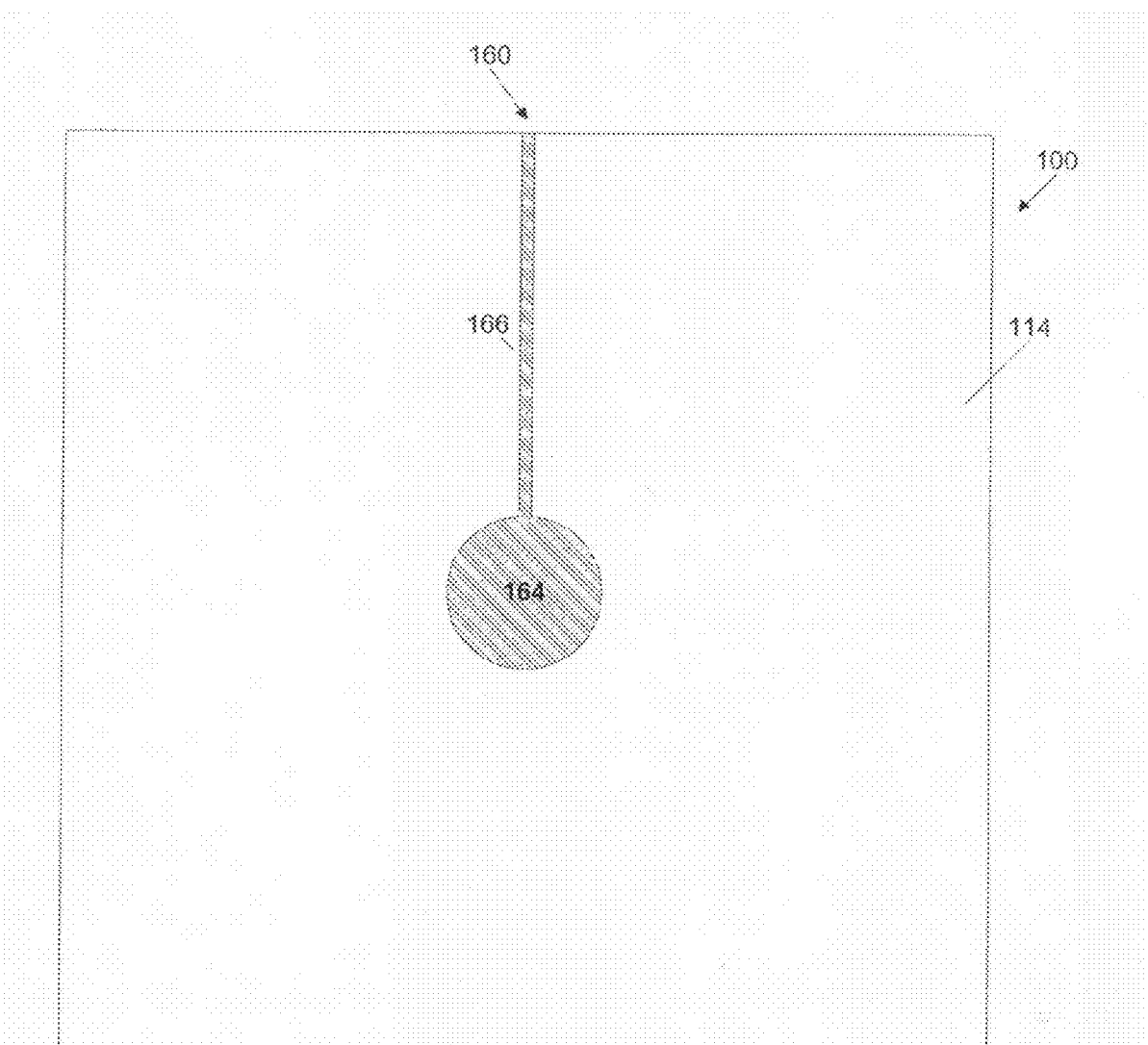

An electrochemical piezoelectric sensor 100 according to the disclosure is illustrated in FIGS. 32A (side cross-sectional view), 32B (top view), and 32C (bottom view). The sensor 100 includes a substrate 110 having a top surface 112 and a bottom surface 114. A central, square-shaped portion of the substrate 110 is shown in FIGS. 32B and 32C. In general, however, the substrate 110 can have any convenient shape, for example including a thin disk (e.g., shown in FIG. 35B) or a rectangular shape (e.g., shown in FIG. 42B), and the substrate 110 can have more than one sensor/set of electrode elements (e.g., shown in FIG. 42B). The terms "top" and "bottom" are arbitrary, and generally denote opposing surfaces of the substrate 110, with the top surface 112 generally having an ionic liquid 170 applied thereto. The ionic liquid 170 is preferably in the form of a thin film that is sufficiently thick to permit both the electrochemical and the piezoelectric analysis of analytes (e.g., explosive vapor molecules) absorbed into the ionic liquid film. In some embodiments, the sensor 100 can have another ionic liquid 180 applied to the bottom surface 114. The ionic liquid 180 also is preferably in the form of a thin film and can be the same or different ionic liquid species as the ionic liquid film 170. Given the electrode configuration of the sensor 100, the ionic liquid 170 can be used for both piezoelectric and/or electrochemical measurements, and the ionic liquid 180 can be used for piezoelectric measurements. In a two-film embodiment, piezoelectric measurements can be limited to the ionic liquid 180 to limit the effect of analyte destruction/modification due to the application of electrochemical voltages or currents. For either or both of the ionic liquids 170, 180, the thin film is not generally entirely uniform in height, although a suitable height (or average height) over the electrode area can range from about 60 μm to about 500 μm, about 80 μm to about 400 μm, about 100 μm to about 400 μm, or about 100 μm to about 200 μm. Alternatively, the ionic liquid 180 film can be substantially thinner (e.g., about 50 μm or less, about 1 nm to about 5 μm, or about 5 nm to about 500 nm), because it is generally limited to piezoelectric measurement. The substrate 110 can be formed from any suitable material when the sensor 110 is only intended to perform electrochemical measurements (e.g., a non-conductive material, a glass substrate). When the sensor 110 is intended to perform electrochemical and piezoelectric (e.g., QCM) measurements, the substrate 110 is suitably formed from any piezoelectric material (e.g., quartz, in particular crystalline α-quartz). The substrate 110 can have any suitable thickness based on the desired fundamental resonant frequency of the piezoelectric substrate 110, for example a thickness ranging from about 50 μm to about 500 μm, about 80 μm to about 400 μm, or about 100 μm to about 200 μm.

As illustrated, the sensor 100 includes a plurality of electrodes, including general disk- and ring- (or annular-) shaped electrodes. A top disk electrode 120 on the top surface 112 of the substrate 110 opposes a bottom disk electrode 160 on the bottom surface 114 of the substrate 110. Preferably, the disk electrodes 120, 160 are substantially aligned, for example along an axis A-A (e.g., an axis of rotation of a disk-shaped substrate, or other line generally perpendicular to the substrate 110). The top surface 112 of the substrate 110 further includes a first ring electrode 130, a second ring electrode 140, and a third ring electrode 150 at increasing outward radial positions away from the disk electrode 120 and spaced away from each other. The third ring electrode 150 can be used as a redox-recycling electrode for detection of compounds with reversible redox behavior to amplify the amperometric current signal. Generally, the first ring electrode 130 preferably includes a portion that at least partially surrounds a portion of the top disk electrode 120, and the second ring electrode 140 preferably includes a portion that at least partially surrounds a portion of the first ring electrode 130. Similarly, the third ring electrode 150 preferably includes a portion that at least partially surrounds a portion of the second ring electrode 140. In the specific embodiment illustrated, the disk electrodes 120, 160 include substantially disk-shaped portions 124, 164 and wiring/lead portions 126, 166 (e.g., for electrical connections to external power supplies/measuring devices). Similarly, the ring electrodes 130, 140, 150 include substantially ring-shaped portions 134, 144, 154 and wiring/lead portions 136, 146, 156 (e.g., also for external electrical connections). Thus, in the illustrated embodiment, the first ring-shaped portion 134 at least partially surrounds the top disk-shaped portion 124, and the second ring-shaped portion 144 in turn at least partially surrounds the first ring-shaped portion 134. An electrode that at least partially surrounds another electrode preferably does so to the largest possible extent (e.g., the exterior electrode encompassing about or at least 70%, 80%, or 90% of the available area/circumference around the interior electrode), taking into account the need to provide spatial access for wiring/lead electrode portions to the interior electrode.

The spacing and arrangement of the electrodes are preferably selected to improve the sensitivity and stability of the sensor 100. A first distance $D_1$ between the ring electrodes 130, 140 (or between the corresponding ring-shaped portions 134, 144) is advantageously minimized to reduce IR drop when the two electrodes serve as working and counter electrodes. The limiting current at steady state for microelectrodes is $i_\infty = nFDcA/a$. Evidently, the current response of microelectrodes is independent of the diffusion layer thickness and does not suffer from interferences caused by changes of the natural convection in the sample solution. However, due to their very small surface area, microelectrode currents can be very small, and careful optimization of a sensor's geometric parameters can be used to design useful microelectrodes or arrays for electrochemical detection. The ability to control the electrode geometry with great precision via microfabrication techniques to develop a multichannel microelectrode array including an assembly of independent concentric microband electrodes for redox recycling can further improve the detection limits for target species that can be oxidized and reduced multiple times. Thus, when the two electrodes serve as working electrodes for redox recycling, the spacing between the two electrodes is preferably as small as possible to facilitate fast diffusion and increase the efficiency of the redox recycling. However, redox recycling methods for signal amplification only apply for those redox reversible compounds. For example, the first distance $D_1$ suitably ranges from about 10 μm to about 200 μm, about 20 μm to about 100 μm, or about 30 μm to about 70 μm. A second distance $D_2$ between the disk electrode 120 and the ring electrode 140 (or between the corresponding disk-shaped portion 124 and the ring-shaped portion 144) is advantageously maximized to limit diffusion of any absorbed analytes between the two electrodes when they serve as counter and reference electrodes. The second distance $D_2$ suitably is about 500 μm or more, for example ranging from about 500 μm to about 5000 μm, about 600 μm to about 3000 μm, or about 800 μm to about 2000 μm.

Figure 33A:
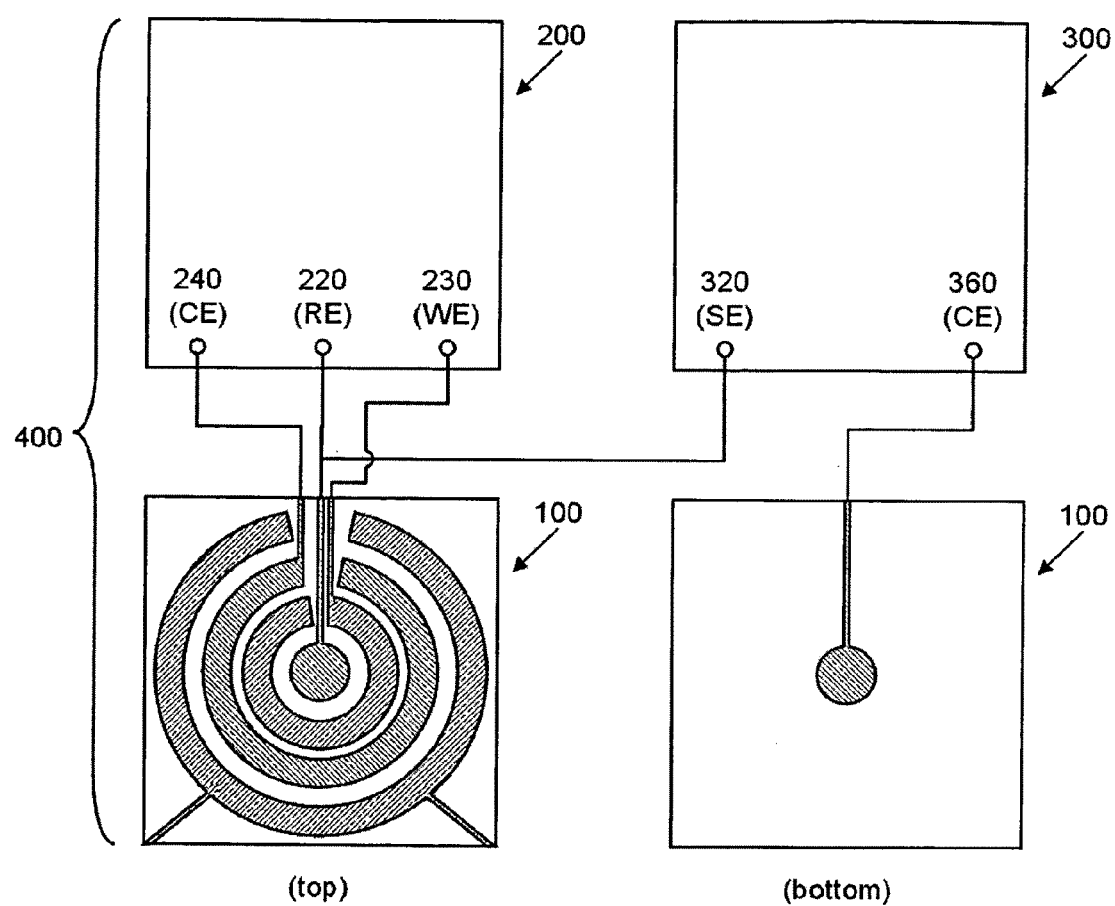
FIG. 33. Schematics of an electrochemical piezoelectric gas sensing systems (A: voltammetry connections; B: impedance spectroscopy connections) according to the disclosure (top and bottom views of the same gas sensor 100 are illustrated for clarity).

The sensor 100 can be incorporated into an electrochemical piezoelectric sensing system 400, for example a system for voltammetric measurement as illustrated in FIG. 33A. The sensing system 400 includes the sensor 100 electrically connected to a potentiostat 200 (or other means for supplying a voltage and measuring an electrical current) and an AC voltage source 300. In FIG. 33A the top and bottom views of a single sensor 100 are shown to illustrate the electrical connections between the potentiostat 200 and the voltage source 300; however, a plurality of sensors (not shown) can be included in the sensing system 400, for example to form a multi-sensor array (e.g., where different sensors in the array can have ionic liquid films with varying ionic liquid species, film thicknesses, binding means, etc. to provide sensor array measurement patterns for pattern recognition and analyte identification). The disk electrodes 120, 160 are used for QCM measurements and are electrically connected to the voltage source 300 via a sensing electrode 320 (SE) and a contact electrode 360 (CE), respectively. The voltage source 300 can be in the form of an integrated, external crystal measurement system (not shown) that includes a power supply and an oscillator that drives the piezoelectric substrate 110 having the ionic liquid 170 above the top surface 112. The crystal measurement system further includes a frequency counter and a voltmeter connected to the oscillator to display the results derived from the output signal of the piezoelectric substrate 110. The disk electrode 120, the ring electrode 130, and the ring electrode 140 are used for electrochemical measurements and are electrically connected to potentiostat 200 via a reference electrode 220 (RE), a working electrode 230 (WE), and a counter electrode 240 (CE), respectively. A voltage is applied across the electrodes 120 and 130 (i.e., reference and working electrodes) depending on the particular type of electrochemical measurement (e.g., cyclic voltammetry (CV), differential pulse voltammetry (DPV), square wave voltammetry (SWV), or others). The current resulting from the applied voltage is measured across the electrodes 130 and 140 (i.e., working and counter electrodes) and recorded as the voltammogram of the sensor 100.

Figure 33B:
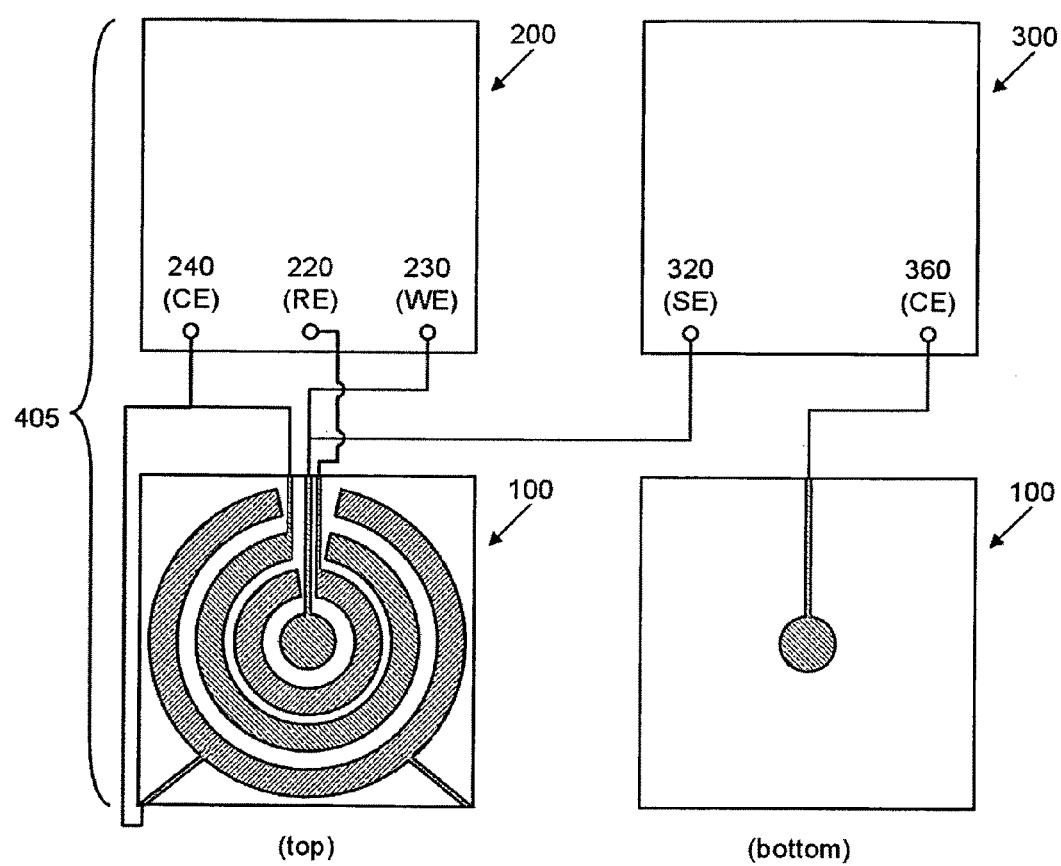

In another embodiment, the sensor 100 can be incorporated into an electrochemical piezoelectric sensing system 405, for example a system for electrochemical impedance spectroscopy as illustrated in FIG. 33B. In an embodiment, the sensor 100 includes a conductive polymer to immobilize ionic liquid(s) when used for impedance spectroscopy. The sensing system 405 includes the sensor 100 electrically connected to a electrochemical impedance analyzer such as PAR 2263 potentiostat or Solotron impedance analyzer 200 (or other means for supplying a variable frequency alternating current/voltage and measuring the resulting impedance) and an AC voltage source 300. Similar to the system 400, a single sensor 100 or a plurality of sensors as an array (not shown) can be included in the sensing system 405. The electrical connections to the voltage source 300 are the same as in the system 400. The disk electrode 120, the ring electrodes 130, 140, 150 are used for electrochemical impedance spectroscopy. The disk electrode 120 and the ring electrode 130 are electrically connected to the potentiostat 200 via a working electrode 230 (WE) and a quasi-reference electrode 220 (RE), respectively. The ring electrodes 140, 150 are electrically connected to the potentiostat 200 via a counter electrode 240 (CE). A variable frequency alternating current/voltage is applied across the electrodes 120 and 130 (i.e., working and reference electrodes), and the resulting impedance of the system 405 is recorded as the impedance spectroscopy of the sensor 100. The electrodes for electrochemical impedance measurements are typically connected the same way as for voltammetry (e.g., using the working electrode, the reference, and the counter electrode). In certain cases, two electrode systems are also used in electrochemical impedance measurement in which there is no counter electrode.

In yet another embodiment, the sensor 100 can be electrically integrated into a sensing system incorporating any combination of the elements from the systems 400 and 405. For example, the sensor 100 can be integrated into a system adapted to perform voltammetric measurements, impedance spectroscopy measurements, and (optionally) piezoelectric measurements.

The electrode patterns on the substrate 110 can be formed by any suitable means known in the art. For example, the electrodes can be formed by depositing a conducting metal (e.g., gold, silver, copper. platinum) above the top and bottom surfaces 112, 114 of the substrate 110 by methods such as chemical vapor deposition. Preferably, an intermediate adhesion layer (e.g., titanium) is first deposited (e.g., also by chemical vapor deposition) on the top and bottom surfaces 112, 114 of the substrate 110, and the conducting metal is then deposited on the adhesion layer. Photolithographic and etching steps are then used to pattern the electrodes as illustrated in FIGS. 32A, 32B, and 32C. In the figures, the disk electrode 120 includes an adhesion layer 122 and a conducting layer 124 resulting from the deposition and etching steps. Similar resulting layers are also illustrated for the other electrodes.

Figure 34A:
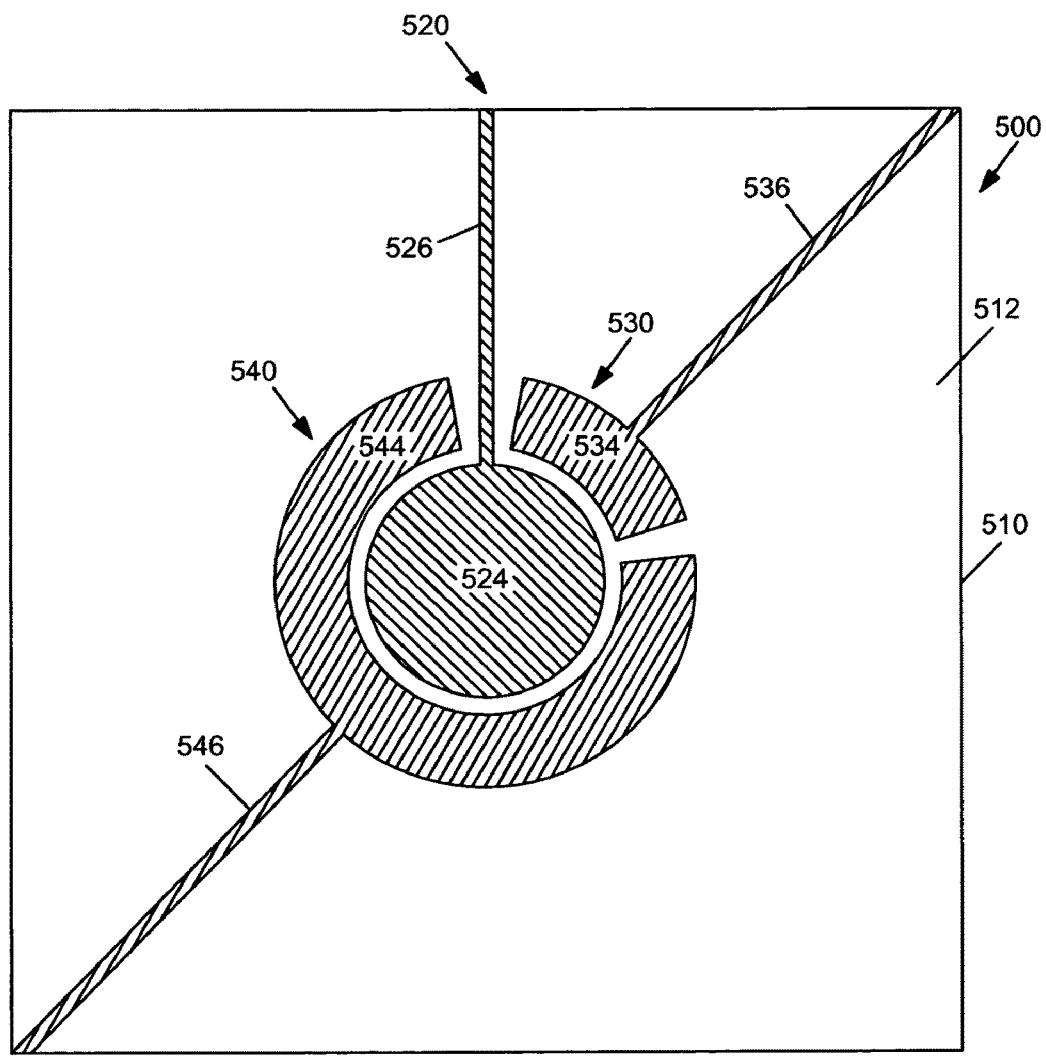
FIG. 34. Top (A) and bottom (B) view of an electrochemical piezoelectric gas sensor according to the disclosure.
Figure 34B:
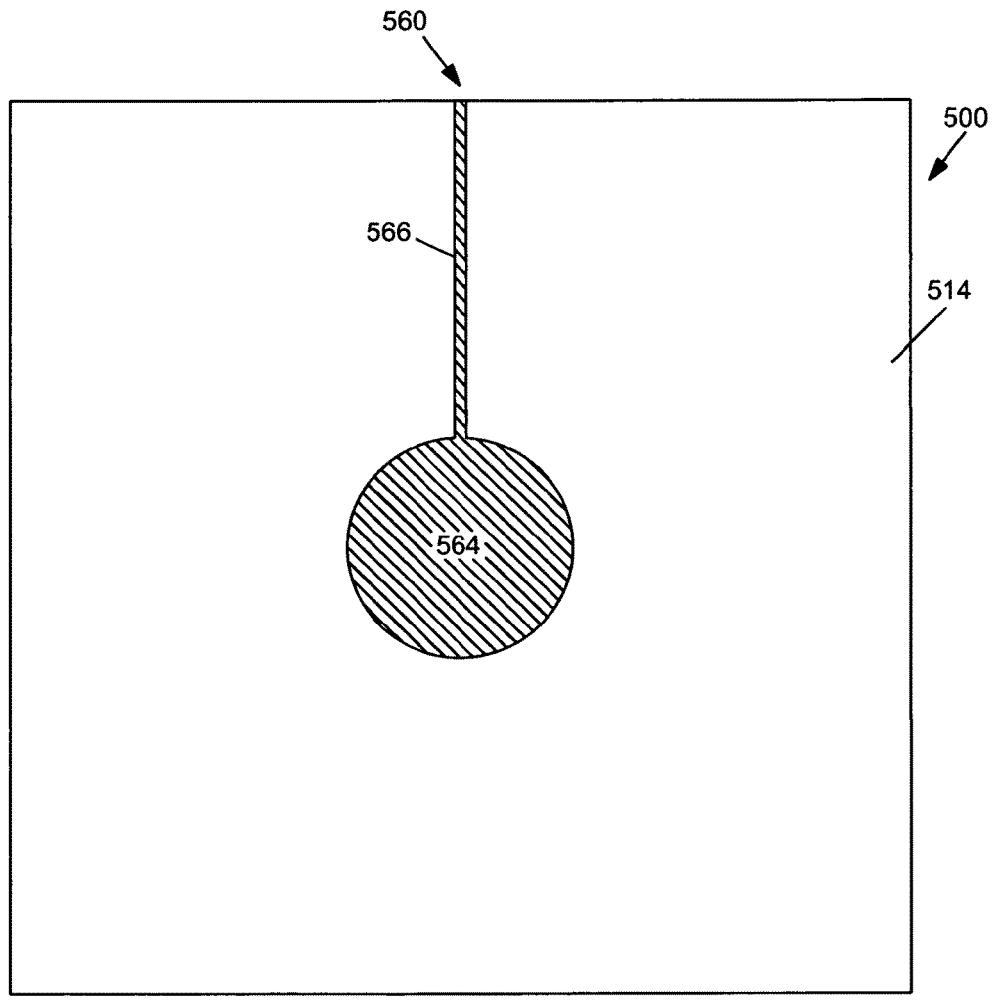
Figure 35A:
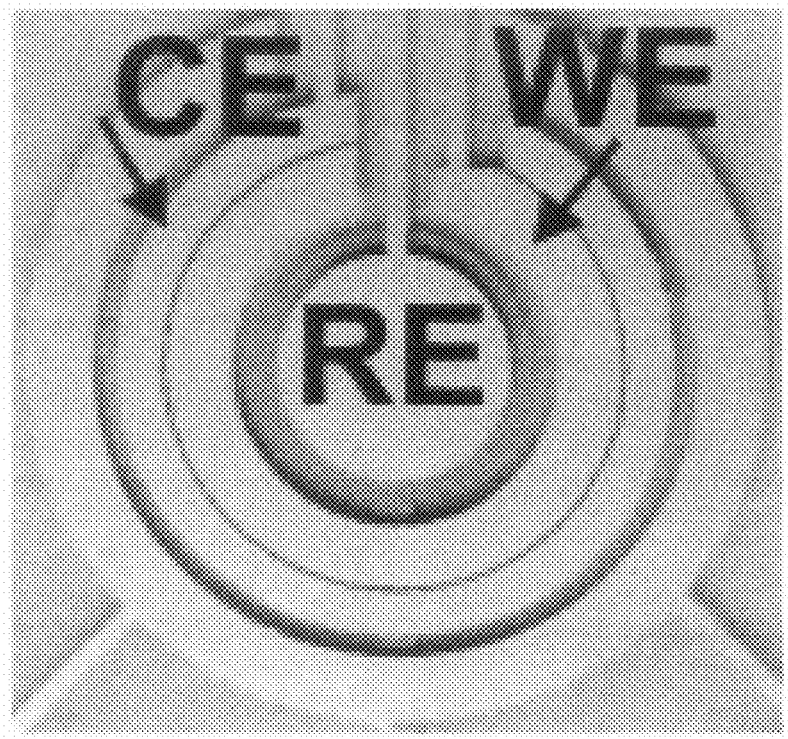
FIG. 35. Electrode patterns on an RsDE device (A; top view); an EQCM electrode (B; top and bottom view); and an alternate embodiment of an EQCM electrode (C (top view) and D (bottom view)).
Figure 35B:
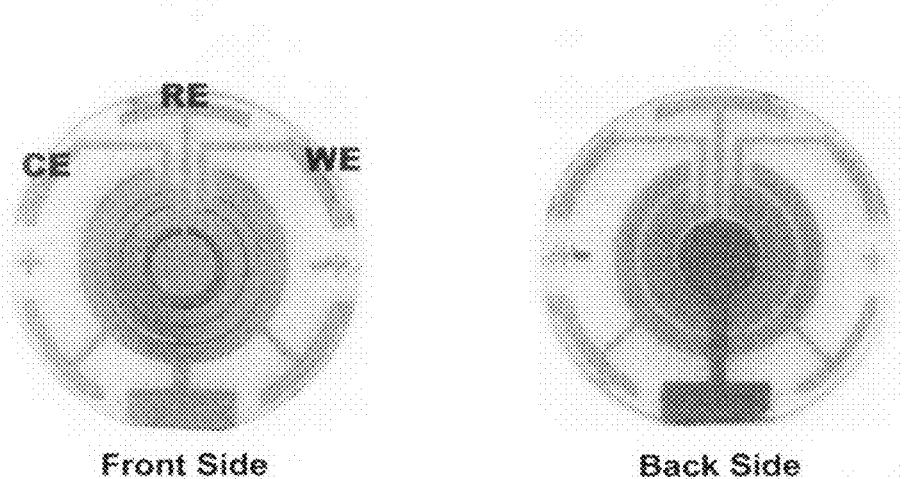
Figure 35C:
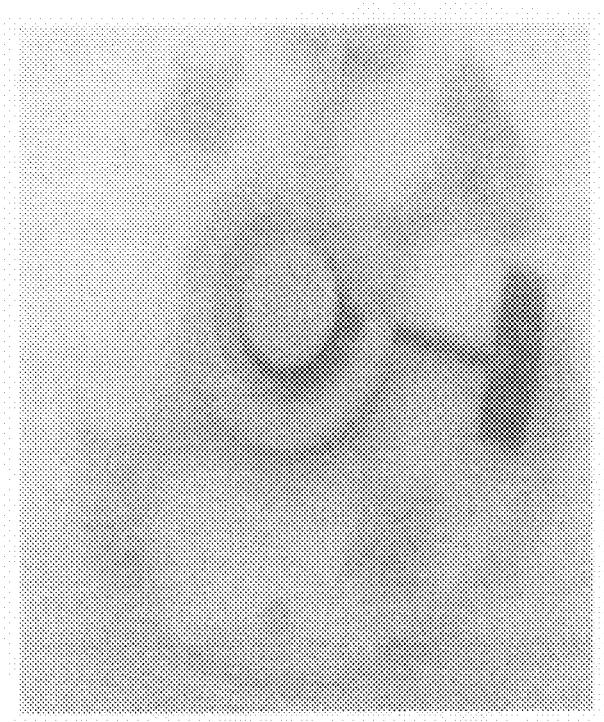
Figure 35D:
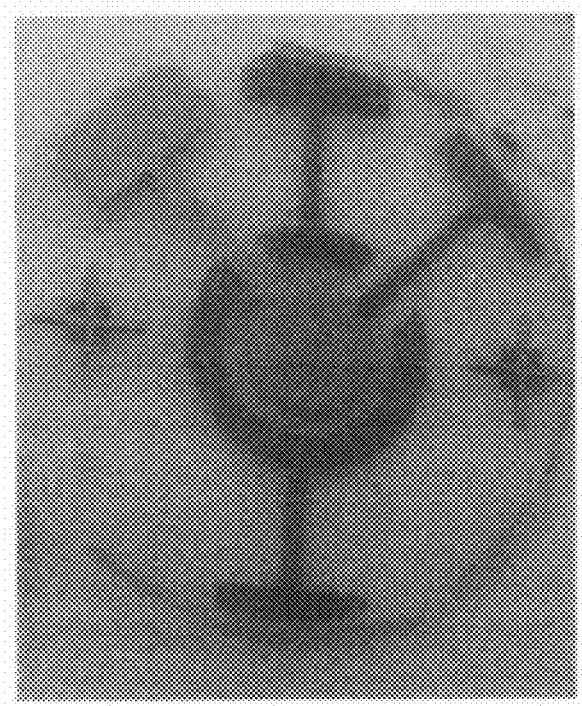

An additional embodiment of an electrochemical piezoelectric sensor 500 according to the disclosure is illustrated in FIGS. 34A and 34B (top and bottom schematics) and in FIGS. 35C and 35D (top and bottom photos of electrodes fabricated on a quartz substrate). The sensor 500 has a different electrode pattern, but otherwise has similar features as the sensor 100 (e.g., fabrication materials, fabrication methods, inclusion of one or more ionic liquid films on the top and bottom sensor surfaces). The sensor 500 includes a substrate 510 having a top surface 512 and a bottom surface 514. A top disk electrode 520 on the top surface 512 of the substrate 510 opposes a bottom disk electrode 560 on the bottom surface 514 of the substrate 510. Preferably, the disk electrodes 520, 560 are substantially aligned, for example along a line generally perpendicular to the substrate 510. The top surface 512 of the substrate 510 further includes a first arc electrode 530 and a second arc electrode 540 at outward radial positions away from the disk electrode 520 and spaced away from each other. As illustrated, the arc electrodes 530, 540 are located at substantially the same radial positions and represent arcuate sections of an annular region surrounding the top disk electrode 520. Generally, the first arc electrode 530 includes a portion that encompasses a minority of the circumference of the top disk electrode 520 (e.g., about 40% or less, about 5% to about 40%, or about 10% to about 30% or the circumference). The second arc electrode 540 includes a portion that encompasses a substantial portion (e.g., a majority) of the circumference of the top disk electrode 520 (e.g., about 30% or more, about 40% to about 90%, about 50% to about 90%, or about 60% to about 80% of the circumference). In the specific embodiment illustrated, the disk electrodes 520, 560 include substantially disk-shaped portions 524, 564 and wiring/lead portions 526, 566 (e.g., for electrical connections to external power supplies/measuring devices). Similarly, the arc electrodes 530, 540 include substantially arc-shaped portions 534, 544 and wiring/lead portions 536, 546 (e.g., also for external electrical connections).

The sensor 500 can be incorporated into an electrochemical piezoelectric sensing system (e.g., any of the above sensing systems, for example the system 400 and/or the system 405) in a manner analogous to the sensor 100. For example, when used for electrochemical measurements, the top disk electrode 520 can serve as a working electrode (WE), the first arc electrode 530 can serve as a quasi-reference electrode (RE), and the second arc electrode 540 can serve as a counter electrode (CE). The counter and working electrodes preferably are spaced apart but close together so that the IR drop can be reduced. The CE-WE spacing can suitably range as does the first distance $D_1$ described above for the sensor 100. The quasi-reference electrode and the counter electrode preferably are spaced farther apart to prevent the product in counter electrode from diffusing to the reference electrode, which diffusion can in turn adversely affect the reference electrode stability. The CE-RE spacing can suitably range as does the second distance $D_2$ described above for the sensor 100. When used for QCM measurements, the disk electrodes 520, 560 can serve as a sensing electrode (SE; top) and a contact electrode (CE; bottom), respectively.

In another embodiment, a sensor cell (e.g., in a multisensor array) contains a set of electrodes within a reservoir (e.g., 1 mm diameter and 500 μm deep) containing an ionic liquid interface. Each set of electrodes contains a Quasi Reference Electrode (QRE), a ring CE, and alternating concentric ring working electrodes (WE1 and WE2) with nanoscale dimensions. Electrodes can be deposited using physical vapor deposition and photolithography or e-beam lithography for the nano-scale electrodes. Various conductive electrode metals (e.g., Au, Ag, Pt) can be used, and different metals can be placed within each cell or varied across the array.

Concentric rings-disk electrode (RsDE) devices were prepared by vapor deposition of 5-nm of Ti followed by 100-nm of Au on glass slides. Then photolithography and wet etching were applied to pattern the electrodes as shown in FIG. 35A (and corresponding to the general structure illustrated in FIGS. 32A, 32B, and 32C). The disk electrode in the center has a diameter of 2.54 mm. The disk electrode is surrounded by three concentric ring electrodes, each with an opening on the same side for wiring. The first, second, and third ring electrodes have annular widths of 0.7 mm, 0.5 mm, and 0.75 mm, respectively. The annular gaps between the disk electrode and the first ring electrode, the first and the second ring electrodes, and the second and the third electrodes are about 500 µm, 50 µm, and 250 µm, respectively. The disk electrode was used as pseudo reference electrode. The first and the second rings were used as working and counter electrodes, respectively. This choice of electrodes allows the working electrode and counter electrode to be close together so that the IR drop (voltage drop) can be reduced. Additionally, the quasi reference electrode and the counter electrode are placed far apart to prevent the product at the counter electrode from diffusing to the reference electrode and affecting reference electrode stability.

The EQCM electrode device shown in FIG. 35B was prepared using the same methods as the RsDE device shown in FIG. 35A, with the RsDE pattern on one side of a quartz plate. The quartz plate had thickness of about 165 µm and a corresponding fundamental oscillation frequency of about 10 MHz. The other side of the quartz plate was coated with a gold disk electrode. The two disk electrodes overlapped concentrically. The gold and non-polished quartz plate substrates are very wettable by the ionic liquid $BMIBF_4$. When the RsDE was used, 4 µL of $BMIBF_4$ (or its solutions containing a nitroaromatic analyte) were pipetted on the center of the top disk electrode and allowed to cover the whole area of the rings-disk electrode. Then this tiny drop of ionic liquid was spread carefully with the very end of the plastic tip. Finally, the ionic liquid covered all the area of the electrodes and between the electrodes. A very small fraction of the ionic liquid may spread out of the concentric electrodes area due to the handling. The surface tension of the ionic liquid makes the thin layer "uniform" and holds the $BMIBF_4$ solutions within the desired area without further dispersion. The final $BMIBF_4$ electrolyte thin layer had an average thickness of about 150 µm, although the thicknesses at the center and the outer edge of the ionic liquid film are likely not identical. For subsequent measurements, the RsDEs were either exposed in the air or in a sealed chamber. The chamber was initially filled by air, and then a drop of ENB or a tiny amount of DNT was introduced into the chamber using a syringe. Given enough time, the air in the chamber would become saturated with ENB or DNT vapors.

Solutions with different concentrations of nitro compounds were prepared by directly dissolving the nitro compounds in $BmiBF_4$ ionic liquid and then diluting them with $BMIBF_4$. While redox behaviors of the nitro-group aromatic compounds were studied in $BmiBF_4$ bulk solutions, a quasi-reference electrode (Au or Ag) was used to avoid the contamination of the IL electrolyte by the reference electrode filling solution. To reduce reference electrode drift problems associated with a quasi-reference electrode, most of the voltammograms were further calibrated to $O_2/O_2^-$ or $Fc/Fc^+$ redox potential. When the analyte sample concentrations were below 10 mM, their redox peak currents were comparable to that of oxygen reduction; therefore, the $O_2/O_2^-$ peak was used as reference. When the analyte sample concentrations were relatively high, the $O_2/O_2^-$ peak was very small compared with the peaks of analytes. Hence, ferrocene was added into the IL electrolyte to calibrate the electrode potential.

Electrochemical and QCM measurements: In the following measurements, the electrode device (e.g., EQCM, QCM, RsDE) was set up in a gas flow detection system illustrated in Jin et al., "Enhancing the sensitivity of ionic liquid sensors for methane detection with polyaniline template," *Sensors and Actuators B: Chemical, Volume* 133, Issue 2, 12 Aug. 2008, Pages 526-532 (incorporated herein by reference; "Jin et al.") [30]. Pure nitrogen gas was used as a carrier gas. A nitrogen flow of 200 mL/min was bubbled through a nitroaromatic reservoir (e.g., ENB, 2,4-DNT, 2,6-DNT, 3,4-DNT) to generate saturated nitroaromatic vapor. The nitroaromatic-saturated $N_2$ was further diluted by nitrogen gas and the final concentration was calculated based on the ideal gas law. The overall flow rate was 200 mL/min. Each side of the QCM was covered by 4 nmol $BMIBF_4$. For QCM measurements, the two disk electrodes on the front and back sides of the electrode device were connected to a MAXTEK RQCM instrument (Inficon, Inc.; East Syracuse, N.Y.), which measured the frequency change in real-time. Electrochemical measurements were performed with an EG&G 273 potentiostat (Princeton Applied Research; Oak Ridge, Tenn.). The scan rate of for Cyclic Voltammetry (CV) was 100 mV/s with a period ranging from 1.0 V to −3.0 V (vs. $Fc/Fc^+$), unless otherwise mentioned. Square Wave Voltammetry (SWV) was performed with a pulse height of 50 mV, a frequency of 15 Hz, a step increment of 4 mV, and a scan rate of 60 mV/s. Differential Pulse Voltammetry (DPV) was performed with a pulse height of 25 mV, a scan rate of 20 mV/s, and a pulse width of 50 ms.

EXAMPLE 5

Bulk IL Solution Measurement (Reversibility)

Cyclic Voltammetry, Differential Pulse and Square Wave Voltammetry were used in parallel to characterize the electrochemical behavior of ENB and DNTs in bulk $BmiBF_4$ solutions without removal of trace amounts of dissolved $O_2$ and $H_2O$. CV is especially powerful in the study of electrode reaction mechanisms. DPV and SWV are among the most sensitive methods for the direct evaluation of the concentrations in trace analysis.

Figure 36:
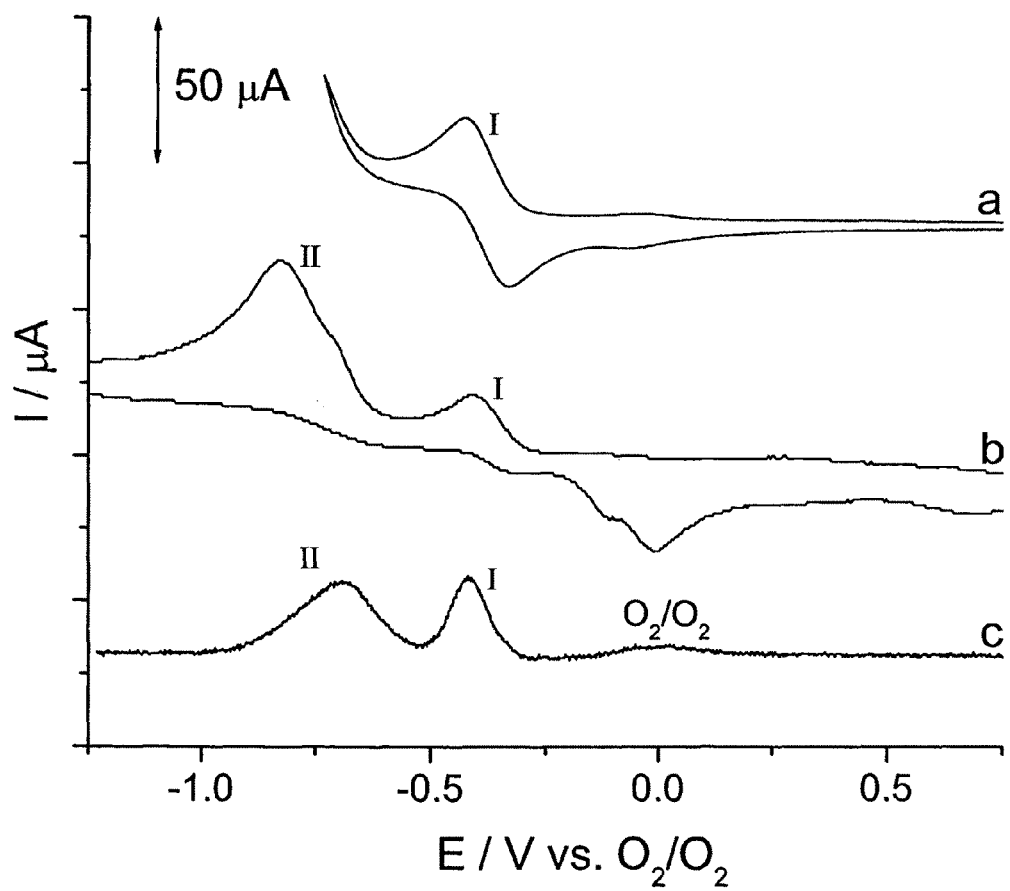
FIG. 36. CV of 1 mM ENB solution in $BMIBF_4$ from 0 to −1.5 V (a), CV of 1 mM ENB solution in $BMIBF_4$ from 0 to −2.0 V (b), and DPV of 1 mM ENB solution in $BMIBF_4$ (c). The reduction of oxygen was used as an internal reference because the oxygen concentration is always saturated in the $BMIBF_4$ electrolyte. The x-axis voltage is recalibrated assuming the $O_2$ peak to be at 0 V; the voltage range is −0.5 V to 2.5 V when the gold electrode is used as a reference electrode. The working, counter, and quasi-reference electrodes were gold disk, platinum wire, and silver wire, respectively.

FIG. 36 shows the CVs and DPV of 1 mM ENB in $BMIBF_4$ on a gold electrode. Typically, a reversible reduction and a subsequent irreversible reduction were observed in the potential range of 0.75 V~−1.25 V vs. the redox potential of oxygen. The first reduction peak corresponds to the reduction of the nitro (—$NO_2$) group to a nitro anion radical (—$NO_2^-$) [23-25]. In most electrolyte solutions this reduction is electrochemically and chemically reversible. The redox peak currents increased as scan rate increased. The peak currents are proportional to the square root of scan rates indicating a diffusion-controlled mechanism of the redox reaction. The second reduction of ENB, mostly irreversible, is related to the protons in the electrolyte solutions. In this step, the nitro radical anion is further reduced to nitro dianion (—$NO_2^{-}$) and eventually hydroxylamine ($NH_2OH$). Therefore, the existence of proton-donor compounds such as water will affect the second reduction of nitro compounds.

Figure 37:
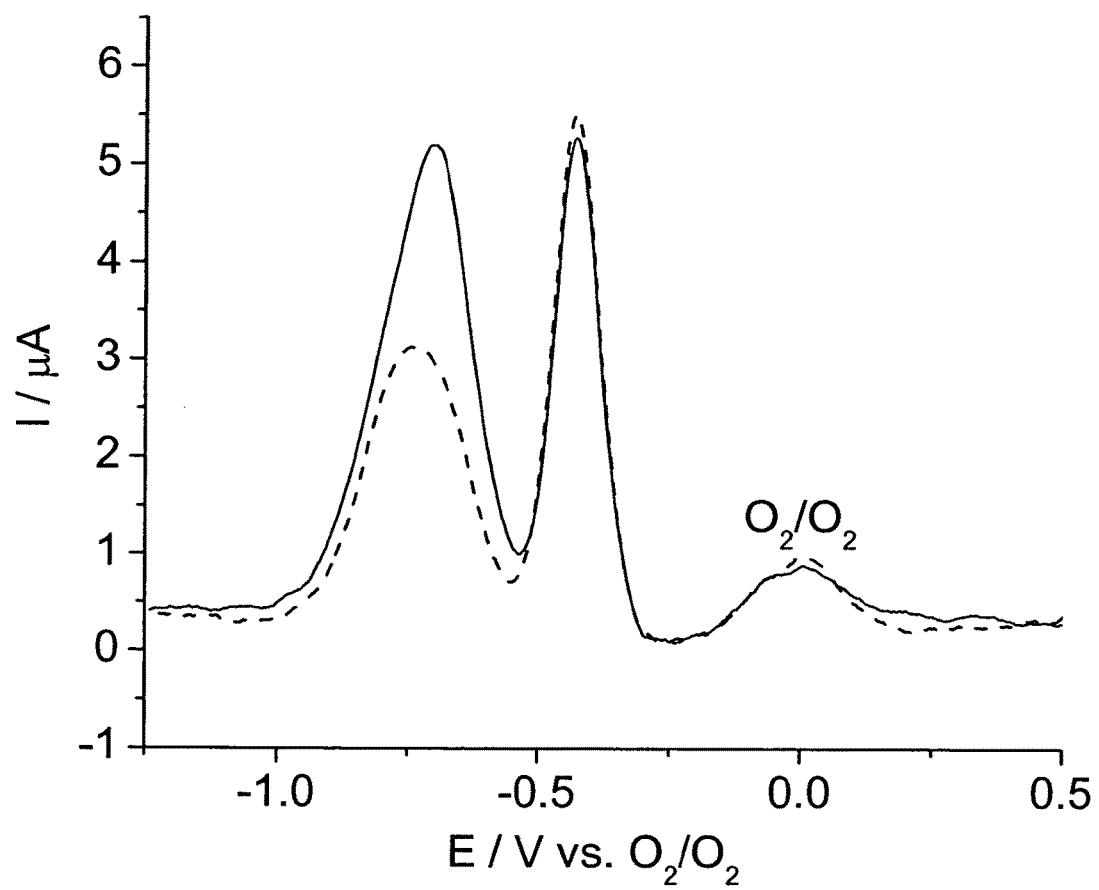
FIG. 37. SWVs of ENB in pure $BMIBF_4$ (solid line) and $BMIBF_4$ containing 0.01 vol. % water (dashed line).

As shown in FIG. 37, after the addition of a small amount of water (0.01 vol. %), the peak current of the second reduction in an SWV curve was reduced, while the peak current of the first reduction did not change significantly. Also shown in FIG. 37 is the fact that the peak positions did not depend on water contamination in the electrolyte. Hence, the first reduction of ENB that is reversible and stable is excellent for ENB amperometric analysis, as demonstrated in these examples.

Figure 38:
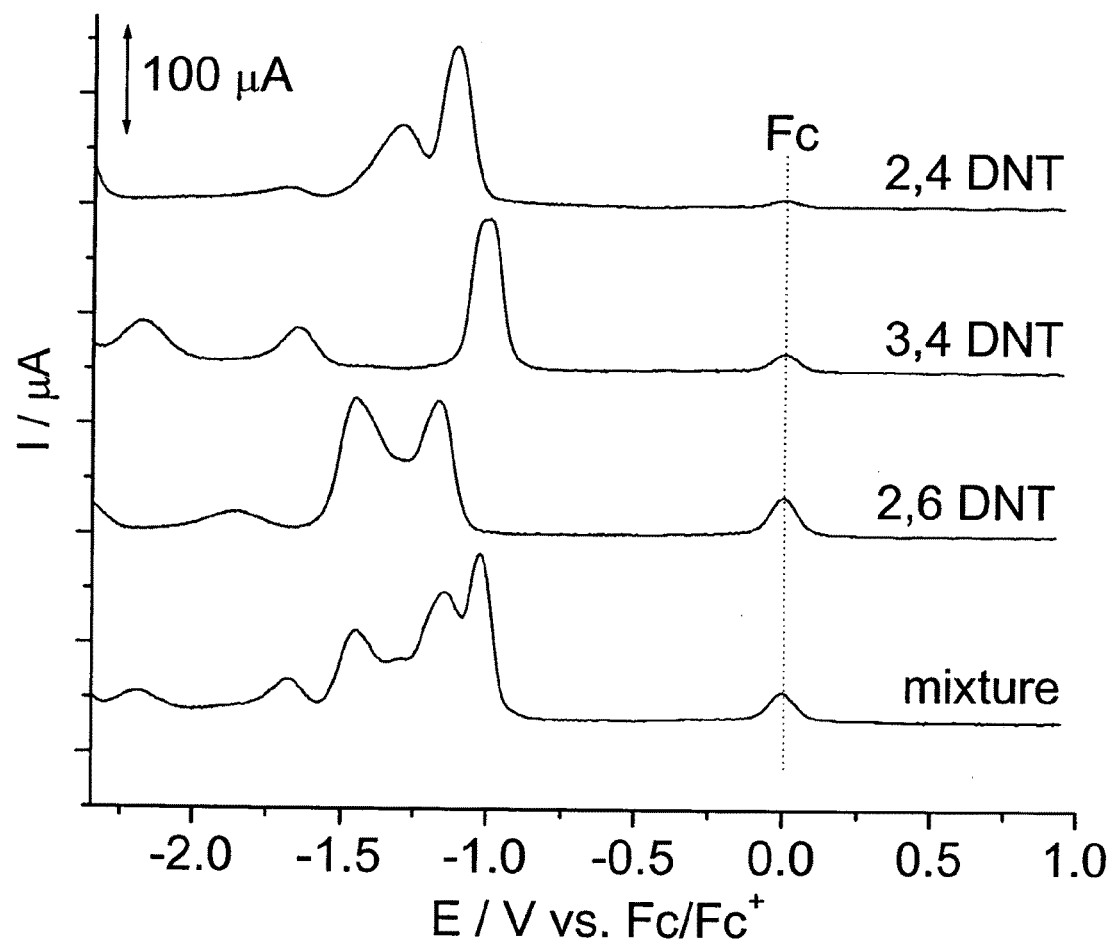
FIG. 38. SWVs of 0.1 M various DNT isomers in $BmiBF_4$.

FIG. 38 shows the SWVs of three typical DNT isomers (2,4-DNT, 2,6-DNT, and 3,4-DNT) and mixture of the three DNTs. All three DNTs showed more than two reduction peaks in the investigated potential range. The reduction peak positions were all different depending on the sites of the nitro groups on the benzene ring, as summarized in Table 4 and based on the data of FIG. 38. However, for all three DNTs, the first reduction peaks were reversible. Similar DPV/SWV data for ENB (not shown) are also included in Table 4.

TABLE 4

Reduction Peak Positions in SWVs of DNTs and ENB

| Compound: | 2,4-DNT | 2,6-DNT | 3,4-DNT | ENB |
|---|---|---|---|---|
| Peak Potentials (V vs. Fc/Fc$^+$) | −1.15 | −1.23 | −1.05 | −1.14 |
| | −1.35 | −1.37 | −1.70 | −1.41 |
| | −1.75 | −1.53 | −2.24 | |
| | −2.05 | −1.93 | | |

FIG. 39 shows that CV of ENB at different scan rates. The first two pairs of reduction peaks of ENB were proportional to the square root of the scan rate. Therefore, the reductions of ENB were diffusion-controlled processes. When two sites of benzene are substituted by nitro groups, the reduction reactions are more complicated.

EXAMPLE 6

Bulk IL Solution Measurement (IL Regeneration)

Figure 40:
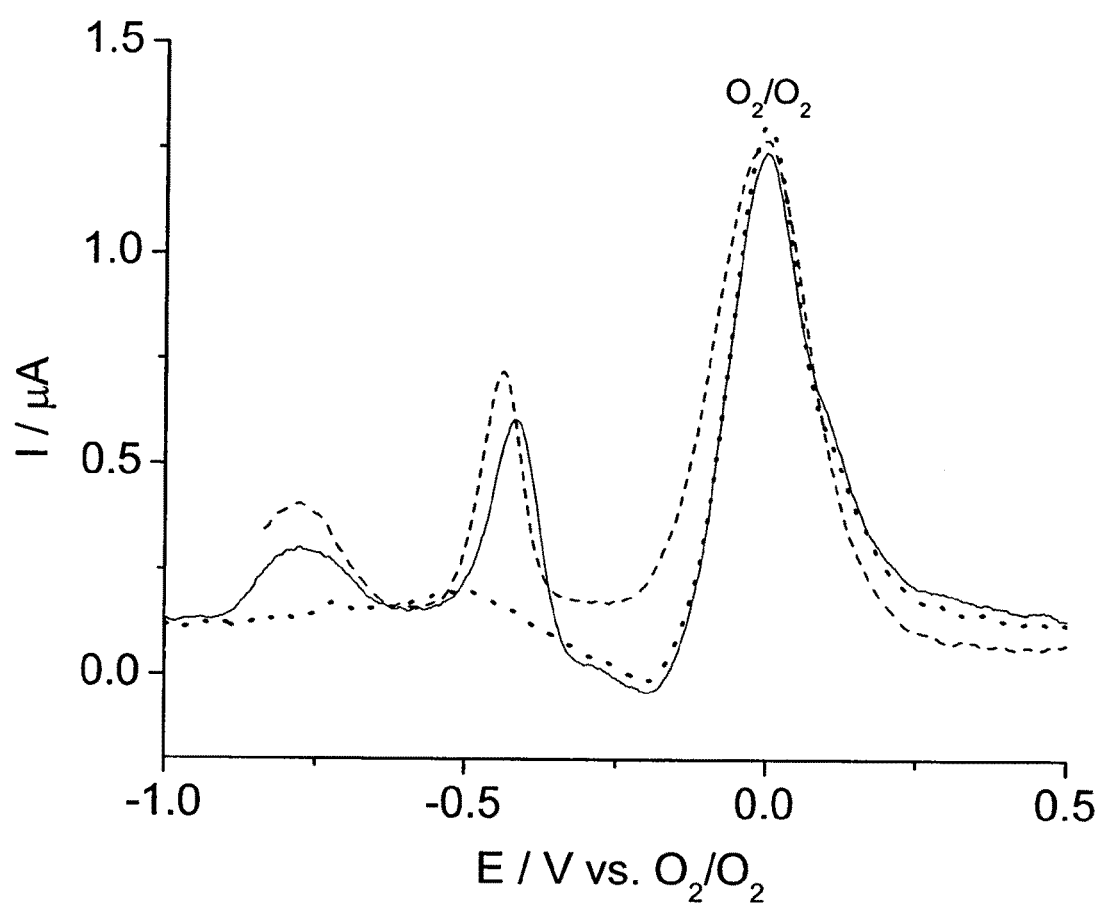
FIG. 40. DPVs of 11 ppm ENB in $BMIBF_4$ (dashed line), $BMIBF_4$ solution after removal of ENB by heating (dotted line), and $BMIBF_4$ solution with 11 ppm ENB added postheating (solid line).

In addition to the chemical and electrochemical reversibility, the redox reactions were also found to be reversible when the ENB was absorbed and removed from the electrolyte. Since BmiBF$_4$ is very stable at temperatures as high as about 300° C. and ENB is evaporable at a substantially lower temperature, an ENB solution in BmiBF$_4$ was heated by an infrared lamp to about 150° C. to remove the ENB. Afterwards, the peaks of ENB disappeared from the DPV of the remaining BIMBF$_4$. ENB was then added into the same BMIBF$_4$ electrolyte at the same concentration as before heating, and a DPV similar to that of the ENB-BIMBF$_4$ solution prior to heating was observed. These DPVs are shown in FIG. 40. In these curves, the peak position and the peak current of dissolved oxygen did not change, indicating that BmiBF$_4$ is a very stable electrolyte across the studied temperature. When ENB was added at the same concentration after heating, its peaks were observed at close to the same positions, but the peak currents were reduced slightly, which may be due to a baseline change. These results indicate that, when BmiBF$_4$ is used as an electrolyte for amperometric analysis of volatile chemicals, the electrolyte could be regenerated by simply heating to remove the analytes. Therefore, ionic liquids such as BmiBF$_4$ could be used for long-term monitoring and detection of nitro compounds.

EXAMPLE 7

Bulk IL Solution Measurement (Sensitivity)

Figure 41A:
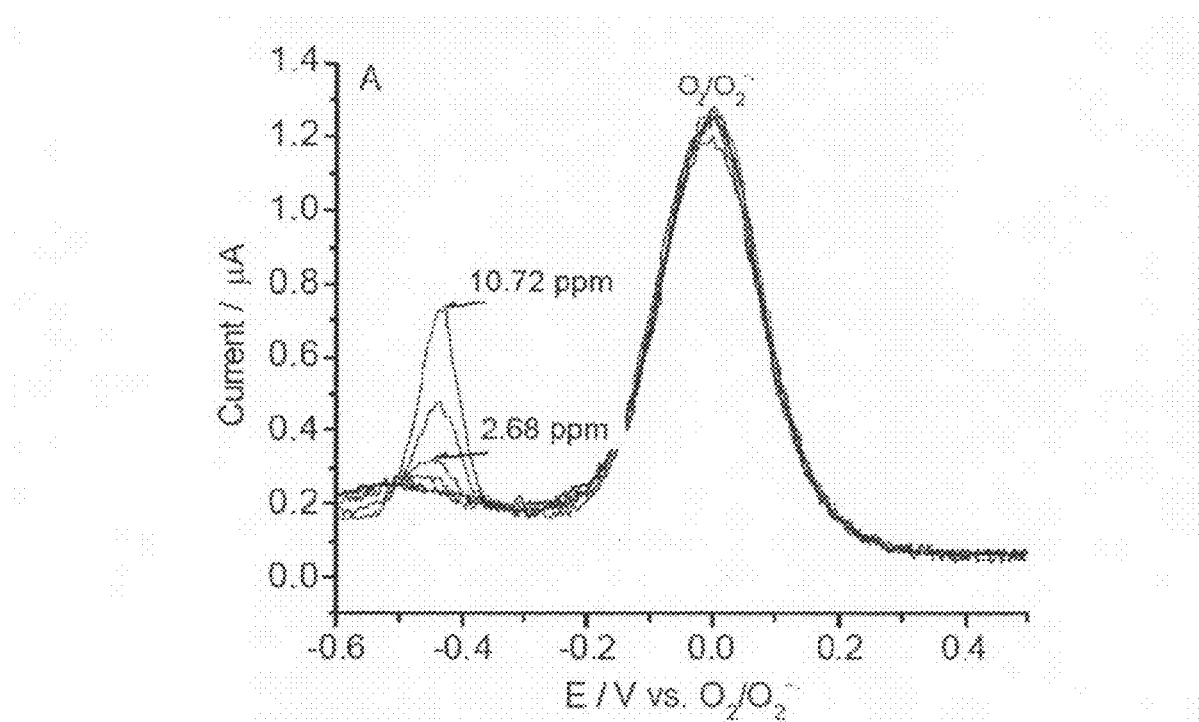
FIG. 41. DPVs of ENB in $BMIBF_4$ at concentrations up to about 10 ppm (A), and resulting peak DPV current vs. concentration (B).
Figure 41B:
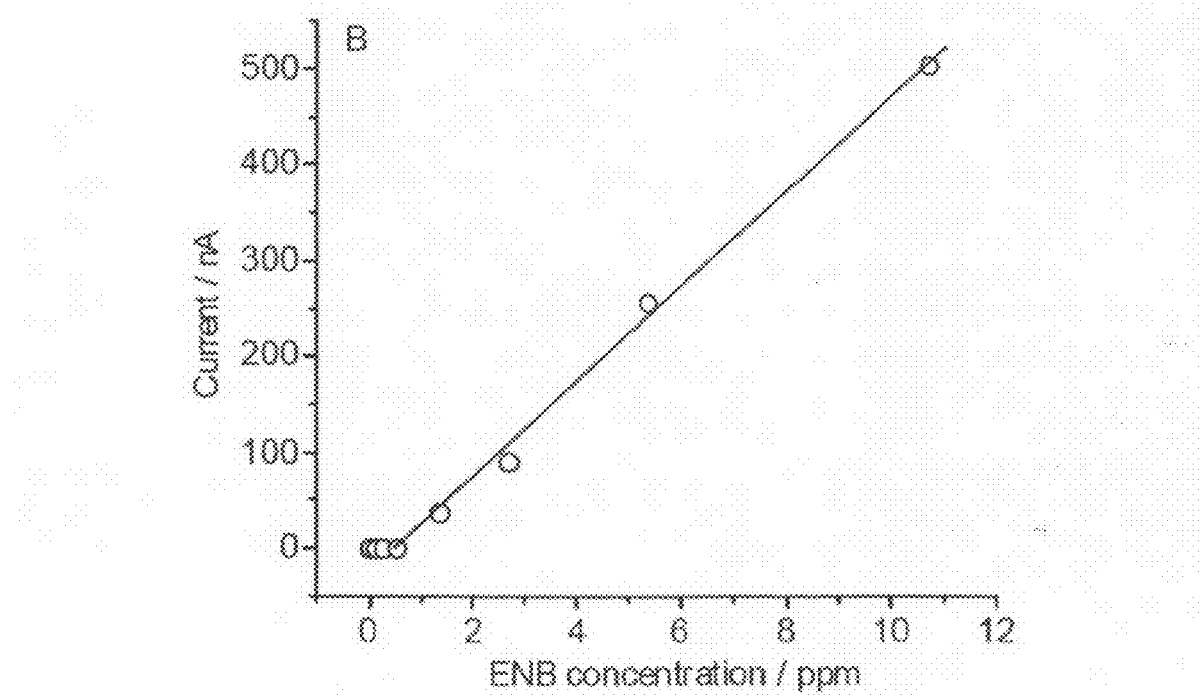

A sensitivity analysis was conducted using ENB-BMIBF$_4$ solutions with ENB concentrations ranging up to about 10 ppm. FIG. 41A shows the DPVs of ENB in BMIBF$_4$ at varying concentrations; the amplitude of the peak at about −0.45 V can be correlated to the ENB concentration. Down to 1.34 ppm, a very clear reduction peak of ENB at about −0.45 V (vs. O$_2$/O$_2^-$) could be distinguished. The experimental results in FIG. 41B show that the peak current has a highly linear relationship to the ENB concentration, with concentrations as low as about 1 ppm being distinguishable from the background DPV signal.

EXAMPLE 8

Thin-Film IL/RsDE Measurement

The excellent electrochemistry results in bulk BmiBF$_4$ solutions show that BMIBF$_4$ is a good electrolyte material for amperometric analysis of nitro compounds. However, if a bulk BMIBF$_4$ ionic liquid or solution were used to uptake or absorb nitro compound vapors in the atmosphere, the detection process would be slow. Since ionic liquids typically have higher viscosity than common organic solvents, a longer time is needed for vapors partitioned in it to reach equilibrium. From the data in FIG. 39 (peak current vs. square root of scan rate), the diffusion coefficient of ENB in BMIBF$_4$ was calculated to be about $2.4 \times 10^{-7}$ cm$^2$/s. This value is significantly smaller than the reported diffusion coefficients of metal, metal complex, or organic compounds in aqueous or organic (such as acetonitrile) electrolyte solutions, which are usually range from about $10^{-5}$ cm$^2$/s to about $10^{-6}$ cm$^2$/s. This value indicates a very slow diffusion of the ENB in ionic liquids, which is consistent with the fact that BMIBF$_4$, being an ionic liquid, is much more viscous than water.

Figure 42A:
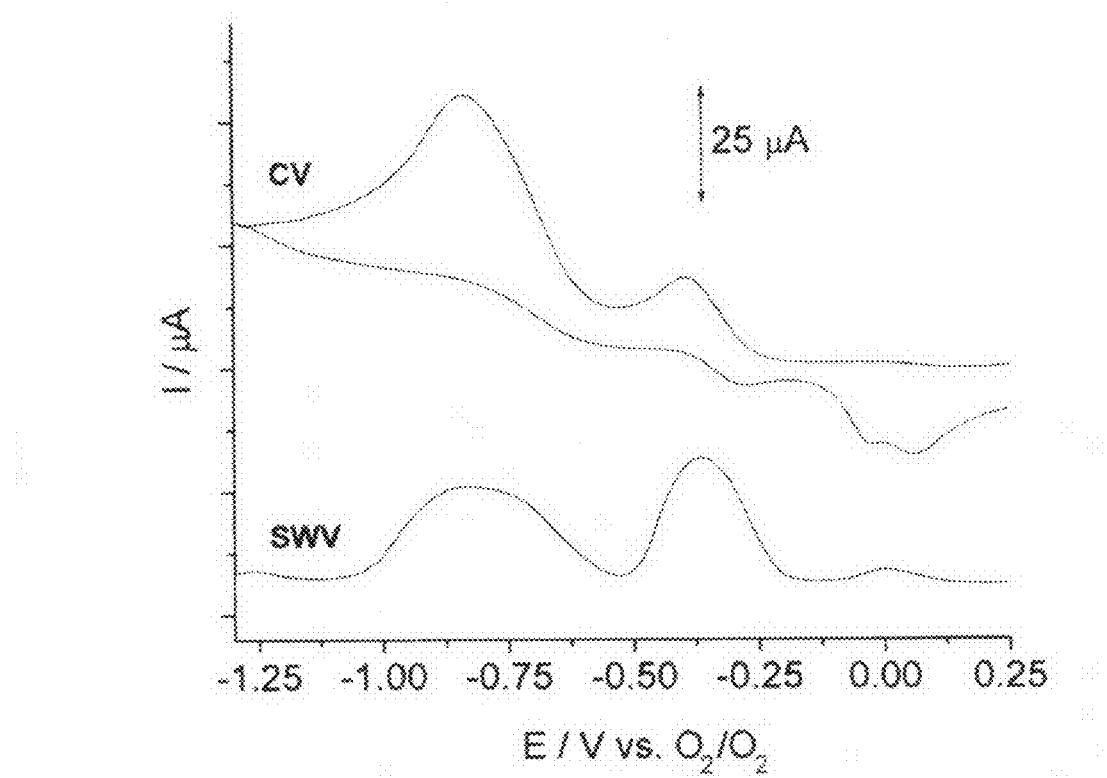
FIG. 42. CV (scan rate: 100 mV/s; top) and SWV (bottom) of 0.01 M ENB-$BMIBF_4$ solution on concentric gold rings-disk electrodes (A), and fabricated substrate with electrodes (B). The chip having two sets of electrodes in FIG. 42B are in close vicinity to allows redox recycling for analytes which have a reversible redox behavior, thus amplifying the amperometric current signals.
Figure 42B:
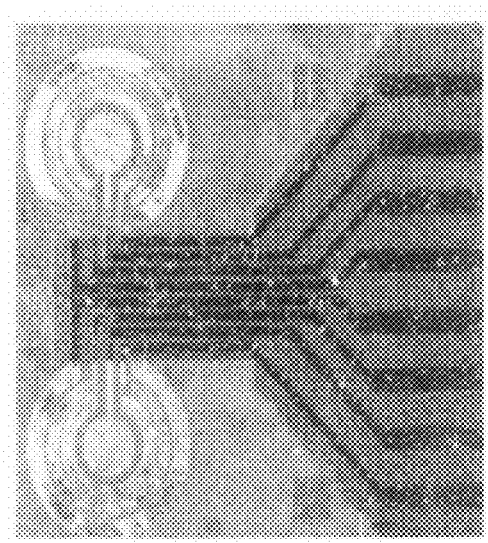

To overcome this limitation, it is desirable to realize a sensor using a thin film electrolyte, which would reduce the time required to achieve equilibrium. The planar, concentric multi-electrode, RsDE device described above (FIG. 35A) was utilized to develop an amperometric sensor featuring a thin film ionic liquid electrolyte. About 4 μL of solution (0.01 M ENB in BMIBF$_4$) was applied to cover all the area of the electrodes, about 0.28 cm$^2$. This yields a solution layer thickness of about 150 μm. As shown in FIG. 42, the CV (top curves) and SWV (bottom curve) results for ENB obtained with the thin film electrolyte resembled those obtained in bulk solutions (FIGS. 36A and 37, respectively). These results show the two reduction processes of ENB, the first reversible and the second irreversible peaks. The peak positions were almost identical to those observed in bulk solutions. The oxygen peak that can also be observed was used as a reference.

EXAMPLE 9

Thin-Film IL/RsDE Measurement (Sensitivity)

Figure 43:
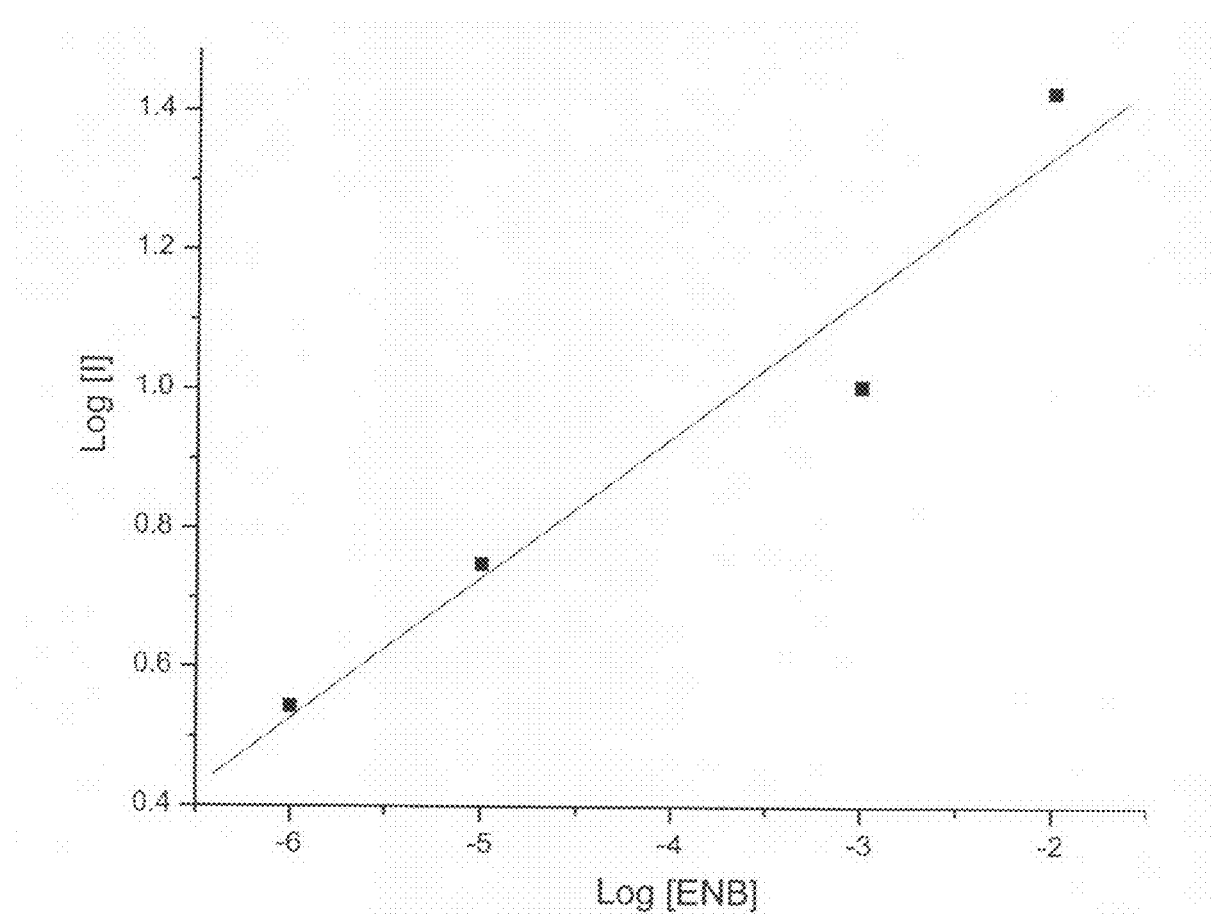
FIG. 43. Peak current of the first SWV reduction peak vs. ENB concentration in $BMIBF_4$. SWVs were obtained with thin film electrolyte on gold rings-disk electrodes.

BMIBF$_4$ solutions containing varying amounts of ENB (0.01 M, 0.001 M, 0.00001 M, and 0.000001 M) were applied to the RsDE device to evaluate the sensitivity and the concentration-current relationship for the thin-film IL. The peak current in the SWVs increased with increasing ENB concentrations, as shown in FIG. 43 (plotting log$_{10}$ of the current in μA and log$_{10}$ of the ENB concentration in molarity). However, with the thin-film electrolyte device, the peak current was not observed to be directly proportional to the ENB concentration. Instead, the logarithm of peak current was found to be approximately proportional to the logarithm of ENB concentration. A quantitative description of the diffusion processes and the boundary conditions of this system are not clear yet. Therefore, an empirical quantitative amperometric analysis was performed using calibration curves from the RsDE and thin-film ionic liquid electrolytes.

EXAMPLE 10

Thin-Film IL/RsDE Measurement (Gas Phase)

Figure 44:
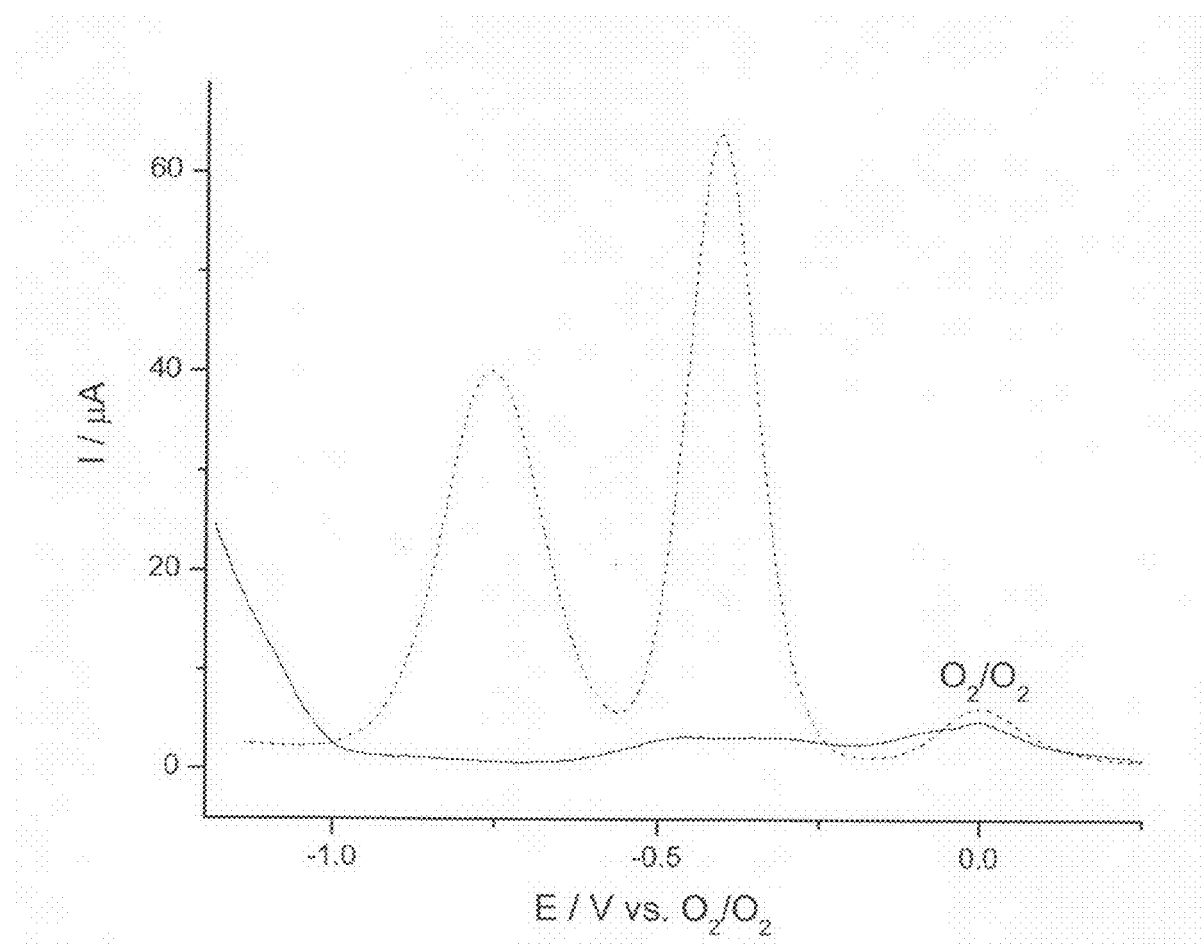
FIG. 44. SWVs of thin-film $BMIBF_4$ electrodes in air (solid line) and in ENB-saturated air (dotted line).

The ability of the thin-film RsDE device to detect nitroaromatic compounds in the gas phase was also tested. The RsDE device was coated with about 4 μL of $BMIBF_4$ (i.e., absent any added ENB or other nitroaromatics) as described above. The RsDE device was placed in a sealed chamber having an atmosphere of either (a) air or (b) ENB-saturated air. The RsDE device was allowed to equilibrate in the sealed chamber for two hours, and was then analyzed using SWV, the results of which are shown in FIG. 44. Relative to the ENB-free air background, the SWV of ENB shows a significant signal for ENB reduction, indicating the absorption of gas-phase ENB into the IL film and the subsequent detection of ENB therein.

EXAMPLE 11

Thin-Film IL/EQCM Measurement

The electrochemical and/or piezoelectric sensor (or sensor system) in any of its various embodiments (e.g., sensors 100 and/or 500, systems 400 and/or 405, for example as illustrated in FIGS. 32 and 33; described below with reference to the sensor 100 and the system 400 for convenience) can be used in a method of analyzing a gaseous sample for the presence (or absence) of one or more target analytes (e.g., gas-phase analytes). The sensor is exposed to a gaseous sample (e.g., in a confined sampling chamber or in the ambient environment) to absorb at least a portion of any target analytes (e.g., explosive vapor species in an explosive vapor as described in more detail below, environmental gases) present in the gaseous sample into the ionic liquid film (or films, for example when the sensor/system includes more than one ionic liquid film and/or a sensor array). The sensor can be contacted with the gaseous sample for a time sufficient for any target analytes in the sample to form an equilibrium partition (or substantial equilibrium partition, for example about 90% or more of an equilibrium concentration) between the gas and ionic liquid phases prior to taking any sensor measurements. Alternatively, sensor measurements can be taken in real time and/or without delay with respect to introduction of the gaseous sample to the sensor 100, irrespective of whether gas-liquid equilibrium has been achieved.

Piezoelectric measurements are made by applying a first voltage across the disk electrodes 120, 160 and then measuring a resulting change in a resonant frequency in the piezoelectric substrate 110 (e.g., with the potentiostat 200). The concentration of an identified analyte can be calculated based on/correlated with the resonant frequency change in the substrate 110. The thickness of the ionic liquid film 170 is generally large enough for viscosity-controlled piezoelectric behavior, resulting in a resonant frequency change that is positive (e.g., relative to some pre-measurement or pre-exposure baseline, for example established by analysis of an analyte-free reference gas either prior to, after, or in parallel with sample analysis with the same or different sensor). Thus, the concentration of an identified explosive vapor species generally is directly proportional (e.g., substantially linearly proportional) to the (positive) resonant frequency change. The second ionic liquid film 180, when present, can be either small enough for mass-controlled piezoelectric behavior (i.e., resulting in a resonant frequency change that is negative) or large enough for viscosity-controlled piezoelectric behavior.

Figure 39A:
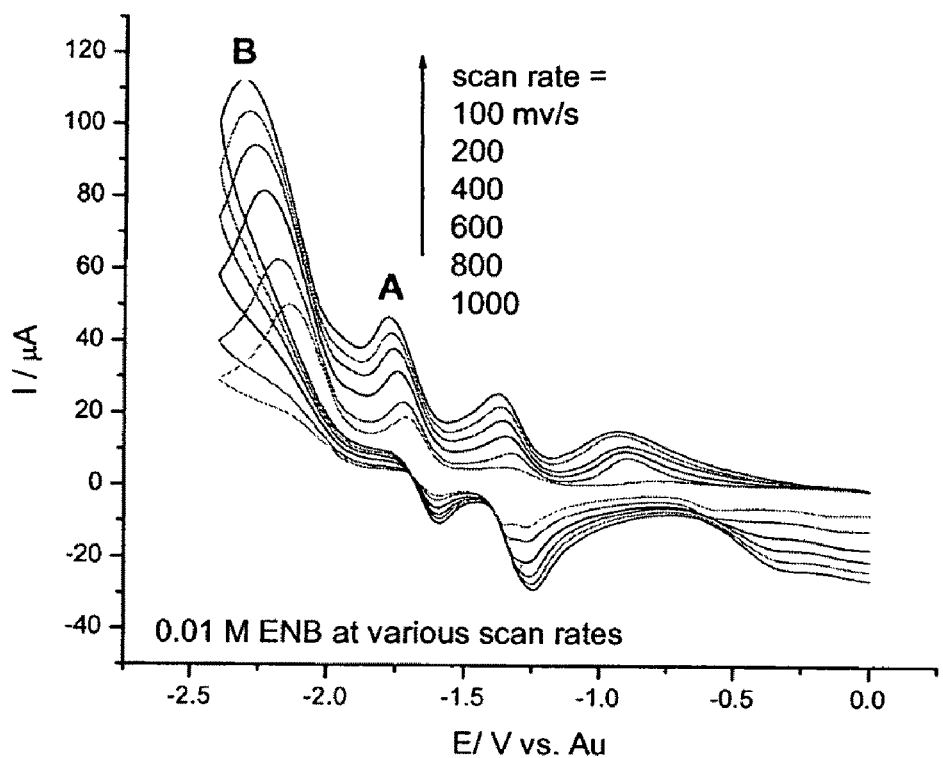
FIG. 39. CVs of 0.01 M ENB in $BmiBF_4$ at scan rates ranging from 100 mV/s to 1 V/s (potential referenced by pseudo reference electrode Au) (A); Peak current of the first pair of redox peaks as a function of the square root of the scan rate normalized by a reference scan rate of 1 V/s (B).
Figure 39B:
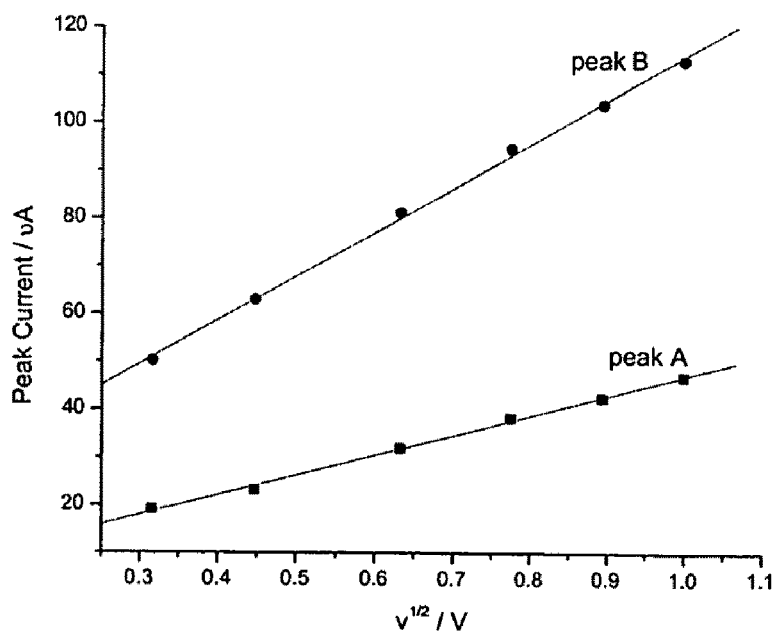

Voltammetric electrochemical measurements are made by applying a second voltage across the disk electrode 120 and the first ring electrode 130, and then measuring a resulting voltammetric current trace (e.g., a set of data points representing the measured current as a function of the variable applied second voltage) across the first ring electrode 130 and the second ring electrode 140. The applied second voltage can be varied in a time-dependent manner to perform any of a variety of voltammetric methodologies, including one or more of cyclic voltammetry (CV), square wave voltammetry (SWV), and differential pulse voltammetry (DPV) (e.g., the same sensor 100 can be used to sequentially/cyclically perform two or more voltammetric methodologies, including CV, SWV, and/or DPV). Similar to the piezoelectric measurements, the concentration of an identified analyte can be calculated based on/correlated with one or more characteristic peaks in the voltammetric current trace. The concentration of an identified explosive vapor species generally is directly proportional (e.g., substantially linearly proportional, substantially logarithmically proportional) to the amplitude of the characteristic peak/peaks (or, more generally, peak magnitude, for example peak area). Peak amplitude can be determined relative to an established baseline in the voltammetric current trace, or, similarly to the piezoelectric measurement, the peak amplitude can be determine relative to some pre-measurement or pre-exposure baseline (e.g., established by analysis of an analyte-free reference gas either prior to, after, or in parallel with sample analysis with the same or different sensor). This proportionality is shown in FIGS. 39A and 39B (CV traces illustrating a square-root proportionality for two characteristic peaks), FIGS. 41A and 41B (DPV traces illustrating a linear proportionality for one characteristic peak), and FIG. 43 (log-log proportionality for one characteristic peak in an SWV trace).

Impedance spectroscopy electrochemical measurements are made by applying a second voltage or current across the disk electrode 120 and the first ring electrode 130, and measuring a resulting impedance spectrum of the sensor (e.g., a set of data points representing the impedance of the sensor as a function of a variable frequency applied second voltage or current). Similar to the piezoelectric measurements, the concentration of an identified analyte can be calculated based on/correlated with one or more characteristic patterns in the impedance spectrum. Characteristic patterns can be identified relative to an established baseline in the impedance spectrum, or, similarly to the piezoelectric measurement, relative to some pre-measurement or pre-exposure baseline (e.g., established by analysis of an analyte-free reference gas either prior to, after, or in parallel with sample analysis with the same or different sensor).

The presence (or absence) of the analyte absorbed into the ionic liquid film can be determined by evaluating at least one measurement of the resonant frequency change, the voltammetric current trace, and/or the impedance spectrum. In general, a resonant frequency change, a voltammetric current trace, and/or an impedance spectrum that deviates from a known baseline and/or reference value (e.g., with signal peaks and/or patterns) indicates the presence of an absorbed solute. Conversely, a resonant frequency, a voltammetric current trace, and/or an impedance spectrum that is substantially the same as a known baseline/reference value indicates the absence of an absorbed solute. A benefit of having two or more independent measurement techniques (i.e., piezoelectric and one or more electrochemical) is that non-target constituents of the gaseous sample (e.g., non-environmental gases, environmental gases not of interest, non-explosive vapors and/or explosive vapor species not of interest) may potentially interfere with one of the techniques, leaving a second technique to confirm the presence or absence of one or more target analytes (e.g., those species determined to have an affinity for/be substantially soluble in the sensor's particular ionic liquid) in the gaseous sample. A single sensor 100 can be used to identify a species in the gaseous sample based on one or more characteristic peaks in the voltammetric current trace. Peaks identified from the analysis of reference analytes (e.g., environmental gas species, explosive vapor species) can establish characteristic peak locations (e.g., at a known voltage in the voltammetric current trace) and/or characteristic peak patterns (e.g., multiple peaks at known voltages, optionally also having known relative amplitude ratios between the multiple peaks). For example, as illustrated in FIG. 38, various DNT isomers have distinct peak patterns allowing the identification of individual species in a sample, even from complex mixtures of species. As described above, any characteristic peaks used to identify an explosive vapor species also can be used to calculate the concentration of the species.

In an embodiment, both piezoelectric and electrochemical measurements are performed by the sensing system. As illustrated in FIGS. 33A and 33B, the sensor 100 is electrically connected to both the potentiostat 200 and the AC voltage source 300. Thus, a single sensor 100 and/or its corresponding system is capable of performing piezoelectric and electrochemical measurement techniques. The system 400 with a single sensor 100 can be used to simultaneously perform both piezoelectric and electrochemical measurements. Simultaneous measurement can be desirable when power consumption of the system 400 is not of concern. Alternatively, piezoelectric and electrochemical measurements can be performed sequentially (e.g., toggling between both measuring modes at a predetermined interval). A suitable mode of sequential operation involves continuous, real-time piezoelectric detection on the sensor 100. Once there is a positive adsorption of an analyte on the ionic liquid film and a piezoelectric frequency change is recorded, the electrochemical measurement mode can be activated. While the piezoelectric method is generally more sensitive than the electrochemical method, the electrochemical method provides an independent method of detection (e.g., for analyte quantification, analyte identification, and/or independent verification of presence). Additionally, electrochemical methods can cause irreversible analyte modification (e.g., irreversible redox chemical transformations driven by applied electrochemical potentials), so it can be desirable to perform piezoelectric measurements first in sequence.

A QCM with various ionic liquid films (e.g., including $BMIBF_4$) as the sensing materials can be used for sensing organic vapors. FIG. 45 shows a typical sensorgram of ENB on a QCM/$BMIBF_4$ sensor. The response of ENB is reversible, reproducible and proportional to the ENB concentration. Using the method described in Jin et al., the Henry's constant of ENB in $BMIBF_4$ was evaluated to be about 139 Pa according to the data in FIG. 45. Typically, when ionic liquids are used as sensing materials, a single QCM sensor can not provide good selectivity to target analytes. Thus, a QCM/ionic-liquid sensor array can be used for classification and identification of gases or vapors.

A single element EQCM gas sensor that can detect and identify electroactive vapors such as ENB or other nitro compounds provides an alternative to a QCM array. Concentric gold rings-disk electrodes (FIGS. 32 and 35B) were deposited on one side of a piece of quartz substrate. On the other side, a single gold disk electrode was formed to align exactly with the disk electrode on the opposite side. A tiny drop (about 2-4 µL) of $BMIBF_4$ was deposited on the rings-disk side and spread to form a thin film. The resulting single piece of quartz functions both as an amperometric sensor as well as a QCM sensor (i.e., an EQCM sensor).

Figure 46B:
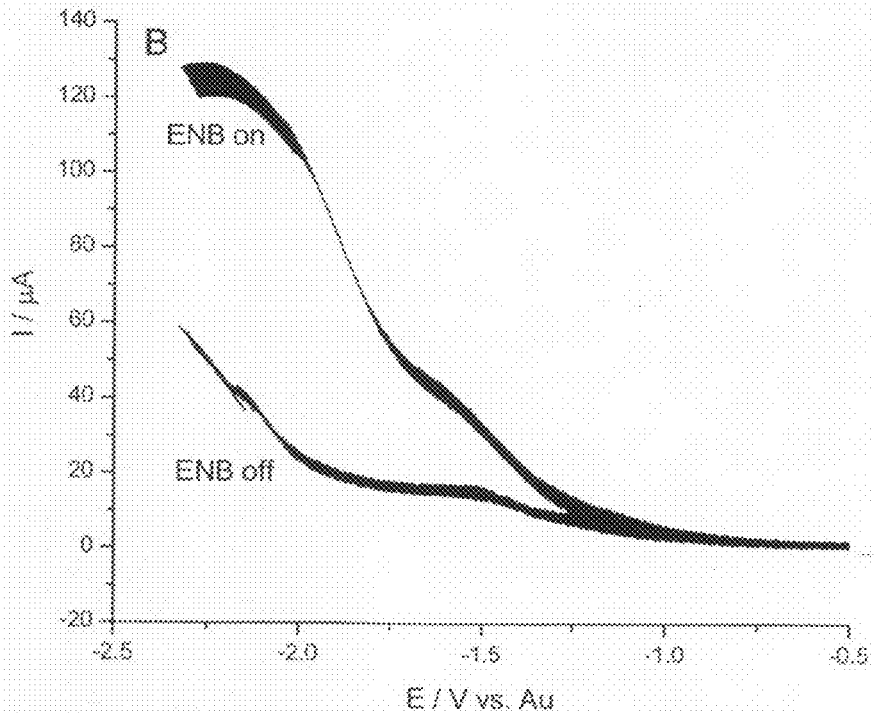

The EQCM sensor was placed in a chamber that was fed with a nitrogen gas. The nitrogen feed was cycled between two states: (a) nitrogen gas that was essentially free from ENB or other nitroaromatics, and (b) nitrogen gas that was saturated with ENB vapor (about 0.0895 mmHg at 25° C.). According to Henry's Law and the aforementioned Henry's constant, the ENB concentration in $BMIBF_4$ was calculated to be about 4.1 wt % in $BMIBF_4$. FIG. 46A shows the QCM sensorgram obtained while the ENB feed was cycled on and off with a period of about 2000 sec per cycle. Several factors may cause the QCM frequency change upon absorption of organic vapors into the IL film. Two of them are most important: mass loading on the surface and viscosity change of the surface layer. Under ideal conditions, when an ionic liquid film is very thin, a frequency change is only caused by mass loading on the surface, as described by the Sauerbrey equation. In this case, frequency is reduced upon absorption of gases, and the viscosity change or the damping resistance change of the QCM (related to viscosity) is not significant. However, when the ionic liquid film is thicker, the viscosity change is not negligible. When viscosity change is the major cause of frequency change in a QCM, the frequency will increase upon absorption of gases. In FIG. 45, a very thin $BMIBF_4$ film (i.e., on the order of tens of nm) was used, so the frequency decreases due to ENB mass loading. In FIG. 46A, the frequency change was positive due to the viscosity change of the $BMIBF_4$ film. Here, a thicker $BMIBF_4$ film (about 150 µm) was used to permit electrochemistry on the concentric rings-disk electrodes. FIG. 46B shows the background SWV and the SWV when the ENB was switched on. The signal due to ENB reduction could be clearly observed. These results demonstrate that that an EQCM gas sensor, which integrates both amperometric and QCM sensing modes on a single piece of quartz, could be developed for practical applications. The foregoing QCM sensing and amperometric sensing experiments utilized the same EQCM device but were measured separately due to instrumentation limitations. However, simultaneous amperometric and QCM sensing can be performed with appropriate wiring and external instrumentation using the existing EQCM device.

Summary: Ionic liquids (e.g., $BMIBF_4$ and others) can be used both as a solvent for the pre-concentration of explosives vapors (e.g., gas-phase nitroaromatics in the atmosphere/environment surrounding an EQCM sensor having a thin-film IL coating) and as an electrolyte for the amperometric detection of explosive compounds. Amperometric sensing and QCM sensing were verified in bulk $BMIBF_4$ solutions and in $BMIBF_4$ thin-film coated electrodes. Furthermore, amperometric sensing and QCM sensing were integrated together on a single quartz chip. Taking advantage of the fact that ionic liquids could be used as both electrolytes and vapor absorption materials, the sensing probes of amperometry and QCM methods were integrated on one EQCM chip. This detection technology was validated with nitroaromatic compounds ENB and various DNTs. The results indicate that both techniques could be used with the simple EQCM device. The two orthogonal methods may cross validate the measurement and increase the accuracy of detection. Thus, a single EQCM device can be used to both quantitate and qualitatively distinguish between multiple, different explosive vapors. Further miniaturization of the EQCM detection device incorporating both amperometric and QCM methods could lead to highly sensitive, specific and rapid detection gas sensor devices and systems.

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

Throughout the specification, where the compositions, processes, or apparatus are described as including components, steps, or materials, it is contemplated that the compositions, processes, or apparatus can also comprise, consist essentially of, or consist of, any combination of the recited components or materials, unless described otherwise. Combinations of components are contemplated to include homogeneous and/or heterogeneous mixtures, as would be understood by a person of ordinary skill in the art in view of the foregoing disclosure.

REFERENCES

[1] D.S. Silvester, A. J. Wain, L. Aldous, C. Hardacre, R. G. Compton, Electrochemical reduction of nitrobenzene and 4-nitrophenol in the room temperature ionic liquid [C(4)dmim][N(Tf)(2)], J. Electroanal. Chem. 596 (2006) 131-140.

[2] D.S. Silvester, R. G. Compton, Electrochemistry in room temperature ionic liquids: A review and some possible applications, Zeitschrift Fur Physikalische Chem.-Inter. J. Res. Phys. Chem. Chem. Phys. 220 (2006) 1247-1274.

[3] M. C. Kroon, W. Buijs, C. J. Peters, G. J. Witkamp, Decomposition of ionic liquids in electrochemical processing, Green Chem. 8 (2006) 241-245.

[4] T. Ueki, M. Watanabe, Macromolecules in Ionic Liquids: Progress, Challenges, and Opportunities, Macromolecules 41 (2008) 3739-3749.

[5] D.S. Moore, Recent Advances in Trace Explosives Detection Instrumentation, Sens. Imaging 8 (2007) 9-38.

[6] M. Nambayah, T. I. Quickenden, A quantitative assessment of chemical techniques for detecting traces of explosives at counter-terrorist portals, Talanta 63 (2004) 461-467.

[7] D.S. Moore, Instrumentation for trace detection of high explosives, Review of Scientific Instruments 75 (2004) 2499-2512.

[8] S. J. Toal, W. C. Trogler, Polymer sensors for nitroaromatic explosives detection, J. Mater. Chem. 16 (2006) 2871-2883.

[9] A. Cyr, P. Huot, J. F. Marcoux, G. Belot, E. Laviron, J. Lessard, The Electrochemical Reduction of Nitrobenzene and Azoxybenzene in Neutral and Basic Aqueous Methanolic Solutions at Polycrystalline Copper and Nickel Electrodes, Electrochim. Acta 34 (1989) 439-445.

[10] A. Cyr, E. Laviron, J. Lessard, Electrochemical-Behavior of Nitrobenzene and Phenylhydroxylamine on Copper Rotating-Disk Electrodes, J. Electroanal. Chem. 263 (1989) 69-78.

[11] L. J. Nunez-Vergara, M. Bonta, P.A. Navarrete-Encina, J. A. Squella, Electrochemical characterization of ortho and meta-nitrotoluene derivatives in different electrolytic media. Free radical formation, Electrochim. Acta 46 (2001) 4289-4300.

[12] L. Agui, D. Vega-Montenegro, P. Yanez-Sedeno, J. M. Pingarron, Rapid voltammetric determination of nitroaromatic explosives at electrochemically activated carbon-fibre electrodes, Anal. Bioanal. Chem. 382 (2005) 381-387.

[13] J.C. Chen, J. L. Shih, C. H. Liu, M. Y. Kuo, J. M. Zen, Disposable electrochemical sensor for determination of nitroaromatic compounds by a single-run approach, Anal. Chem. 78 (2006) 3752-3757.

[14] S. Hrapovic, E. Majid, Y. Liu, K. Male, J. H. T. Luong, Metallic nanoparticle-carbon nanotube composites for electrochemical determination of explosive nitroaromatic compounds, Anal. Chem. 78 (2006) 5504-5512.

[15] D. L. Lu, A. Cagan, R. A. A. Munoz, T. Tangkuaram, J. Wang, Highly sensitive electrochemical detection of trace liquid peroxide explosives at a Prussian-blue 'artificial-peroxidase' modified electrode, Analyst 131 (2006) 1279-1281.

[16] S. Y. Ly, D. H. Kim, M. H. Kim, Square-wave cathodic stripping voltammetric analysis of RDX using mercury-film plated glassy carbon electrode, Talanta 58 (2002) 919-926.

[17] N. P. Saravanan, S. Venugopalan, N. Senthilkumar, P. Santhosh, B. Kavita, H. G. Prabu, Voltammetric determination of nitroaromatic and nitramine explosives contamination in soil, Talanta 69 (2006) 656-662.

[18] J. Wang, Microchip devices for detecting terrorist weapons, Anal. Chim. Acta 507 (2004) 3-10.

[19] J. Wang, R. K. Bhada, J. M. Lu, D. MacDonald, Remote electrochemical sensor for monitoring TNT in natural waters, Anal. Chim. Acta 361 (1998) 85-91.

[20] J. Wang, S. B. Hocevar, B. Ogorevc, Carbon nanotube-modified glassy carbon electrode for adsorptive stripping voltammetric detection of ultratrace levels of 2,4,6-trinitrotoluene, Electrochem. Commun. 6 (2004) 176-179.

[21] J. Wang, F. Lu, D. MacDonald, J. M. Lu, M. E. S. Ozsoz, K. R. Rogers, Screen-printed voltammetric sensor for TNT, Talanta 46 (1998) 1405-1412.

[22] J. Wang, M. Pumera, Dual conductivity/amperometric detection system for microchip capillary electrophoresis, Anal. Chem. 74 (2002) 5919-5923.

[23] J. Wang, S. Thongngamdee, D. L. Lu, Sensitive voltammetric sensing of the 2,3-dimethyl-2,3-dinitrobutane (Dmnb) explosive taggant, Electroanalysis 18 (2006) 971-975.

[24] H. X. Zhang, A. M. Cao, J. S. Hu, L. J. Wan, S. T. Lee, Electrochemical sensor for detecting ultratrace nitroaromatic compounds using mesoporous SiO2-modified electrode, Anal. Chem. 78 (2006) 1967-1971.

[25] H. X. Zhang, J. S. Hu, C. J. Yan, L. Jiang, L. J. Wan, Functionalized carbon nanotubes as sensitive materials for electrochemical detection of ultra-trace 2,4,6-trinitrotoluene, Phys. Chem. Chem. Phys. 8 (2006) 3567-3572.

[26] X. S. Zhu, C. H. Ahn, On-chip electrochemical analysis system using nanoelectrodes and bioelectronic CMOS chip, Ieee Sensors J. 6 (2006) 1280-1286.

[27] http://en.wikipedia.org/wiki/Trinitrotoluene.

[28] X. X. Jin, L. Yu, D. Garcia, R. X. Ren, X. Q. Zeng, Ionic liquid high-temperature gas sensor array, Anal. Chem. 78 (2006) 6980-6989.

[29] L. Yu, D. Garcia, R. B. Rex, X. Q. Zeng, Ionic liquid high temperature gas sensors, Chem. Commun. (2005) 2277-2279.

[30] X. X. Jin, L. Yu, D. Garcia, R. X. Ren, X. Q. Zeng, Ionic liquid high-temperature gas sensor array, Analytical Chemistry 78 (2006) 6980-6989.

What is claimed is:

1. An electrochemical sensor comprising:
   (a) a substrate having a first surface and a second surface on opposing sides of the substrate;
   (b) a first electrode over the first surface;
   (c) a second electrode over the first surface and spaced apart from the first electrode;
   (d) a third electrode over the first surface and spaced apart from the first electrode and the second electrode; and,
   (e) an ionic liquid film over the first surface, the first electrode, the second electrode, and the third electrode;
   wherein the first electrode, the second electrode, and the third electrode are spaced apart to permit electrochemical measurement of an analyte absorbed in the ionic liquid film, and wherein the first electrode, second electrode and third electrode are arranged on the first surface of the substrate and adapted for connection to a potentiostat for use as a reference electrode, a working electrode, and a counter electrode in the electrochemical sensor, respectively.

2. The sensor of claim 1, wherein:
   (i) the second electrode comprises a portion that at least partially surrounds a portion of the first electrode; and
   (ii) the third electrode comprises a portion that at least partially surrounds a portion of the second electrode.

3. The sensor of claim 2, wherein:
   (i) a first distance between the portion of the third electrode and the portion of the second electrode that is at least partially surrounded ranges from 10 μm to 200 μm; and
   (ii) a second distance between the portion of the third electrode and the portion of the first electrode that is at least partially surrounded is more than 500 μm.

4. The sensor of claim 1, wherein:
   (i) the first electrode comprises a substantially disk-shaped portion;
   (ii) the second electrode comprises a substantially ring-shaped portion that (A) is positioned radially outwardly from the substantially disk-shaped portion of the first electrode and (B) at least partially surrounds the substantially disk-shaped portion of the first electrode; and
   (iii) the third electrode comprises a substantially ring-shaped portion that (A) is positioned radially outwardly from the substantially ring-shaped portion of the second electrode and (B) at least partially surrounds the substantially ring-shaped portion of the second electrode.

5. The sensor of claim 1, wherein:
   (i) the first electrode comprises a substantially disk-shaped portion;
   (ii) the second electrode comprises a substantially arc-shaped portion that is positioned radially outwardly from the substantially disk-shaped portion of the first electrode; and,
   (iii) the third electrode comprises a substantially arc-shaped portion that (A) is positioned radially outwardly from the substantially disk-shaped portion of the first electrode and (B) is at substantially the same radial position as the arc-shaped portion of the second electrode.

6. The sensor of claim 1, wherein the ionic liquid film has a thickness ranging from 60 μm to 500 μm.

7. The sensor of claim 1, wherein the ionic liquid film comprises:
   (i) a cation selected from the group consisting of ammonium cations, phosphonium cations, imidazolium cations, pyrrolidinium cations, pyridinium cations, and combinations thereof; and,
   (ii) an anion selected from the group consisting of sulfonates, bisulfates, inorganic halogenated anions, organic halogenated anions, tetrafluoroborate, hexafluorophosphate, bis(trifluoromethylsulfonyl) imide and combinations thereof.

8. The sensor of claim 1, wherein the ionic liquid film comprises an alkylated imidazolium cation and an inorganic halogenated anion.

9. The sensor of claim 1, wherein the ionic liquid film is bound to the first surface, the first electrode, the second electrode, and the third electrode with a binding agent selected from the group consisting of a self-assembled monolayer, a polyelectrolyte, a conductive polymer, a polyionic liquid, a zwitterionic liquid, and combinations thereof.

10. An electrochemical gas sensing system comprising:
    (a) the sensor of claim 1; and,
    (b) a DC voltage source electrically connected to (i) the first electrode as an electrochemical reference electrode, (ii) the second electrode as an electrochemical working electrode, and (iii) the third electrode as an electrochemical counter electrode.

11. The sensing system of claim 10, further comprising a plurality of sensors, each sensor comprising a substrate having a first surface and a second surface on opposing sides of the substrate; a first electrode over the first surface; a second electrode over the first surface and spaced apart from the first electrode; a third electrode over the first surface and spaced apart from the first electrode and the second electrode; and an ionic liquid film over the first surface, the first electrode, the second electrode, and the third electrode; wherein the first electrode, the second electrode, and the third electrode are spaced apart to permit electrochemical measurement of an analyte absorbed in the ionic liquid film, and wherein each sensor is electrically connected to a DC voltage source.

12. The sensor of claim 1, wherein a distance between the second electrode and the third electrode is in the range from 10 μm to 200 μm and a distance between the first electrode and the third electrode is from 500 μm to 5000 μm.

13. An electrochemical sensor comprising:
    (a) a substrate having a first surface and a second surface on opposing sides of the substrate;
    (b) a first electrode over the first surface;
    (c) a second electrode over the first surface and spaced apart from the first electrode;
    (d) a third electrode over the first surface and spaced apart from the first electrode and the second electrode; and,
    (e) an ionic liquid film over the first surface, the first electrode, the second electrode, and the third electrode;
    wherein the first electrode, the second electrode, and the third electrode are spaced apart to permit electrochemical measurement of an analyte absorbed in the ionic liquid film, and wherein the first electrode, second electrode and third electrode are arranged on the first surface of the substrate and adapted for connection to a potentiostat for use as a reference electrode, a working electrode, and a counter electrode in the electrochemical sensor, respectively,
    wherein:
    (i) the substrate comprises a piezoelectric material;
    (ii) the sensor further comprises (f) a fourth electrode over the second surface and substantially opposite the first electrode; and (iii) the first electrode and the fourth electrode permit piezoelectric measurement of the analyte absorbed in the ionic liquid film.

14. The sensor of claim 13, further comprising a second ionic liquid film over the second surface and the fourth electrode, wherein the first electrode and the fourth electrode permit piezoelectric measurement of the analyte absorbed in the second ionic liquid film.

15. The sensor of claim 13, further comprising an intermediate adhesion layer between the first electrode and the first surface, between the second electrode and the first surface, between the third electrode and the first surface, and between the fourth electrode and the second surface.

16. The sensor of claim 13, wherein:
(i) the first electrode, the second electrode, and the third electrode are on the first surface; and
(ii) the fourth electrode is on the second surface.

17. An electrochemical piezoelectric gas sensing system comprising:
(a) the sensor of claim 13;
(b) an AC voltage source electrically connected to (i) the first electrode as a piezoelectric sensing electrode and (ii) the fourth electrode as a piezoelectric contact electrode; and,
(c) a DC voltage source electrically connected to (i) the first electrode as an electrochemical reference electrode, (ii) the second electrode as an electrochemical working electrode, and (iii) the third electrode as an electrochemical counter electrode.

18. The sensing system of claim 17, further comprising a plurality of sensors, each sensor comprising a substrate having a first surface and a second surface on opposing sides of the substrate; a first electrode over the first surface; a second electrode over the first surface and spaced apart from the first electrode; a third electrode over the first surface and spaced apart from the first electrode and the second electrode; and an ionic liquid film over the first surface, the first electrode, the second electrode, and the third electrode; wherein the first electrode, the second electrode, and the third electrode are spaced apart to permit electrochemical measurement of an analyte absorbed in the ionic liquid film, wherein the substrate comprises a piezoelectric material; the sensor further comprises (f) a fourth electrode over the second surface and substantially opposite the first electrode; and, the first electrode and the fourth electrode permit piezoelectric measurement of the analyte absorbed in the ionic liquid film, wherein each sensor is electrically connected to an AC voltage source and a DC voltage source.

19. A method of analyzing a gaseous sample for the presence of an analyte therein, the method comprising:
(a) exposing the sensor of claim 13 to a gaseous sample, thereby absorbing at least a portion of any analyte present in the gaseous sample into the ionic liquid film;
(b) applying a first voltage across the first electrode and the fourth electrode, and measuring a resulting change in a resonant frequency in the piezoelectric substrate;
(c) applying a second voltage across the first electrode and the second electrode, and measuring a resulting voltammetric current trace across the second electrode and the third electrode; and,
(d) determining the presence of the analyte absorbed into the ionic liquid film by at least one of the resonant frequency change and the voltammetric current trace.

20. The method of claim 19, wherein:
(i) the first voltage is an AC voltage that permits piezoelectric measurement of an analyte absorbed in the ionic liquid film; and,
(ii) the second voltage is a DC voltage that permits electrochemical measurement of the analyte absorbed in the ionic liquid film.

21. The method of claim 19, further comprising:
(e) identifying the analyte in part (d) by one or more characteristic peaks in the voltammetric current trace.

22. The method of claim 21, further comprising:
(f) calculating the concentration of the identified analyte in part (e) with the one or more characteristic peaks in the voltammetric current trace.

23. The method of claim 21, further comprising:
(f) calculating the concentration of the identified analyte in part (e) with the resonant frequency change.

24. The method of claim 19, comprising performing parts (b) and (c) simultaneously.

25. The method of claim 19, comprising performing part (b) continuously until the resonant frequency change indicates the presence of the absorbed analyte and then performing part (c).

26. The method of claim 19, wherein part (c) comprises applying the second voltage in a time-dependent manner to perform one or more of cyclic voltammetry (CV), square wave voltammetry (SWV), and differential pulse voltammetry (DPV).

27. The method of claim 19, wherein the analyte comprises one or more nitro-containing ($-NO_2$) explosive vapor species.

28. The method of claim 27, wherein the explosive vapor species comprises one or more nitro-alkylaromatic compounds.

29. The method of claim 27, wherein the explosive vapor species comprises one or more of ethyl nitrobenzene and isomers thereof, dinitrobenzene and isomers thereof, and combinations thereof.

30. An electrochemical sensor comprising:
(a) a substrate having a first surface and a second surface on opposing sides of the substrate;
(b) a first electrode over the first surface;
(c) a second electrode over the first surface and spaced apart from the first electrode;
(d) a third electrode over the first surface and spaced apart from the first electrode and the second electrode; and,
(e) an ionic liquid film over the first surface, the first electrode, the second electrode, and the third electrode;
wherein the first electrode, the second electrode, and the third electrode are spaced apart to permit electrochemical measurement of an analyte absorbed in the ionic liquid film, and wherein the first electrode, second electrode and third electrode are arranged on the first surface of the substrate and adapted for connection to a potentiostat for use as a reference electrode, a working electrode, and a counter electrode in the electrochemical sensor, respectively; and
(f) a fourth electrode over the first surface and spaced apart from the first electrode, the second electrode, and the third electrode.

31. The sensor of claim 30, further comprising:
(g) a fifth electrode over the second surface and substantially opposite the first electrode;
wherein the substrate comprises a piezoelectric material, and the first electrode and the fifth electrode permit piezoelectric measurement of the analyte absorbed in the ionic liquid film.

32. An electrochemical piezoelectric gas sensing system comprising:
(a) the sensor of claim 31;
(b) an AC voltage source electrically connected to (i) the first electrode as a piezoelectric sensing electrode and (ii) the fifth electrode as a piezoelectric contact electrode; and
(c) a variable frequency voltage or current source electrically connected to (i) the first electrode as an electrochemical working electrode, (ii) the second electrode as an electrochemical reference electrode, (iii) the third electrode as an electrochemical counter electrode; and (iv) the fourth electrode as an electrochemical electrode.

33. A method of analyzing a gaseous sample for the presence of an analyte therein, the method comprising:
(a) exposing the sensor of claim 31 to a gaseous sample, thereby absorbing at least a portion of any analyte present in the gaseous sample into the ionic liquid film;
(b) applying a first voltage across the first electrode and the fifth electrode, and measuring a resulting change in a resonant frequency in the piezoelectric substrate;
(c) applying a second voltage or current across the first electrode and the second electrode, and measuring a resulting impedance spectrum of the sensor; and,
(d) determining the presence of the analyte absorbed into the ionic liquid film by at least one of the resonant frequency change and the impedance spectrum.

34. The method of claim 33, wherein:
(i) the first voltage is an AC voltage that permits piezoelectric measurement of an analyte absorbed in the ionic liquid film; and,
(ii) the second voltage or current is a variable frequency voltage or current that permits electrochemical measurement of the analyte absorbed in the ionic liquid film.

35. The method of claim 33, further comprising:
(e) identifying the analyte in part (d) by one or more characteristic patterns in the impedance spectrum.

36. The method of claim 35, further comprising:
(f) calculating the concentration of the identified analyte in part (e) with the one or more characteristic patterns in the impedance spectrum.

37. The method of claim 35, further comprising:
(f) calculating the concentration of the identified analyte in part (e) with the resonant frequency change.

38. The method of claim 33, comprising performing parts (b) and (c) simultaneously.

39. The method of claim 33, comprising performing part (b) continuously until the resonant frequency change indicates the presence of the absorbed analyte and then performing part (c).

40. The sensor of claim 30, wherein the fourth electrode comprises a substantially ring-shaped portion that (A) is positioned radially outwardly from the substantially ring-shaped portion of the third electrode and (B) at least partially surrounds the substantially ring-shaped portion of the third electrode.

41. An electrochemical gas sensing system comprising:
(a) the sensor of claim 30; and,
(b) a variable frequency voltage or current source electrically connected to (i) the first electrode as an electrochemical working electrode, (ii) the second electrode as an electrochemical reference electrode, (iii) the third electrode as an electrochemical counter electrode; and (iv) the fourth electrode as an electrochemical electrode.

42. An electrochemical piezoelectric sensor comprising:
(a) a piezoelectric quartz substrate having a first surface and a second surface on opposing sides of the piezoelectric quartz substrate;
(b) a first conducting metallic electrode over the first surface, the first electrode comprising a substantially disk-shaped portion;
(c) a second conducting metallic electrode over the first surface and spaced apart from the first electrode, the second electrode comprising a substantially ring-shaped portion that (A) is positioned radially outwardly from the substantially disk-shaped portion of the first electrode and (B) at least partially surrounds the substantially disk-shaped portion of the first electrode;
(d) a third conducting metallic electrode over the first surface and spaced apart from the first electrode and the second electrode, the third electrode comprising a substantially ring-shaped portion that (A) is positioned radially outwardly from the substantially ring-shaped portion of the second electrode and (B) at least partially surrounds the substantially ring-shaped portion of the second electrode;
(e) a fourth conducting metallic electrode over the second surface, the fourth electrode comprising a substantially disk-shaped portion that is substantially aligned with the substantially disk-shaped portion of the first electrode; and,
(f) an ionic liquid film over the first surface, the first electrode, the second electrode, and the third electrode;
wherein (i) the first electrode, the second electrode, and the third electrode are spaced apart to permit electrochemical measurement of an analyte absorbed in the ionic liquid film, and (ii) first electrode and the fourth electrode permit piezoelectric measurement of the analyte absorbed in the ionic liquid film.

43. The sensor of claim 42, further comprising:
(g) a fifth conducting metallic electrode over the first surface and spaced apart from the first electrode, the second electrode, and the third electrode, the fifth electrode comprising a substantially ring-shaped portion that (A) is positioned radially outwardly from the substantially ring-shaped portion of the third electrode and (B) at least partially surrounds the substantially ring-shaped portion of the third electrode.

44. An electrochemical piezoelectric gas sensing system comprising:
(a) the sensor of claim 43;
(b) an AC voltage source electrically connected to (i) the first electrode as a piezoelectric sensing electrode and (ii) the fourth electrode as a piezoelectric contact electrode; and,
(c) a variable frequency voltage or current source electrically connected to (i) the first electrode as an electrochemical working electrode, (ii) the second electrode as an electrochemical reference electrode, (iii) the third electrode as an electrochemical counter electrode; and (iv) the fifth electrode as an electrochemical counter electrode.

45. The sensor of claim 42, further comprising:
(g) a second ionic liquid film over the second surface and the fourth electrode, wherein the first electrode and the fourth electrode permit piezoelectric measurement of the analyte absorbed in the second ionic liquid film.

46. The sensor of claim 42, wherein:
(i) a first distance between the portion of the third electrode and the portion of the second electrode that is at least partially surrounded ranges from 20 μm to 100 μm;

(ii) a second distance between the portion of the third electrode and the portion of the first electrode that is at least partially surrounded ranges from 600 μm to 3000 μm; and, (iii) the ionic liquid film has a thickness ranging from 100 μm to 400 μm.

47. The sensor of claim 42, wherein the ionic liquid film comprises:

(i) a cation selected from the group consisting of ammonium cations, phosphonium cations, imidazolium cations, pyrrolidinium cations, pyridinium cations, and combinations thereof; and, (ii) an anion selected from the group consisting of sulfonates, bisulfates, tetrafluoroborate, hexafluorophosphate, bis(trifluoromethylsulfonyl) imide, and combinations thereof.

48. An electrochemical piezoelectric gas sensing system comprising:

(a) the sensor of claim 42;

(b) an AC voltage source electrically connected to (i) the first electrode as a piezoelectric sensing electrode and (ii) the fourth electrode as a piezoelectric contact electrode; and, (c) a DC voltage source electrically connected to (i) the first electrode as an electrochemical reference electrode, (ii) the second electrode as an electrochemical working electrode, and (iii) the third electrode as an electrochemical counter electrode.

\* \* \* \* \*